US012616711B2

(12) United States Patent
Owen et al.

(10) Patent No.: US 12,616,711 B2
(45) Date of Patent: May 5, 2026

(54) THERAPEUTIC DENDRIMER

(71) Applicant: Starpharma Pty Ltd, Abbotsford (AU)

(72) Inventors: David James Owen, Preston (AU); Rashmi Pathak, Preston (AU)

(73) Assignee: Starpharma Pty Ltd., Abbotsford (AU)

( * ) Notice: Subject to any disclaimer, the term of this patent is extended or adjusted under 35 U.S.C. 154(b) by 899 days.

(21) Appl. No.: 17/763,887

(22) PCT Filed: Sep. 25, 2020

(86) PCT No.: PCT/AU2020/051028

§ 371 (c)(1),
(2) Date: Mar. 25, 2022

(87) PCT Pub. No.: WO2021/056077

PCT Pub. Date: Apr. 1, 2021

(65) Prior Publication Data

US 2022/0395525 A1 Dec. 15, 2022

(30) Foreign Application Priority Data

Sep. 26, 2019 (AU) ................................ 2019903628
Oct. 30, 2019 (AU) ................................ 2019904094

(51) Int. Cl.

*A61K 31/7068* (2006.01)
*A61K 47/59* (2017.01)
*A61K 47/60* (2017.01)

(52) U.S. Cl.

CPC .......... *A61K 31/7068* (2013.01); *A61K 47/59* (2017.08); *A61K 47/595* (2017.08); *A61K 47/60* (2017.08)

(58) Field of Classification Search

CPC .... A61K 31/7068; A61K 47/60; A61K 47/59; A61K 47/595

See application file for complete search history.

(56) References Cited

U.S. PATENT DOCUMENTS

2004/0152759 A1 8/2004 Abrams et al.
2018/0326081 A1 11/2018 Owen et al.

FOREIGN PATENT DOCUMENTS

WO 2003/055935 A1 7/2003
WO 2007/048190 A1 5/2007
WO 2007/082331 A1 7/2007
WO 2011/012722 A1 2/2011
WO WO2012/167309 A1 * 12/2012 ............ A61K 47/48
WO 2018/002761 A1 1/2018
WO 2018/154004 A1 8/2018
WO 2020/014750 A1 1/2020
WO 2020/102852 A1 5/2020

OTHER PUBLICATIONS

Vandana et al., Synergistic activity of combination therapy with PEGylated pemetrexed and gemcitabine for an effective cancer treatment. Eur J Pharm Biopharm. Aug. 2015;94:83-93.
International Search Report and Written Opinion for Application No. PCT/AU2020/051028, dated Nov. 17, 2020, 11 pages.
Ciccolini et al., Pharmacokinetics and pharmacogenetics of Gemcitabine as a mainstay in adult and pediatric oncology: an EORTC-PAMM perspective. Cancer Chemother Pharmacol. Jul. 2016;78(1):1-12.

* cited by examiner

*Primary Examiner* — Scarlett Y Goon
*Assistant Examiner* — Samantha Lynn Schachermeyer
(74) *Attorney, Agent, or Firm* — McCarter & English, LLP

(57) ABSTRACT

Provided herein are dendrimers comprising a core unit, five generations of building units being a lysine residue or analogue thereof, a plurality of first terminal groups each comprising a residue of a nucleoside analogue, and a plurality of second terminal groups each comprising a hydrophilic polymeric group. Also provided herein are pharmaceutical compositions comprising the dendrimer, and methods and uses of the dendrimers in therapy of disorders such as cancer.

22 Claims, 6 Drawing Sheets

THERAPEUTIC DENDRIMER

RELATED APPLICATION

This application is a 35 U.S.C. § 371 national stage filing of International Application No. PCT/AU2020/051028, filed on Sep. 25, 2020, which in turn claims the benefit of Australian Patent Application No. 2019903628, filed on Sep. 26, 2019 and Australian Patent Application No. 2019904094, filed on Oct. 30, 2019. The entire contents of each of the foregoing applications are incorporated herein by reference.

FIELD

The present disclosure relates to the delivery of nucleoside analogue-based oncology agents by means of drug-dendrimer conjugates. The drug-dendrimer conjugates comprise a dendrimer including a core and building units, with the outermost generation of building units including one or more nucleoside analogue oncology agents attached via a cleavable linker group. The present disclosure also relates to pharmaceutical compositions and methods of treatment comprising the drug-dendrimer conjugates, and to processes and synthetic intermediates for producing the drug-dendrimer conjugates comprising nucleoside analogue-based oncology agents.

BACKGROUND

Oncology agents are an important class of pharmaceuticals, and there have been significant advances in the chemotherapeutic treatment of cancer in recent decades. However, therapeutic application of oncology agents is often hampered by difficulties associated with their formulation and delivery, including poor pharmacokinetics properties such as rapid metabolism and/or excretion, and/or lack of targeting to the site of action. Further, a number of oncology agents are associated with severe side effects, providing a narrow therapeutic window, limiting the dosage regimen that can be used, and potentially reducing the efficacy of the treatment.

Nucleoside analogues such as gemcitabine have been shown to be effective in the therapy of some cancers, including ovarian, breast pancreatic and lung cancers. Gemcitabine acts by being incorporated into the DNA and RNA of rapidly dividing cells, such as cancer cells, and interfering with their growth and repair. However, gemcitabine also has drawbacks as a pharmaceutical agent, in that it is rapidly metabolised in vivo by cytidine deaminase, and it also undergoes renal clearance (Ciccolini et al, Cancer Chemother Pharmacol, 2016, 78, p1-12), requiring high doses. Gemcitabine therapy is also associated with a number of side effects, including pulmonary toxicity and respiratory failure, haemolytic uremic syndrome, renal impairment, severe hepatic toxicity, capillary leak syndrome, and posterior reversible encephalopathy syndrome (see for example the prescribing information for Gemzar®).

To combat some of these difficulties, oncology agents may be specially formulated to try and counter the limitations of the drug substance itself. For example, in the case of gemcitabine, approaches investigated include encapsulation of the pharmaceutically active agent in liposomes and micelles.

Nonetheless, there remains a need for alternative and/or improved oncology therapies.

SUMMARY

It has been found that nucleoside analogue-dendrimer conjugates have surprising properties such that the amount of nucleoside analogue required (as part of the conjugate) to provide effective therapy is significantly reduced compared to free drug. The conjugates of the invention facilitate controlled release of the nucleoside analogue, and use of the conjugates is expected to have reduced side effects and/or enhanced efficacy.

In a first aspect, there is provided a dendrimer comprising:

i) a core unit (C); and ii) building units (BU), each building unit being a lysine residue or an analogue thereof;

wherein the core unit is covalently attached to two building units via amide linkages, each amide linkage being formed between a nitrogen atom present in the core unit and the carbon atom of an acyl group present in a building unit;

the dendrimer being a five generation building unit dendrimer;

wherein building units of different generations are covalently attached to one another via amide linkages formed between a nitrogen atom present in one building unit and the carbon atom of an acyl group present in another building unit;

the dendrimer further comprising:

iii) a plurality of first terminal groups (T1) each comprising a residue of a nucleoside analogue, which nucleoside analogue has a hydroxyl group, covalently attached to a diacyl linker group of formula:

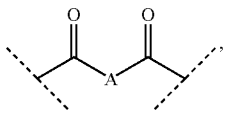

wherein A is a $C_2$-$C_{10}$ alkylene group which is interrupted by at least one O, S, NH, or N(Me), or in which A is a heterocycle selected from the group consisting of tetrahydrofuran, tetrahydrothiophene, pyrrolidine, and N-methylpyrrolidine; and iv) a plurality of second terminal groups (T2) each comprising a hydrophilic polymeric group;

or a pharmaceutically acceptable salt thereof.

In some embodiments, the nucleoside analogue is selected from the group consisting of gemcitabine, cytarabine, and azacitadine. In some embodiments, the nucleoside analogue is gemcitabine. In some embodiments, the core unit is formed from a core unit precursor comprising two amino groups. In some embodiments, the core unit is:

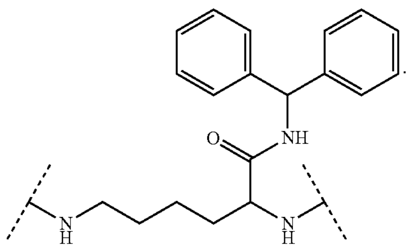

In some embodiments, the building units are each:

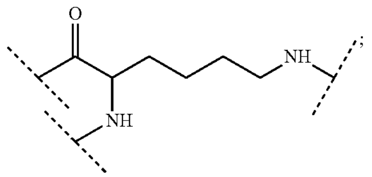

wherein the acyl group of each building unit provides a covalent attachment point for attachment to the core or to a previous generation building unit; and wherein each nitrogen atom provides a covalent attachment point for covalent attachment to a subsequent generation building unit, a first terminal group or a second terminal group.

In some embodiments, the diacyl linker is selected from the group consisting of:

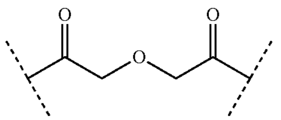

and

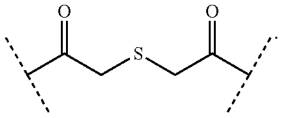

In some embodiments, the diacyl linker is:

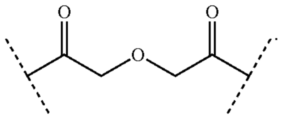

In some embodiments, the diacyl linker is:

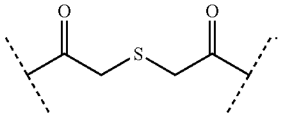

In some embodiments, the nucleoside analogue is gemcitabine and is covalently attached to the diacyl linker group as shown below:

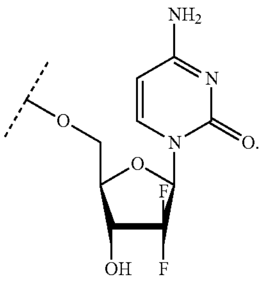

In some embodiments, the nucleoside analogue is gemcitabine and is covalently attached to the diacyl linker group as shown below:

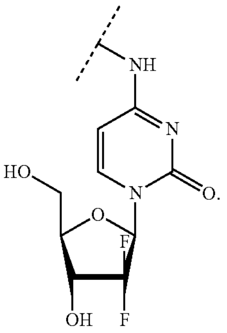

In some embodiments, the first terminal group is:

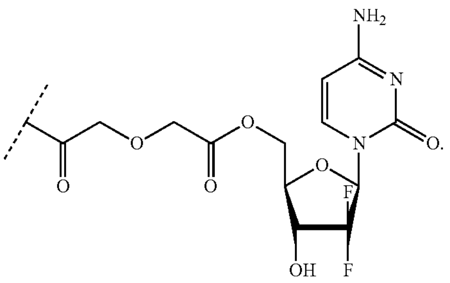

In some embodiments, the first terminal group is:

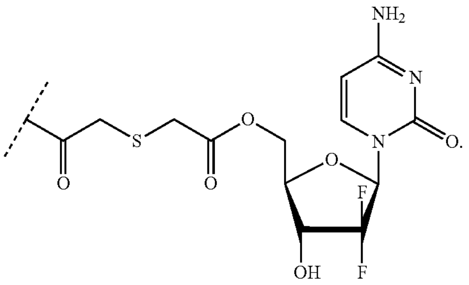

In some embodiments, the hydrophilic polymeric group is selected from the group consisting of polyethylene glycol (PEG), polyethyloxazoline (PEOX), and polysarcosine. In some embodiments, the second terminal groups comprise PEG groups having a mean molecular weight of at least 500 Daltons. In some embodiments, the second terminal groups comprise PEG groups having an average molecular weight in the range of from 1900 to 2300 Daltons. In some embodiments, the second terminal groups each comprise a PEG group covalently attached to a PEG linking group (L1) via an ether linkage formed between a carbon atom present in the PEG group and an oxygen atom present in the PEG linking group, and each second terminal group is covalently attached to a building unit via an amide linkage formed between a nitrogen atom present in a building unit and the carbon atom of an acyl group present in the PEG linking group. In some embodiments, the second terminal groups are each:

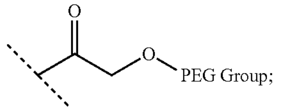

and wherein the PEG group is a methoxy-terminated PEG having an average molecular weight in the range of from 500 to 2500 Daltons.

In some embodiments, the dendrimer comprises surface units comprising an outer building unit attached to a first terminal group and a second terminal group, the surface units having the structure:

in which T1' represents a first terminal group which is

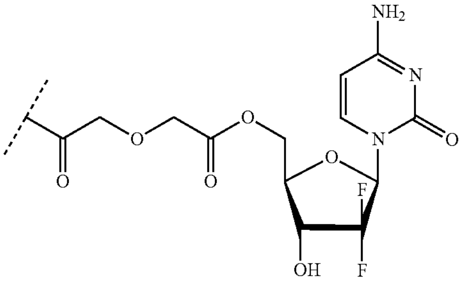

or

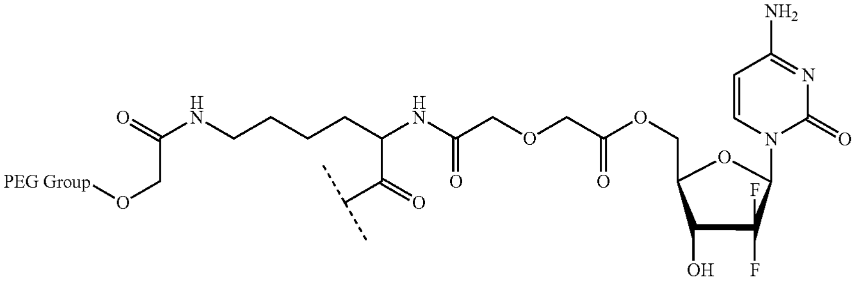

or

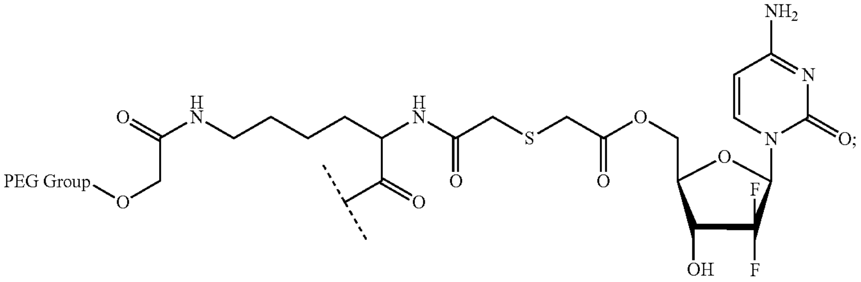

and wherein the PEG group is a methoxy-terminated PEG having an average molecular weight in the range of from 500 to 2500 Daltons.

In some embodiments, the dendrimer has from 28 to 32 surface units. In some embodiments, at least 40% of the nitrogen atoms present in the outer building units are each covalently attached to a first terminal group; and at least 40% of the nitrogen atoms present in the outer building units are each covalently attached to a second terminal group. In some embodiments, the five generations of building units are complete generations, and wherein the outer generation of building units provides 64 nitrogen atoms for covalent attachment to a first terminal group or a second terminal group, wherein from 24 to 32 first terminal groups are covalently attached to one of said nitrogen atoms, and wherein from 24 to 32 second terminal groups are each covalently attached to one of said nitrogen atoms.

In some embodiments, when the dendrimer is exposed to PBS at pH 7.4 and 37° C., between about 20% and about 90% of the residue of the nucleoside analogue is released from the dendrimer after 24 hours.

In some embodiments, the dendrimer is a compound having a structure as shown in FIG. 10, -continued

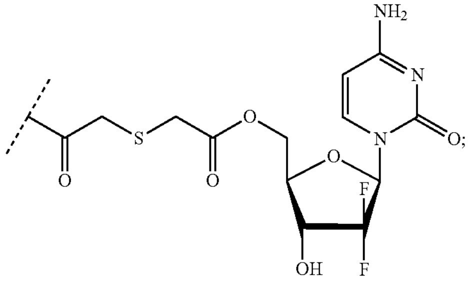

and

T2' represents a second terminal group which is:

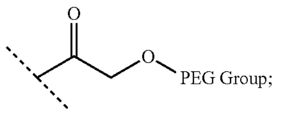

wherein the PEG group is a methoxy-terminated PEG having an average molecular weight in the range of from 500 to 2500 Daltons, or T2' represents H, and wherein less than 5 of T2' are H.

In another aspect, there is provided a pharmaceutical composition comprising: i) a dendrimer as described herein, or a pharmaceutically acceptable salt thereof; and ii) a pharmaceutically acceptable excipient.

In another aspect, there is provided a dendrimer as described herein, or a pharmaceutical composition as described herein, for use in the treatment of cancer.

In another aspect, there is provided a method of treating cancer comprising administering to a subject in need thereof a therapeutically effective amount of a dendrimer as described herein, or a pharmaceutical composition as described herein.

In another aspect, there is provided the use of a dendrimer as described herein, or of a composition as described herein, in the manufacture of a medicament for the treatment of cancer.

In some embodiments, the cancer is selected from the group consisting of breast cancer, ovarian cancer, non-small cell lung cancer, an upper gastrointestinal cancer (e.g. pancreatic cancer), and bladder cancer. In some embodiments, the amount of dendrimer administered is sufficient to deliver an amount of active agent in the range of from 5 mg to 200 mg of nucleoside analogue/$m^2$. In some embodiments, the dendrimer is administered in combination with a further anticancer agent. In some embodiments, the further anticancer agent is selected from the group consisting of platinum-containing pharmaceutical agents, taxanes, immunooncology agents, PARP inhibitors, topoisomerase I inhibitors, antibodies, antifolates, tyrosine kinase inhibitors, anthracyclines, and vinca alkaloids. In some embodiments, the anticancer agent is selected from the group consisting of capecitabine, Nab-paclitaxel (e.g. Abraxane®), docetaxel, cabazitaxel, doxorubicin, vindesine, irinotecan, folinic acid, 5-fluorouracil, methotrexate, pemetrexed, lapatinib, nintedanib, sunitinib, olaparib, niraparib, carboplatin, paclitaxel, SN38, cisplatin, oxaliplatin, paclitaxel, erlotinib, and irinotecan.

In some embodiments, the dendrimer is administered in combination with a second dendrimer, and wherein the second dendrimer comprises:

i) a core unit (C); and ii) building units (BU), each building unit being a lysine residue or an analogue thereof;

wherein the core unit is covalently attached to two building units via amide linkages, each amide linkage being formed between a nitrogen atom present in the core unit and the carbon atom of an acyl group present in a building unit;

the dendrimer being a five generation building unit dendrimer;

wherein building units of different generations are covalently attached to one another via amide linkages formed between a nitrogen atom present in one building unit and the carbon atom of an acyl group present in another building unit;

the dendrimer further comprising:

iii) a plurality of first terminal groups (T1) each comprising a residue of an oncology agent, which oncology agent has a hydroxyl group, covalently attached to a diacyl linker group of formula:

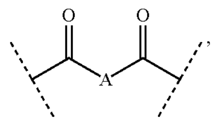

wherein A is a $C_2$-$C_{10}$ alkylene group which is interrupted by at least one O, S, NH, or N(Me), or in which A is a heterocycle selected from the group consisting of tetrahydrofuran, tetrahydrothiophene, pyrrolidine, and N-methylpyrrolidine; and iv) a plurality of second terminal groups (T2) each comprising a hydrophilic polymeric group; or a pharmaceutically acceptable salt thereof.

In some embodiments, the oncology agent is a taxane. In some embodiments, the taxane is selected from the group consisting of docetaxel, paclitaxel and cabazitaxel. In some embodiments, the taxane is docetaxel. In some embodiments, the oncology agent is a topoisomerase I inhibitor. In some embodiments, the topoisomerase I inhibitor is SN-38.

In some embodiments, administration of the dendrimer provides enhanced clinical efficacy in comparison to administration of an equivalent dose of free nucleoside analogue. In some embodiments, administration of the dendrimer provides reduced side effects and/or toxicity in comparison to administration of an equivalent dose of free nucleoside analogue. In some embodiments, administration of the dendrimer provides therapeutically effective plasma concentration levels of gemcitabine for an extended period of time following administration, in comparison to administration of an equivalent dose of free nucleoside analogue.

DESCRIPTION

General Definitions

Figure 1:
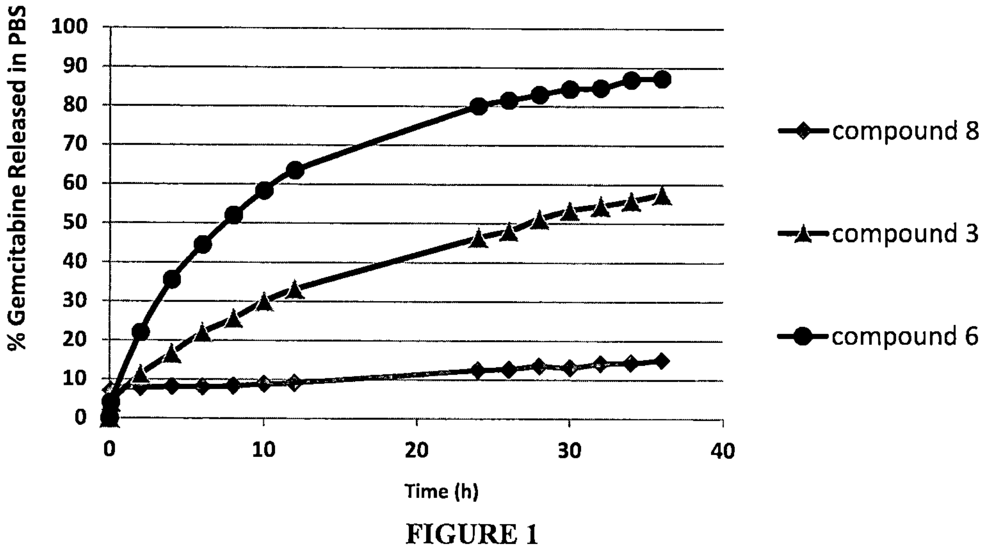
FIG. 1 shows the amount of gemcitabine released (%) from the dendrimer in PBS at pH 7.4 and 37° C.

Unless specifically defined otherwise, all technical and scientific terms used herein shall be taken to have the same meaning as commonly understood by one of ordinary skill in the art (e.g., chemistry, biochemistry, medicinal chemistry, polymer chemistry, and the like).

As used herein, the term "and/or", e.g., "X and/or Y" shall be understood to mean either "X and Y" or "X or Y" and shall be taken to provide explicit support for both meanings or for either meaning.

As used herein, the term "about", unless stated to the contrary, refers to +/−20%, more preferably +/−10%, of the designated value.

As used herein, singular forms "a", "an" and "the" include plural aspects, unless the context clearly indicates otherwise.

Throughout this specification, the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein, the term "subject" refers to any organism susceptible to a disease or condition. In one embodiment, the disease or condition is cancer. For example, the subject can be a mammal, primate, livestock (e.g., sheep, cow, horse, pig), companion animal (e.g., dog, cat), or laboratory animal (e.g., mouse, rabbit, rat, guinea pig, hamster). In one example, the subject is a mammal. In one embodiment, the subject is human.

As used herein, the term "treating" includes alleviation of the symptoms associated with a specific disorder or condition and eliminating said symptoms. For example, as used herein, the term "treating cancer" refers to alleviating the symptoms associated with cancer and eliminating said symptoms. In one embodiment, the term "treating cancer" refers to a reduction in cancerous tumour size. In one embodiment, the term "treating cancer" refers to an increase in progression-free survival. As used herein, the term "progression-free survival" refers to the length of time during and after the treatment of cancer that a patient lives with the disease, i.e., cancer, but does not have a recurrence or increase in symptoms of the disease.

As would be understood by the person skilled in the art, a dendrimer would be administered in a therapeutically effective amount. The term "therapeutically effective amount", as used herein, refers to a dendrimer being administered in an amount sufficient to alleviate or prevent to some extent one or more of the symptoms of the disorder or condition being treated. The result can be the reduction and/or alleviation of the signs, symptoms, or causes of a disease or condition, or any other desired alteration of a biological system. In one embodiment, the term "therapeutically effective amount" refers to a dendrimer being administered in an amount sufficient to result in a reduction in cancerous tumour size. In one embodiment, the term "therapeutically effective amount" refers to a dendrimer being administered in an amount sufficient to result in an increase in progression-free survival. The term, an "effective amount", as used herein, refers to an amount of a dendrimer effective to achieve a desired pharmacologic effect or therapeutic improvement without undue adverse side effects or to achieve a desired pharmacologic effect or therapeutic improvement with a reduced side effect profile. By way of example only, therapeutically effective amounts may be determined by routine experimentation, including but not limited to a dose escalation clinical trial. The term "therapeutically effective amount" includes, for example, a prophylactically effective amount. In one embodiment, a prophylactically effective amount is an amount sufficient to prevent metastasis. It is understood that "an effective amount" or "a therapeutically effective amount" can vary from subject to subject, due to variation in metabolism of the compound and any of age, weight, general condition of the subject, the condition being treated, the severity of the condition being treated, and the judgment of the prescribing physician. Thus, it is not always possible to specify an exact "effective amount". However, an appropriate "effective amount" in any individual case may be determined by one of ordinary skill in the art using routine experimentation. Where more than one therapeutic agent is used in combination, a "therapeutically effective amount" of each therapeutic agent can refer to an amount of the therapeutic agent that would be therapeutically effective when used on its own, or may refer to a reduced amount that is therapeutically effective by virtue of its combination with one or more additional therapeutic agents.

Suitable salts of the dendrimers include those formed with organic or inorganic acids or bases. As used herein, the phrase "pharmaceutically acceptable salt" refers to pharmaceutically acceptable organic or inorganic salts. Exemplary acid addition salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. Exemplary base addition salts include, but are not limited to, ammonium salts, alkali metal salts, for example those of potassium and sodium, alkaline earth metal salts, for example those of calcium and magnesium, and salts with organic bases, for example dicyclohexylamine, N-methyl-D-glucomine, morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethyl-propylamine, or a mono-, di- or trihydroxy lower alkylamine, for example mono-, di- or triethanolamine. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion. It will also be appreciated that non-pharmaceutically acceptable salts also fall within the scope of the present disclosure since these may be useful as intermediates in the preparation of pharmaceutically acceptable salts or may be useful during storage or transport.

Those skilled in the art of organic and/or medicinal chemistry will appreciate that many organic compounds can form complexes with solvents in which they are reacted or from which they are precipitated or crystallized. These complexes are known as "solvates". For example, a complex with water is known as a "hydrate". As used herein, the phrase "pharmaceutically acceptable solvate" or "solvate"

refer to an association of one or more solvent molecules and a compound of the present disclosure. Examples of solvents that form pharmaceutically acceptable solvates include, but are not limited to, water, isopropanol, ethanol, methanol, DMSO, ethyl acetate, acetic acid, and ethanolamine.

As used herein, the term "dendrimer" refers to a molecule containing a core and dendrons attached to the core. Each dendron is made up of generations of branched building units resulting in a branched structure with increasing number of branches with each generation of building units. A "dendrimer", including a drug-dendrimer conjugate, may include pharmaceutically acceptable salts or solvates as defined supra.

As used herein, the term "building unit" refers to a branched molecule which is a lysine residue or an analogue thereof having three functional groups, one for attachment to the core or a previous generation of building units and at least two functional groups for attachment to the next generation of building units or forming the surface of the dendrimer molecule.

As used herein, the term "attached" refers to a connection between chemical components by way of covalent bonding. The term "covalent bonding", as used herein, refers to a chemical bond formed by the sharing of one or more electrons, especially pairs of electrons, between atoms. The term "covalent bonding" is used interchangeable with the term "covalent attachment".

Dendrimers

In a first aspect there is provided a dendrimer comprising:

i) a core unit (C); and ii) building units (BU), each building unit being a lysine residue or an analogue thereof;

wherein the core unit is covalently attached to two building units via amide linkages, each amide linkage being formed between a nitrogen atom present in the core unit and the carbon atom of an acyl group present in a building unit;

the dendrimer being a five generation building unit dendrimer;

wherein building units of different generations are covalently attached to one another via amide linkages formed between a nitrogen atom present in one building unit and the carbon atom of an acyl group present in another building unit;

the dendrimer further comprising:

iii) a plurality of first terminal groups (T1) each comprising a residue of a nucleoside analogue, which nucleoside analogue has a hydroxyl group, covalently attached to a diacyl linker group of formula:

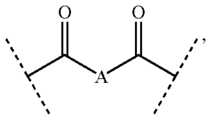

wherein A is a $C_2$-$C_{10}$ alkylene group which is interrupted by at least one O, S, NH, or N(Me), or in which A is a heterocycle selected from the group consisting of tetrahydrofuran, tetrahydrothiophene, pyrrolidine, and N-methylpyrrolidine; and iv) a plurality of second terminal groups (T2) each comprising a hydrophilic polymeric group;

or a pharmaceutically acceptable salt thereof.

Core Unit

The core unit (C) of the dendrimer is covalently attached to two building units via amide linkages, each amide linkage being formed between a nitrogen atom present in the core unit and the carbon atom of an acyl group present in a building unit. Accordingly, the core unit may for example be formed from a core unit precursor comprising two amino groups. Any suitable diamino-containing molecule may be used as the core unit precursor. In some embodiments, the core unit is:

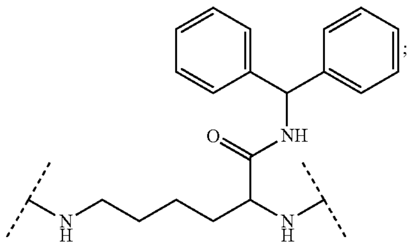

and may, for example, be formed from a core unit precursor:

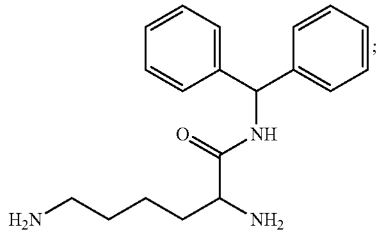 [SMILES: NCCCCC(N)C(=O)NC(c1ccccc1)c1ccccc1]

having two reactive (amino) nitrogens.

Building Units

The building units (BU) are lysine residues or analogues thereof, and may be formed from suitable building unit precursors, e.g. lysine or lysine analogues containing appropriate protecting groups. Lysine analogues have two amino nitrogen atoms for bonding to a subsequent generation of building units and an acyl group for bonding to a previous generation of building units or a core. Examples of suitable building units include:

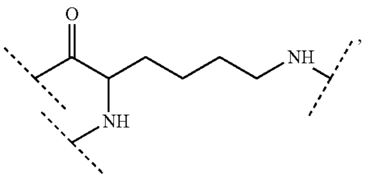

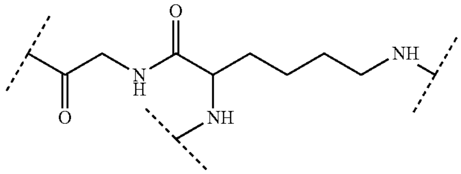

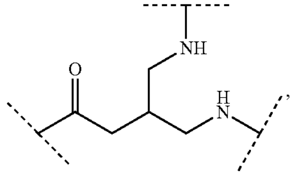

-continued

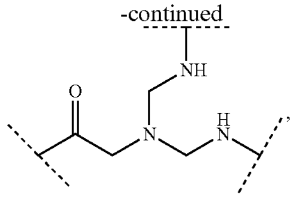

and

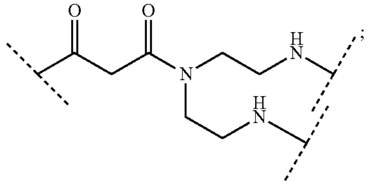

wherein the acyl group of each building unit provides a covalent attachment point for attachment to the core or to a previous generation building unit; and wherein each nitrogen atom provides a covalent attachment point for covalent attachment to a subsequent generation building unit, a first terminal group or a second terminal group.

In some preferred embodiments, the building units are each:

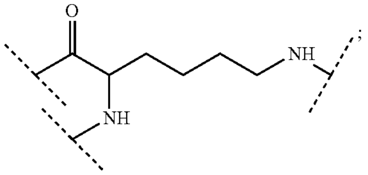

wherein the acyl group of each building unit provides a covalent attachment point for attachment to the core or to a previous generation building unit; and wherein each nitrogen atom provides a covalent attachment point for covalent attachment to a subsequent generation building unit, a first terminal group or a second terminal group.

In some preferred embodiments, the building units are each:

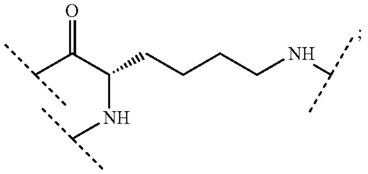

wherein the acyl group of each building unit provides a covalent attachment point for attachment to the core or to a previous generation building unit; and wherein each nitrogen atom provides a covalent attachment point for covalent attachment to a subsequent generation building unit, a first terminal group or a second terminal group.

The outermost generation of building units ($BU_{outer}$) may be formed by lysine or lysine analogue building units as used in the other generations of building units (BU) as described above. The outermost generation of building units ($BU_{outer}$) is the generation of building units that is outermost from the core of the dendrimer, i.e., no further generations of building units are attached to the outermost generation of building units ($BU_{outer}$).

It will be appreciated that the dendrons of the dendrimer may for example be synthesised to the required number of generations through the attachment of building units (BU) accordingly. In some embodiments each generation of building units (BU) may be formed of the same building unit, for example all of the generations of building units may be lysine building units. In some other embodiments, one or more generations of building units may be formed of different building units to other generations of building units.

The dendrimer is a five generation building unit dendrimer. A five generation building unit dendrimer is a dendrimer having a structure which includes five building units which are covalently linked to another, for example in the case where the building units are lysines, it may comprise the substructure:

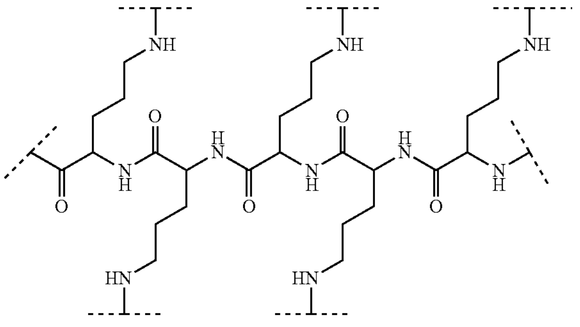

In some embodiments, the dendrimer has five complete generations of building units. With a core having two reactive amine groups, such a dendrimer will comprise 62 building units (i.e. core unit+2 BU+4 BU+8 BU+16 BU+32 BU). However, it will be appreciated that, due to the nature of the synthetic process for producing the dendrimers, one or more reactions carried out to produce the dendrimers may not go fully to completion. Accordingly, in some embodiments, the dendrimer may comprise an incomplete generations of building units. For example, a population of dendrimers may be obtained, in which the dendrimers have a distribution of numbers of building units per dendrimer. In some embodiments, a population of dendrimers is obtained which has a mean number of building units per dendrimer of at least 55, or at least 56, or at least 57, or at least 58, or at least 59, or at least 60. In some embodiments, a population of dendrimers is obtained in which at least 60%, at least 70%, at least 80%, at least 90% or at least 95% of the dendrimers have 55 or more building units. In some embodiments, a population of dendrimers is obtained in which at least 60%, at least 70%, at least 80%, at least 90% or at least 95% of the dendrimers have 60 or more building units.

Each reactive (amino) group of the core represents a conjugation site for a dendron comprising one or more generations of building units. The core has two reactive (amino) groups, and two dendrons, for the generations of building units to be attached.

In some embodiments, each generation of building units in each dendron (X) may be represented by the formula $[BU]_{2(b-1)}$, wherein b is the generation number. A dendron (X), having five complete generations of building units is represented as $[BU]_1$—$[BU]_2$—$[BU]_4$—$[BU]_8$—$[BU]_{16}$.

Nucleoside Analogues

The dendrimer comprises a residue of a nucleoside analogue. Nucleoside analogues are a group of therapeutic agents which find use in applications such as cancer therapy.

The nucleoside analogues contain one or more hydroxyl groups which can be utilised for linking of the nucleoside analogue to the dendrimer via the linker. In some embodiments, the nucleoside analogues may, in addition to the hydroxyl group, contain other groups which can be utilised for linking to the dendrimer. Similarly, the nucleoside analogue may contain one or more amino groups which can be utilised for linking of the nucleoside analogue to the linker (e.g., a diacyl linker).

Examples of nucleoside analogues include pyrimidine nucleoside analogues, e.g. gemcitabine, deoxycytidine, cytarabine, 5'-aza-cytidine (also known as azacitidine), capecitabine and decitabine. Further examples include purine nucleoside analogues, such as cladribine, clofarabine, fludarabine, doxifluridine, forodesine, nelarabine and pentostatin.

In some embodiments, that nucleoside analogue is a pyrimidine nucleoside analogue. In some embodiments, the nucleoside analogue is an anticancer nucleoside analogue. In some embodiments, the nucleoside analogue is gemcitabine, azacitidine or cytarabine.

In one embodiment, the nucleoside analogue is gemcitabine. Gemcitabine is an oncology agent having the structure:

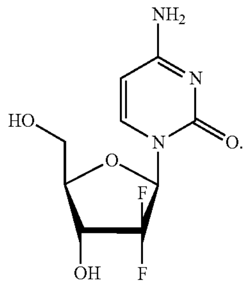

In some embodiments, the residue of the nucleoside analogue active is attached to the diacyl linker through the 3'- or 5'-position of the nucleoside analogue. In some embodiments, the residue of a nucleoside analogue active has the substructure: 3'-attached pyrimidine nucleoside analogue. In some embodiments, the residue of a nucleoside analogue active has the substructure: 5'-attached pyrimidine nucleoside analogue. In some embodiments, the residue of a nucleoside analogue active has the substructure: 3'-attached purine nucleoside analogue. In some embodiments, the residue of a nucleoside analogue active has the substructure: 5'-attached purine nucleoside analogue. In some embodiments, the nucleoside analogue is an anticancer nucleoside analogue which is attached via the 5' hydroxyl group. In some embodiments, the nucleoside analogue is gemcitabine, azacytidine, or cytarabine, which are attached via the 5' hydroxyl group. In one embodiment, the nucleoside analogue is gemcitabine which is attached via the 5' hydroxyl group. In other words, in that embodiment, the nucleoside analogue is covalently attached as shown below:

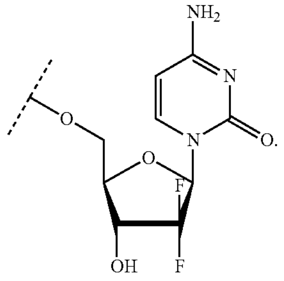

In some embodiments, the residue of a nucleoside analogue active has an amino group, and the residue of a nucleoside analogue active is attached to the diacyl linker through an amino group. In some embodiments, the nucleoside analogue is gemcitabine which is attached via the amino group. In other words, in that embodiment, the nucleoside analogue is covalently attached as shown below:

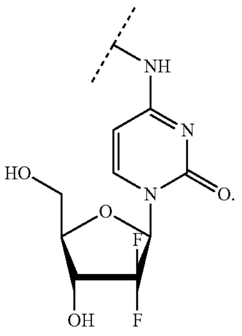

Upon in vivo administration, typically the dendrimer releases the nucleoside analogue (e.g., gemcitabine).

Linker

The residue of a nucleoside analogue active is covalently attached to a diacyl linker group of formula:

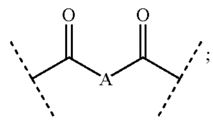

wherein A is a $C_2$-$C_{10}$ alkylene group which is interrupted by at least one O, S, NH, or N(Me), or in which A is a heterocycle selected from the group consisting of tetrahydrofuran, tetrahydrothiophene, pyrrolidine, and N-methylpyrrolidine.

As used herein, the term "alkyl" refers to straight (i.e., linear) or branched chain hydrocarbons ranging in size from one to 10 carbon atoms (i.e. $C_{1-10}$alkyl). Thus, alkyl moieties include, unless explicitly limited to smaller groups, moieties ranging in size, for example, from about one to about six carbon atoms or greater, such as, methyl, ethyl, n-propyl, iso-propyl and/or butyl, pentyl, hexyl, and higher isomers. In one example, the alkyl moiety is of one to 10 carbon atoms (i.e. $C_{1-10}$alkyl). In another example, the alkyl moiety is of 2 to 4 carbon atoms, preferably 4 carbon atoms.

As used herein, the term "alkylene" refers to straight (i.e. linear) or branched chain hydrocarbons ranging in size from 1 to 10 carbon atoms (i.e. $C_{1-10}$alkylene). Thus, alkylene moieties include, for example, $—CH_2—$, $—CH_2CH_2—$, $—CH_2CH_2CH_2—$, $—CH_2CH(CH_3)—$, $—CH_2CH_2CH_2CH_2—$, $—CH_2CH(CH_3)CH_2—$, and the like.

In some embodiments, the diacyl linker is:

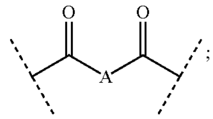

wherein A is a $C_2$-$C_{10}$ alkylene group (e.g straight chain or branched) which is interrupted by at least one O, S, NH, or N(Me).

In some embodiments, the diacyl linker is:

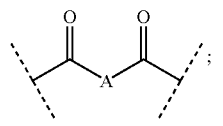

wherein A is a $C_2$-$C_6$ alkylene group (e.g. straight chain or branched) which is interrupted by at least one O, S, NH, or N(Me).

In some embodiments, the diacyl linker is selected from the group consisting of:

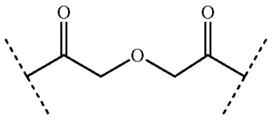

and

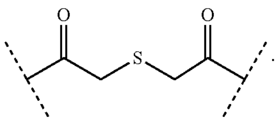

In some embodiments, the diacyl linker is:

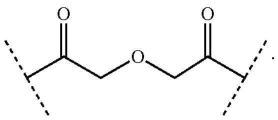

In some embodiments, the diacyl linker is:

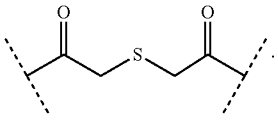

The residue of a nucleoside analogue active is typically covalently attached to the diacyl linker via a linkage formed between an oxygen atom present as part of the nucleoside analogue active side-chain and a carbon atom of an acyl group present as part of the diacyl linker. The other acyl group of the diacyl linker forms an amide linkage with a nitrogen atom present in an outer building unit.

In some embodiments, the nucleoside analogue is gemcitabine and is covalently attached to the diacyl linker group as shown below:

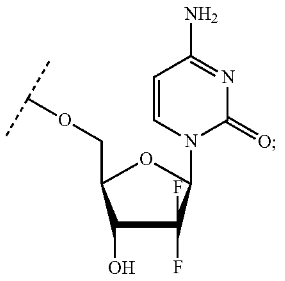

and wherein the diacyl linker is:

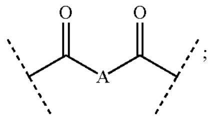

wherein A is a $C_2$-$C_{10}$ alkylene group which is interrupted by O, S, NH, or N(Me), or in which A is a heterocycle selected from the group consisting of tetrahydrofuran, tetrahydrothiophene, pyrrolidine and N-methylpyrrolidine.

In some embodiments, the first terminal group is:

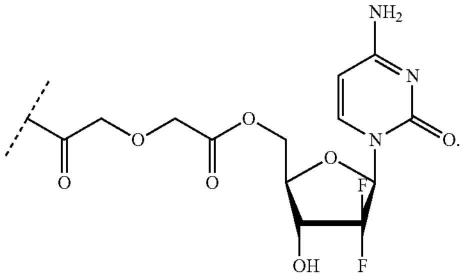

In some embodiments, the first terminal group is:

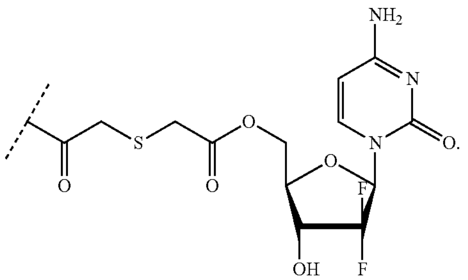

The inventors have found that, by the combination of particular cleavable linker groups, with specific hydroxyl groups present in the nucleoside analogue structure, that controlled and consistent release of nucleoside analogue active can be achieved, leading to good biological activity and good pharmacokinetic properties. For example, the 3' site of a nucleoside analogue is typically more sterically hindered than the 5' position. However, linker groups have been identified which release drug from the dendrimer at a desirable rate, which can be conjugated with the nucleoside analogue active in high yield, and which can also be used to achieve good levels of loading of nucleoside analogue active onto the dendrimer.

Whilst the residue of a nucleoside analogue active is typically covalently attached to the diacyl linker via a linkage formed between an oxygen atom present as part of the nucleoside analogue active, the linkage may also be formed via another suitable atom, e.g. where the nucleoside analogue active contains an amino group, the linkage may be formed via a nitrogen atom present in the amino group.

Second Terminal Group

The dendrimer comprises a plurality of second terminal groups (T2) each comprising a hydrophilic polymeric group. The second terminal group T2 is a pharmacokinetic modifying agent. A pharmacokinetic modifying agent is an agent that can modify or modulate the pharmacokinetic profile of the dendrimer or the pharmaceutically active agent (i.e. gemcitabine) that the dendrimer is delivering. The pharmacokinetic modifying agent may modulate the absorption, distribution, metabolism, excretion and/or toxicity of the dendrimer of the pharmaceutically active agent. The pharmacokinetic modifying agent (T2) may influence the rate of release of the pharmaceutically active agent, either by slowing or increasing the rate in which the active agent is released from the dendrimer by either chemical (e.g., hydrolysis) or enzymatic degradation pathways. The pharmacokinetic modifying agent (T2) may change the solubility profile of the dendrimer, either increasing or decreasing the solubility of the dendrimer in a pharmaceutically acceptable carrier. The pharmacokinetic modifying agent (T2) may assist the dendrimer in delivering the pharmaceutically active agent to specific tissues (e.g., tumours). The pharmacokinetic modifying agent (T2) may extend the pharmaceutically active agent half-life by reducing clearance of the dendrimer.

The term "hydrophilic polymeric group" typically refers to a polymeric group that has a solubility in water at 25° C. of at least 25 mg/ml, more preferably at least 50 mg/ml, and, still more preferably at least 100 mg/ml. In some embodiments, the hydrophilic polymeric group comprises repeating units of amino acids, alkyloxy, or alkyl(acyl)amino groups. In some embodiments, the hydrophilic polymeric group comprises repeating units of amino acids, such as sarcosine. In some embodiments, the hydrophilic polymeric group comprises repeating units of alkyloxy groups (e.g. the hydrophilic polymer is a PEG group). In some embodiments the hydrophilic polymer comprises repeating units of alkyl (acyl)amino groups (e.g. the hydrophilic polymer is a PEOX group). In some embodiments, the hydrophilic polymeric group is a PEG group. In some embodiments, the hydrophilic polymeric group is a PEOX group. In some embodiments, the hydrophilic polymeric group is a polysarcosine group.

In some embodiments, the hydrophilic polymeric group comprises at least 10 monomer units. In some embodiments, the hydrophilic polymeric group comprises up to 100 monomer units. In some embodiments, the hydrophilic polymeric group comprises from 10 to 100, or from 10 to 50 monomer units.

In one embodiment, the second terminal group comprises a PEG group (i.e., the hydrophilic polymeric group is a PEG group). A PEG group is a polyethylene glycol group, i.e. a group comprising repeat units of the formula $-CH_2CH_2O-$. PEG materials used to produce the dendrimer of the present disclosure typically contain a mixture of PEGs having some variance in molecular weight (i.e., ±10%), and therefore the molecular weight specified is typically an approximation of the average molecular weight of the PEG composition. For example, the term "$PEG_{\sim2100}$" refers to polyethylene glycol having an average molecular weight of approximately 2100 Daltons, i.e. ±approximately 10% (i.e., $PEG_{1890}$ to $PEG_{2310}$). The term "$PEG_{\sim2300}$" refers to polyethylene glycol having an average molecular weight of approximately 2300 Daltons, i.e. ±approximately 10% ($PEG_{2070}$ to $PEG_{2530}$). Three methods are commonly used to calculate MW averages: number average, weight average, and z-average molecular weights. As used herein, the phrase "molecular weight" is intended to refer to the weight-average molecular weight which can be measured using techniques well-known in the art including, but not limited to, NMR, mass spectrometry, matrix-assisted laser desorption ionization time of flight (MALDI-TOF), gel permeation chromatography or other liquid chromatography techniques, light scattering techniques, ultracentrifugation and viscometry.

In some embodiments, the second terminal groups comprise PEG groups having an average molecular weight of between about 200 and 5000 Daltons. In some embodiments, the second terminal groups comprise PEG groups having an average molecular weight of at least 500 Daltons. In some embodiments, the second terminal groups comprise PEG groups having an average molecular weight of at least 750 Daltons. In some embodiments, the second terminal groups comprise PEG groups having an average molecular weight in the range of from 500 to 2500 Daltons.

In some embodiments, the second terminal groups comprise PEG groups having an average molecular weight in the range of from 1900 to 2300 Daltons. In some embodiments, the second terminal groups comprise PEG groups having an average molecular weight in the range of from 2000 to 2200 Daltons. In some embodiments, the second terminal groups comprise PEG groups having an average molecular weight of about 2100 Daltons. In some embodiments, the second terminal groups comprise PEG groups having an average molecular weight of about 1900, about 2000, about 2100, about 2200, about 2300, about 2400 or about 2500 Daltons.

In some embodiments, the second terminal groups comprise PEG groups having an average molecular weight in the range of from 1000 to 1200 Daltons. In some embodiments, the second terminal groups comprise PEG groups having an average molecular weight of about 1100 Daltons. In some embodiments, the second terminal groups comprise PEG groups having an average molecular weight of about 1000, about 1100, or about 1200 Daltons.

In some embodiments, the second terminal groups comprise PEG groups having an average molecular weight in the range of from 500 to 650 Daltons. In some embodiments, the second terminal groups comprise PEG groups having an average molecular weight of about 570 Daltons. In some embodiments, the second terminal groups comprise PEG groups having an average molecular weight of about 500, about 530, about 550, about 570, about 590, about 610, about 630, or about 650 Daltons.

In some embodiments, the PEG group has a polydispersity index (PDI) of between about 1.00 and about 1.50, between about 1.00 and about 1.25, or between about 1.00 and about 1.10. In some embodiments, the PEG group has a polydispersity index (PDI) of about 1.05. The term "polydispersity index" refers to a measure of the distribution of molecular mass in a given polymer sample. The polydispersity index (PDI) is equal to the weight average molecular weight (Mw) divided by the number average molecular weight (Mn) and indicates the distribution of individual molecular masses in a batch of polymers. The polydispersity index (PDI) has a value equal to or greater than one, but as the polymer approaches uniform chain length and average molecular weight, the polydispersity index (PDI) will be closer to one.

Where the second terminal groups comprise a PEG group, the PEG groups may be linear or branched. If desired, an end-capped PEG group may be used. In some embodiments, the PEG group is a methoxy-terminated PEG.

In one embodiment the second terminal group comprises a PEOX group (i.e., the hydrophilic polymeric group is a PEOX group). A PEOX group is a polyethyloxazoline group, i.e. a group comprising repeat units of the formula:

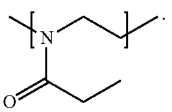

PEOX groups are so named since they can be produced by polymerisation of ethyloxazoline. PEOX materials used to produce the dendrimer of the present disclosure typically contain a mixture of PEOXs having some variance in molecular weight (i.e., ±10%), and therefore, where a molecular weight is specified, it is typically an approximation of the average molecular weight of the PEOX composition. In some embodiments, the second terminal groups comprise PEOX groups having an average molecular weight of at least 750 Daltons, at least 1000 Daltons, or at least 1500 Daltons. In some embodiments, the second terminal groups comprise PEOX groups having an average molecular weight in the range of from 750 Daltons to 2500 Daltons, or from 1000 Daltons to 2000 Daltons. If desired, an end-capped PEOX group may be used. In some embodiments, the PEOX group is a methoxy-terminated PEOX.

In some embodiments, the hydrophilic polymeric group comprises a polysarcosine group. In some embodiments, the polysarcosine groups have an average molecular weight of at least 750 Daltons, at least 1000 Daltons, or at least 1500 Daltons. In some embodiments, the hydrophilic polymeric groups comprise polysarcosine groups having an average molecular weight in the range of from 750 Daltons to 2500 Daltons, or from 1000 Daltons to 2000 Daltons.

The hydrophilic polymeric group may be attached to the outer building unit via any suitable means. In some embodiments, a linking group is used to attach the hydrophilic polymeric group to the outer building unit.

The second terminal group may be attached to the outer building unit via any suitable means. In some embodiments, a linking group is used to attach the hydrophilic polymeric group (e.g., PEG group, PEOX group, or polysarcosine group) to the outer building unit.

The second terminal groups are typically attached via use of a second terminal group precursor which contains a reactive group that is reactive with an amine group, such as a reactive acyl group (which can form an amide bond), or an aldehyde (which can form an amine group under reductive amination conditions).

In some embodiments, the second terminal groups each comprise a PEG group covalently attached to a PEG linking group (L1) via an ether linkage formed between a carbon atom present in the PEG group and an oxygen atom present in the PEG linking group, and each second terminal group is covalently attached to a building unit via an amide linkage formed between a nitrogen atom present in a building unit and the carbon atom of an acyl group present in the PEG linking group. In some embodiments, the second terminal groups are each:

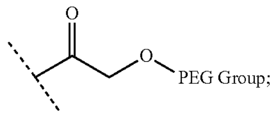

and wherein the PEG group is a methoxy-terminated PEG having an average molecular weight in the range of from about 500 to 2500 Daltons.

In some embodiments, the second terminal groups each comprise a PEOX group covalently attached to a PEOX linking group (L1') via a linkage formed between a nitrogen atom present in the PEOX group and a carbon atom present in the PEOX linking group, and each second terminal group is covalently attached to a building unit via an amide linkage formed between a nitrogen atom present in a building unit and the carbon atom of an acyl group present in the PEOX linking group. In some embodiments, the second terminal groups are each:

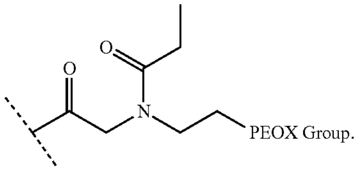

In some embodiments, the second terminal groups each comprise a polysarcosine group, i.e. a group comprising repeat units of the formula:

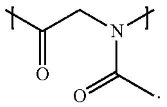

In some embodiments, the polysarcosine groups are attached to a building unit via an amide linkage formed between a nitrogen atom present in a building unit and the carbon atom of an acyl group present in the polysarcosine group. In some embodiments, the hydrophilic polymeric groups comprise polysarcosine groups having an average molecular weight of at least 750 Daltons, at least 1000 Daltons, or at least 1500 Daltons. In some embodiments, the second terminal groups comprise polysarcosine groups having an average molecular weight in the range of from 750 Daltons to 2500 Daltons, or from 1000 Daltons to 2000 Daltons.

In the dendrimers of the present disclosure, typically at least one third of the nitrogen atoms present in outer building units are each covalently attached to a first terminal group; and at least one third of the nitrogen atoms present in outer building units are each covalently attached to a second terminal group.

In some embodiments, the dendrimers have controlled stoichiometry and/or topology. For example, the dendrimers are typically produced using synthetic processes that allow for a high degree of control over the number and arrangement of first and second terminal groups present on the dendrimers. In some embodiments, each functionalised outer building unit contains one first terminal group and one second terminal group.

In some embodiments, the dendrimer comprises surface units comprising an outer building unit attached to a first terminal group and a second terminal group, the surface units having the structure:

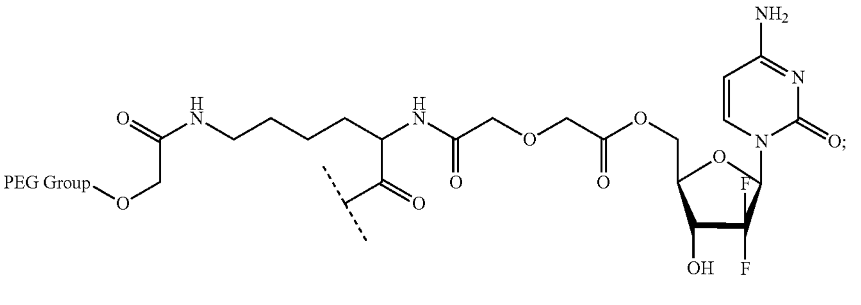

and wherein the PEG group is a methoxy-terminated PEG having an average molecular weight in the range of from about 500 to 2500 Daltons (e.g. about 2000 to 2400 Daltons).

In some embodiments, the dendrimer comprises surface units comprising an outer building unit attached to a first terminal group and a second terminal group, the surface units having the structure:

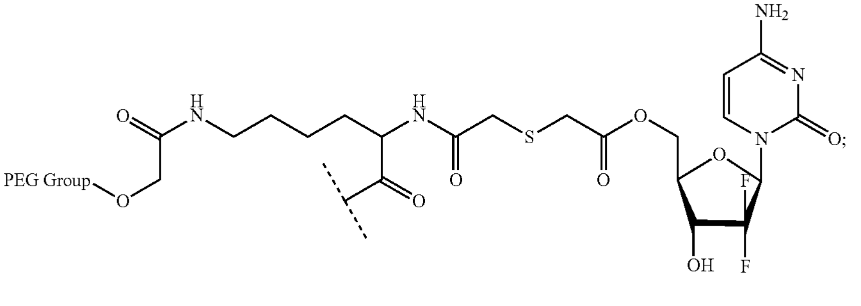

and wherein the PEG group is a methoxy-terminated PEG having an average molecular weight in the range of from about 500 to 2500 Daltons (e.g. about 2000 to 2400 Daltons).

In some embodiments, the dendrimer has from 28 to 32 surface units. In some embodiments, the dendrimer has from 30 to 32 surface units.

In some embodiments, at least 40% of the nitrogen atoms present in the outer building units are each covalently attached to a first terminal group. In some embodiments, at least 45% of the nitrogen atoms present in the outer building units are each covalently attached to a first terminal group. In some embodiments, about 50% of the nitrogen atoms present in the outer building units are each covalently attached to a first terminal group.

In some embodiments, at least 40% of the nitrogen atoms present in the outer building units are each covalently attached to a second terminal group. In some embodiments, at least 45% of the nitrogen atoms present in the outer building units are each covalently attached to a second terminal group. In some embodiments, about 50% of the nitrogen atoms present in the outer building units are each covalently attached to a second terminal group.

In some embodiments, at least 40% of the nitrogen atoms present in the outer building units are each covalently attached to a first terminal group; and at least 40% of the nitrogen atoms present in the outer building units are each covalently attached to a second terminal group. In some embodiments, at least 45% of the nitrogen atoms present in the outer building units are each covalently attached to a first terminal group; and at least 45% of the nitrogen atoms present in the outer building units are each covalently attached to a second terminal group. In some embodiments, about 50% of the nitrogen atoms present in the outer building units are each covalently attached to a first terminal group; and about 50% of the nitrogen atoms present in the outer building units are each covalently attached to a second terminal group.

In some embodiments, the five generations of building units are complete generations, and wherein the outer generation of building units provides 64 nitrogen atoms for covalent attachment to a first terminal group or a second terminal, wherein from 24 to 32 first terminal groups are covalently attached to one of said nitrogen atoms, and wherein from 24 to 32 second terminal groups are each covalently attached to one of said nitrogen atoms.

In some embodiments, from 26 to 32, or from 28 to 32 first terminal groups are each covalently attached to one of said nitrogen atoms. In some embodiments, from 29 to 31 first terminal groups are each covalently attached to one of said nitrogen atoms. In some embodiments, from 26 to 32, or from 28 to 32 second terminal groups are each covalently attached to one of said nitrogen atoms. In some embodiments, from 29 to 31 second terminal groups are each covalently attached to one of said nitrogen atoms In some embodiments the first terminal group comprises less than 20% w/w of the dendrimer, or less than 15% w/w of the dendrimer, or less than 10% w/w of the dendrimer, or between 5 and 30% w/w of the dendrimer, or between 8 and 15% w/w of the dendrimer, e.g. as measured by $^{1}H$ NMR.

In some embodiments, no more than one quarter of the nitrogen atoms present in the outer generation of building units are unsubstituted. In some embodiments, no more than one fifth of the nitrogen atoms present in said outer generation of building units are unsubstituted. In some embodiments, no more than one sixth of the nitrogen atoms present in said outer generation of building units are unsubstituted. In some embodiments, no more than one eighth of the nitrogen atoms present in said outer generation of building units are unsubstituted. In some embodiments, no more than one tenth of the nitrogen atoms present in said outer generation of building units are unsubstituted.

In some embodiments, no more than 20 nitrogen atoms present in the outer generation of building units are unsubstituted. In some embodiments, no more than 10 nitrogen atoms present in the outer generation of building units are unsubstituted. In some embodiments, no more than 5 nitrogen atoms present in the outer generation of building units are unsubstituted. In some embodiments, no more than 3 nitrogen atoms present in the outer generation of building units are unsubstituted. In some embodiments, no more than 2 nitrogen atoms present in the outer generation of building units are unsubstituted. In some embodiments, no more than 1 nitrogen atom present in the outer generation of building units are unsubstituted. In some embodiments, substantially all of the nitrogen atoms present in the outer generation of building units are substituted.

Figure 10:
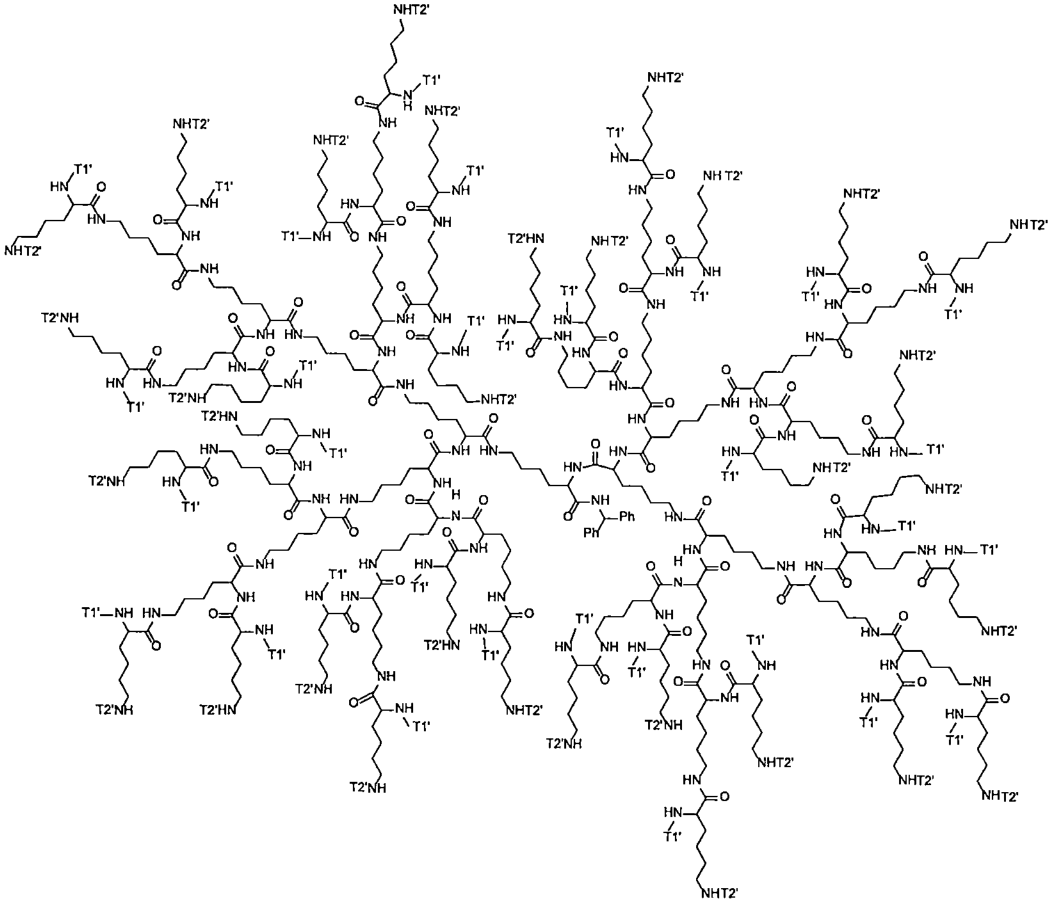
FIG. 10 shows the structure of a dendrimer of the disclosure.

In some embodiments, the dendrimer is a compound having a structure as shown in FIG. 10, in which T1' represents a first terminal group which is:

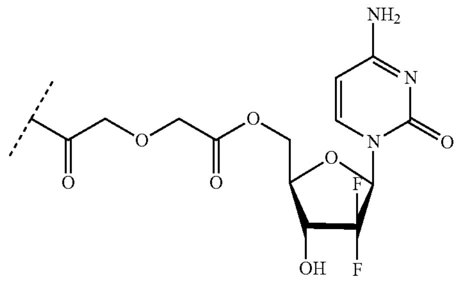

or

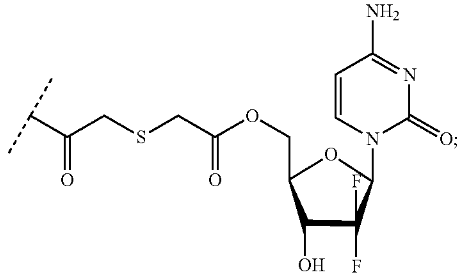

T2' represents a second terminal group which is:

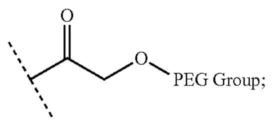

wherein the PEG group is a methoxy-terminated PEG having an average molecular weight in the range of from 500 to 2500 Daltons, or T2' represents H, and wherein less than 5 of T2' are H.

In some embodiments, the dendrimer has a molecular weight in the range of from 25 to 300 kDa, or from 40 to 300 kDa, or from 75 to 200 kDa, or from 90 to 150 kDa. In some embodiments, the dendrimer has a molecular weight in the range of from 35 to 100 kDa. In one example, the dendrimer has a molecular weight in the range of from 35 to 45 kDa, or in the range of from 50 to 60 kDa, or in the range of from 85 to 95 kDa.

In some embodiments, the in vitro half-life is the point at which 50% of drug is released from the dendrimer. In some embodiments, the in vitro half-life may be determined by using a least squares fitting to a $1^{st}$ order release model.

In some embodiments, the in vitro half-life for nucleoside analogues (e.g. gemcitabine) release from the dendrimer in PBS (phosphate-buffer saline) at pH 7.4 and at 37° C. is in the range of from 2 to 50 hours. In some embodiments, the in vitro half-life for nucleoside analogue (e.g. gemcitabine) release from the dendrimer in PBS at pH 7.4 and at 37° C. is in the range of from 5 to 50 hours, or 10 to 50 hours, or 5 to 40 hours, or 5 to 30 hours, or 10 to 30 hours. In some embodiments, the in vitro half-life for nucleoside analogue (e.g. gemcitabine) release from the dendrimer in PBS at pH 7.4 and at 37° C. is in the range of from 2 to 10 hours. In some embodiments, the in vitro half-life for nucleoside analogue (e.g. gemcitabine) release from the dendrimer in PBS at pH 7.4 and at 37° C. is in the range of from 20 to 40 hours.

In some embodiments, the percentage nucleoside analogue (e.g. gemcitabine) released from the dendrimer after 24 hours in PBS (phosphate-buffer saline) at pH 7.4 and at 37° C. is in the range of from 20 to 100% of total gemcitabine. In some embodiments, the percentage nucleoside analogue (e.g. gemcitabine) released from the dendrimer in PBS at pH 7.4 and at 37° C. is in the range of from 40 to 80%. In some embodiments, the percentage nucleoside analogue (e.g. gemcitabine) released from the dendrimer in PBS at pH 7.4 and at 37° C. is in the range of from 40 to 60%. In some embodiments, the percentage nucleoside analogue (e.g. gemcitabine) released from the dendrimer in PBS at pH 7.4 and at 37° C. is in the range of from 70 to 90%.

In some embodiments, the in vitro half-life for nucleoside analogue (e.g. gemcitabine) release from the dendrimer in citrate buffer (0.1 M, pH 4.5) at 37° C. is in the range of from 1 to 20 days. In some embodiments, the in vitro half-life for nucleoside analogue (e.g. gemcitabine) release from the dendrimer in citrate buffer (0.1 M, pH 4.5) at 37° C. is in the range of from 5 to 10 days. In some embodiments, the in vitro half-life for nucleoside analogue (e.g. gemcitabine) release from the dendrimer in citrate buffer (0.1 M, pH 4.5) at 37° C. is in the range of from 8 to 15 days. In some embodiments, the in vitro half-life for nucleoside analogue (e.g. gemcitabine) release from the dendrimer in citrate buffer (0.1 M, pH 4.5) at 37° C. is in the range of from 10 to 20 days.

In some embodiments, the percentage nucleoside analogue (e.g. gemcitabine) released from the dendrimer after 24 hours in citrate buffer (0.1 M, pH 4.5) at 37° C. is in the range of from 1 to 30% of total gemcitabine. In some embodiments, the percentage nucleoside analogue (e.g. gemcitabine) released from the dendrimer in citrate buffer (0.1 M, pH 4.5) at 37° C. is in the range of from 1 to 20%. In some embodiments, the percentage nucleoside analogue (e.g. gemcitabine) released from the dendrimer in citrate buffer (0.1 M, pH 4.5) at 37° C. is in the range of from 10 to 20%. In some embodiments, the percentage nucleoside analogue (e.g. gemcitabine) released from the dendrimer in citrate buffer (0.1 M, pH 4.5) at 37° C. is in the range of from 1 to 5%.

In some embodiments, the dendrimer is any one of the dendrimers described in the Examples below (excluding any comparative Examples).

Compositions

In some embodiments, the dendrimer is presented as a composition, preferably a pharmaceutical composition.

It will be appreciated that there may be some variation in the molecular composition between the dendrimers present in a given composition, as a result of the nature of the synthetic process for producing the dendrimers. For example, as discussed above one or more synthetic steps used to produce a dendrimer may not proceed fully to completion, which may result in the presence of dendrimers which do not all comprise the same number of first terminal groups or second terminal groups, or which contain incomplete generations of building units.

Accordingly, there is provided a composition comprising a plurality of dendrimers or pharmaceutically acceptable salts thereof, wherein the dendrimers are as defined herein, the mean number of first terminal groups per dendrimer in the composition is in the range of from 24 to 32, and the mean number of second terminal groups per dendrimer in the composition is in the range of from 24 to 32.

In some embodiments, the mean number of first terminal groups per dendrimer is in the range of from 28 to 32, and wherein the mean number of second terminal groups per dendrimer is in the range of from 28 to 32. In some embodiments, the mean number of first terminal groups per dendrimer is in the range of from 29 to 32, and wherein the mean number of second terminal groups per dendrimer is in the range of from 29 to 32. In some embodiments, the mean number of first terminal groups per dendrimer is in the range of from 30 to 32, and wherein the mean number of second terminal groups per dendrimer is in the range of from 30 to 32. In some embodiments, the composition is a pharmaceutical composition, and the composition comprises a pharmaceutically acceptable excipient.

In some embodiments, at least 50%, at least 60%, at least 70%, at least 80%, at least 90%, or at least 95% of the dendrimers contain at least 24 first terminal groups. In some embodiments, at least 50%, at least 60%, at least 70%, at least 80%, at least 90%, or at least 95% of the dendrimers contain at least 26 first terminal groups. In some embodiments, at least 50%, at least 60%, at least 70%, at least 80%, at least 90%, or at least 95% of the dendrimers contain at least 28 first terminal groups.

In some embodiments, at least 50%, at least 60%, at least 70%, at least 80%, at least 90%, or at least 95% of the dendrimers contain at least 28 second terminal groups. In some embodiments, at least 50%, at least 60%, at least 70%, at least 80%, at least 90%, or at least 95% of the dendrimers contain at least 29 second terminal groups.

In some embodiments, at least 50%, at least 60%, at least 70%, at least 80%, at least 90%, or at least 95% of the dendrimers contain at least 24 first terminal groups and at least 28 second terminal groups. In some embodiments, at least 50%, at least 60%, at least 70%, at least 80%, at least 90%, or at least 95% of the dendrimers contain at least 26 first terminal groups and at least 29 second terminal groups.

The present disclosure also provides pharmaceutical compositions, both for veterinary and for human medical use, which comprise the dendrimers of the present disclosure or a pharmaceutically acceptable salt thereof, with one or more pharmaceutically acceptable carriers, and optionally any other therapeutic ingredients, stabilisers, or the like. The carrier(s) must be pharmaceutically acceptable in the sense of being compatible with the other ingredients of the formulation and not unduly deleterious to the recipient thereof. In some embodiments, the composition is a pharmaceutical composition, and wherein the composition comprises a pharmaceutically acceptable excipient.

The composition may for example contain a solvent, such as water (e.g. water for injection) or a pharmaceutically acceptable organic solvent.

The compositions may further include diluents, buffers, citrate, trehalose, binders, disintegrants, thickeners, lubricants, preservatives (including antioxidants), inorganic salts (e.g., sodium chloride), antimicrobial agents (e.g., benzalkonium chloride), sweeteners, antistatic agents, sorbitan esters, lipids (e.g., phospholipids such as lecithin and other phosphatidylcholines, phosphatidylethanolamines, fatty acids and fatty esters, steroids (e.g., cholesterol)), and chelating agents (e.g., EDTA, zinc and other such suitable cations).

The compositions of the present disclosure may also include polymeric excipients/additives or carriers, e.g., polyvinylpyrrolidones, derivatised celluloses such as hydroxymethylcellulose, hydroxyethylcellulose, and hydroxypropylmethylcellulose, Ficolls (a polymeric sugar), hydroxyethylstarch (HES), dextrates (e.g., cyclodextrins, such as 2-hydroxypropyl-β-cyclodextrin and sulfobutylether-β-cyclodextrin), polyethylene glycols, and pectin.

Other pharmaceutical excipients and/or additives suitable for use in the compositions according to the present disclosure are listed in "Remington: The Science & Practice of Pharmacy", 19.sup.th ed., Williams & Williams, (1995), and in the "Physician's Desk Reference", 52.sup.nd ed., Medical Economics, Montvale, N.J. (1998), and in "Handbook of Pharmaceutical Excipients", Third Ed., Ed. A. H. Kibbe, Pharmaceutical Press, 2000.

The dendrimers of the present disclosure may be formulated in compositions including those suitable for inhalation to the lung, by aerosol, or parenteral (including intraperitoneal, intravenous, subcutaneous, or intramuscular injection) administration.

The compositions may conveniently be presented in unit dosage form and may be prepared by any of the methods well known in the art of pharmacy. All methods include the step of bringing the dendrimer into association with a carrier that constitutes one or more accessory ingredients.

In general, the compositions are prepared by bringing the dendrimer into association with a liquid carrier to form a solution or a suspension, or alternatively, bring the dendrimer into association with formulation components suitable for forming a solid, optionally a particulate product, and then, if warranted, shaping the product into a desired delivery form.

Solid formulations of the present disclosure, when particulate, will typically comprise particles with sizes ranging from about 1 nanometer to about 500 microns. In general, for solid formulations intended for intravenous administration, particles will typically range from about 1 nm to about 10 microns in diameter. The composition may contain dendrimer of the present disclosure that are nanoparticulate having a particulate diameter of below 1000 nm, for example, between 5 and 1000 nm, especially 5 and 500 nm, more especially 5 to 400 nm, such as 5 to 50 nm and especially between 5 and 20 nm. In one example, the composition contains dendrimers with a mean size of between 5 and 20 nm. In some embodiments, the dendrimer is polydispersed in the composition, with PDI of between 1.01 and 1.8, especially between 1.01 and 1.5, and more especially between 1.01 and 1.2. In one example, the dendrimer is monodispersed in the composition.

In some preferred embodiments, the composition is formulated for parenteral delivery. In some embodiments, the composition is formulated for intravenous delivery. For example, in one embodiment, the formulation may be a sterile, lyophilized composition that is suitable for reconstitution in an aqueous vehicle prior to injection.

In one embodiment, a composition suitable for parenteral administration conveniently comprises a sterile aqueous preparation of the dendrimer, which may for example be formulated to be isotonic with the blood of the recipient.

Pharmaceutical compositions are also provided which are suitable for administration as an aerosol, by inhalation. These formulations comprise a solution or suspension of the desired dendrimer or a salt thereof. The desired formulation may be placed in a small chamber and nebulized. Nebulization may be accomplished by compressed air or by ultrasonic energy to form a plurality of liquid droplets or solid particles comprising the dendrimers or salts thereof.

As discussed below, the dendrimers of the present disclosure may for example be administered in combination with one or more additional pharmaceutically active agents. Thus, in some embodiments, the composition comprises a dendrimer as defined herein, or a pharmaceutically acceptable salt thereof, one or more pharmaceutically acceptable carriers, and one or more additional pharmaceutically active agents, e.g. an additional oncology agent or oncology drug. In some embodiments, the additional active ingredient is an anti-cancer agent for therapy of prostate cancer or breast cancer.

In some embodiments, the additional pharmaceutically active agent is a chemotherapeutic agent, a cytotoxic agent, or an antibody therapy. In some embodiments, the additional pharmaceutically active agent is a MAPK/ERK signalling pathway inhibitor.

In some embodiments, the additional pharmaceutically active agent is a further anticancer agent. Examples of further anticancer agents include, but are not limited to, platinum-containing pharmaceutical agents, taxanes, immunooncology agents, PARP inhibitors, topoisomerase I inhibitors, antibodies, antifolates, tyrosine kinase inhibitors, anthracyclines, and vinca alkaloids.

In some embodiments, the anticancer agent is selected from the group consisting of capecitabine, Nab-paclitaxel (e.g. Abraxane®), docetaxel, cabazitaxel, doxorubicin, vindesine, irinotecan, folinic acid, 5-fluorouracil, methotrexate, pemetrexed, lapatinib, nintedanib, sunitinib, olaparib, niraparib, carboplatin, paclitaxel, SN38, cisplatin, oxaliplatin, paclitaxel, erlotinib, and irinotecan.

Further examples of additional pharmaceutically active agents include anti-CD20 agents, for example, antibodies such as rituximab (Rituxan®).

Further examples of additional pharmaceutically active agents include immunooncology agents, for example, PD-1 inhibitors, PD-L1 inhibitors, or CTLA4 inhibitors, such as pembrolizumab (Keytruda®), nivolumab (Opdivo®), durvalumab (Imfinzi®), atezolizumab (Tecentriq®), avelumab (Bavencio®), and ipilimumab (Yervoy®).

In some embodiments, the composition is formulated for parenteral infusion as part of a chemotherapy regimen.

Methods of Use

The dendrimers of the present disclosure may be used to treat or prevent any disease, disorder or symptom that the unmodified pharmaceutically active agent can be used to treat or prevent. Accordingly, there is also provided a dendrimer or pharmaceutical composition as described herein for use in therapy.

In some embodiments, the dendrimer, or pharmaceutical composition comprising the dendrimer, is used in a method of treating or preventing cancer, for example for suppressing the growth of a tumour. In some embodiments the dendrimer is for use in the treatment of cancer. There is also provided a method of treating cancer comprising administering to a subject in need thereof a therapeutically effective amount of the dendrimer, or of a pharmaceutical composition comprising the dendrimer. There is also provided use of a dendrimer as defined herein, or of a composition as defined herein, in the manufacture of a medicament for the treatment of cancer.

In some embodiments, the cancer is a solid tumour. The cancer may be a primary or metastatic tumour. In some embodiments the cancer is a primary tumour. In some embodiments the cancer is a metastatic tumour.

In some embodiments, the cancer, is selected from the group consisting of breast cancer, ovarian cancer, non-small cell lung cancer, pancreatic cancer, bladder cancer, upper gastrointestinal cancer, oesophageal cancer, stomach cancer, small bowel cancer, liver cancer, cancer of the biliary system, sarcoma, ovarian cancer, gall bladder cancer, biliary tract cancer, prostate and nasopharyngeal cancer. In some embodiments, the cancer is breast cancer. In some embodiments, the cancer is ovarian cancer. In some embodiments, the cancer is non-small cell lung cancer. In some embodiments, the cancer is pancreatic cancer. In some embodiments, the cancer is bladder cancer. In some embodiments, the cancer is upper gastrointestinal cancer. In some embodiments, the cancer is oesophageal cancer. In some embodiments, the cancer is stomach cancer. In some embodiments, the cancer is small bowel cancer. In some embodiments, the cancer is liver cancer. In some embodiments, the cancer is cancer of the biliary system. In some embodiments, the cancer is sarcoma. In some embodiments, the cancer is ovarian cancer. In some embodiments, the cancer is gall bladder cancer. In some embodiments, the cancer is biliary tract cancer. In some embodiments, the cancer is nasopharyngeal cancer.

Combinations

Drugs are often co-administered with other drugs in combination therapy, especially during chemotherapy. Accordingly, in some embodiments the dendrimer is administered in combination with one or more further pharmaceutically active agents, for example one or more further anti-cancer agents/oncology agents. The dendrimer and the one or more further pharmaceutically active agents may be administered simultaneously, subsequently or separately. For example, they may be administered as part of the same composition, or by administration of separate compositions. The one or more further pharmaceutically active agents may for example be anti-cancer agents for therapy of prostate cancer or breast cancer. Examples of further pharmaceutically active agents include, but are not limited to, chemotherapeutic and cytotoxic agents, antibody therapies, and MAPK/ERK signalling pathway inhibitors.

Examples of further pharmaceutically active agents include, but are not limited to, platinum-containing pharmaceutical agents, taxanes, immunooncology agents, PARP inhibitors, topoisomerase I inhibitors, antibodies, antifolates, tyrosine kinase inhibitors, anthracyclines, and vinca alkaloids.

In some embodiments, the dendrimer is administered in combination with a further anticancer agent selected from the group consisting of capecitabine, Nab-paclitaxel (e.g.

Abraxane®), docetaxel, cabazitaxel, doxorubicin, vindesine, irinotecan, folinic acid, 5-fluorouracil, methotrexate, pemetrexed, lapatinib, nintedanib, sunitinib, olaparib, niraparib, carboplatin, paclitaxel, SN38, cisplatin, oxaliplatin, paclitaxel, erlotinib, and irinotecan.

In some embodiments, the further pharmaceutically active agent is an anti-CD20 agent, for example, an antibody such as rituximab (Rituxan®).

In some embodiments, the further pharmaceutically active agent is an immunooncology agent, for example, a PD-1 inhibitor, PD-L1 inhibitor, or CTLA4 inhibitor, such as pembrolizumab (Keytruda®), nivolumab (Opdivo®), durvalumab (Imfinzi®), atezolizumab (Tecentriq®), avelumab (Bavencio®), and ipilimumab (Yervoy®).

Dendrimer Combinations

As demonstrated by the examples, the dendrimers of the present disclosure are effective when administered in combination with an oncology drug-containing dendrimer (e.g., taxane-containing dendrimer). Thus, in some embodiments, the dendrimer is administered in combination with a second dendrimer, which second dendrimer comprises:

i) a core unit (C); and ii) building units (BU), each building unit being a lysine residue or an analogue thereof;

wherein the core unit is covalently attached to two building units via amide linkages, each amide linkage being formed between a nitrogen atom present in the core unit and the carbon atom of an acyl group present in a building unit;

the dendrimer being a five generation building unit dendrimer;

wherein building units of different generations are covalently attached to one another via amide linkages formed between a nitrogen atom present in one building unit and the carbon atom of an acyl group present in another building unit;

the dendrimer further comprising:

iii) a plurality of first terminal groups (T1) each comprising a residue of an oncology agent having a hydroxyl group, covalently attached to a diacyl linker group of formula:

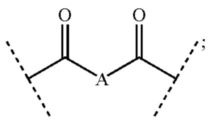

wherein A is a $C_2$-$C_{10}$ alkylene group which is interrupted by at least one O, S, NH, or N(Me), or in which A is a heterocycle selected from the group consisting of tetrahydrofuran, tetrahydrothiophene, pyrrolidine, and N-methylpyrrolidine; and iv) a plurality of second terminal groups (T2) each comprising a hydrophilic polymeric group;

or a pharmaceutically acceptable salt thereof.

The core unit (C) of the second dendrimer is as described above for the first dendrimer.

The building units (BU) of the second dendrimer are as described above for the first dendrimer.

The diacyl linker of the second dendrimer is as described above for the first dendrimer.

The second terminal group of the second dendrimer is as described above for the first dendrimer.

In some embodiments, the oncology agent is a taxane.

Taxane-containing dendrimers are described in, for example, WO2012/167309, US2018/0326081 and WO2020/014750A1, the contents of which are incorporated herein by reference.

The taxane of the second dendrimer may be selected from any taxane that exhibits chemotherapeutic activity. In some embodiments, the taxane is selected from the group consisting of docetaxel, paclitaxel, and cabazitaxel. In some embodiments, the taxane is docetaxel. In some embodiments, the taxane is paclitaxel. In some embodiments, the taxane is cabazitaxel.

The taxane may be covalently attached to a diglycolyl or thiodiglycolyl linker via an ester linkage formed between an oxygen atom present as part of the taxane and a carbon atom of an acyl group present as part of the linker.

In some embodiments, the second dendrimer comprises:

i) a core unit (C); and ii) building units (BU), each building unit being a lysine residue;

wherein the core unit is covalently attached to two building units via amide linkages, each amide linkage being formed between a nitrogen atom present in the core unit and the carbon atom of an acyl group present in a building unit;

the dendrimer being a five generation building unit dendrimer;

wherein building units of different generations are covalently attached to one another via amide linkages formed between a nitrogen atom present in one building unit and the carbon atom of an acyl group present in another building unit;

the dendrimer further comprising:

iii) a plurality of first terminal groups (T1) each comprising a residue of docetaxel, which docetaxel has a hydroxyl group, covalently attached to a diacyl linker group of formula:

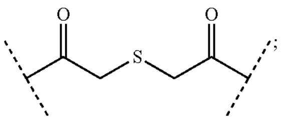

and iv) a plurality of second terminal groups (T2) each comprising a PEG;

or a pharmaceutically acceptable salt thereof.

In some embodiments, the second dendrimer comprises:

i) a core unit (C); and ii) building units (BU), each building unit being a lysine residue;

wherein the core unit is covalently attached to two building units via amide linkages, each amide linkage being formed between a nitrogen atom present in the core unit and the carbon atom of an acyl group present in a building unit;

the dendrimer being a five generation building unit dendrimer;

wherein building units of different generations are covalently attached to one another via amide linkages formed between a nitrogen atom present in one building unit and the carbon atom of an acyl group present in another building unit;

the dendrimer further comprising:

iii) a plurality of first terminal groups (T1) each comprising a residue of docetaxel, which docetaxel has a hydroxyl group, covalently attached to a diacyl linker group of formula:

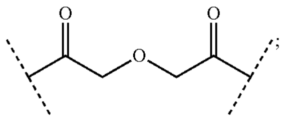

and iv) a plurality of second terminal groups (T2) each comprising a PEG;

or a pharmaceutically acceptable salt thereof.

In some embodiments, the second dendrimer comprises:

i) a core unit (C); and ii) building units (BU), each building unit being a lysine residue;

wherein the core unit is covalently attached to two building units via amide linkages, each amide linkage being formed between a nitrogen atom present in the core unit and the carbon atom of an acyl group present in a building unit;

the dendrimer being a five generation building unit dendrimer;

wherein building units of different generations are covalently attached to one another via amide linkages formed between a nitrogen atom present in one building unit and the carbon atom of an acyl group present in another building unit;

the dendrimer further comprising:

iii) a plurality of first terminal groups (T1) each comprising a residue of cabazitaxel, which cabazitaxel has a hydroxyl group, covalently attached to a diacyl linker group of formula:

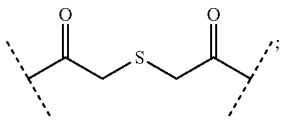

and iv) a plurality of second terminal groups (T2) each comprising a PEG;

or a pharmaceutically acceptable salt thereof.

In some embodiments, the second dendrimer comprises:

i) a core unit (C); and ii) building units (BU), each building unit being a lysine residue;

wherein the core unit is covalently attached to two building units via amide linkages, each amide linkage being formed between a nitrogen atom present in the core unit and the carbon atom of an acyl group present in a building unit;

the dendrimer being a five generation building unit dendrimer;

wherein building units of different generations are covalently attached to one another via amide linkages formed between a nitrogen atom present in one building unit and the carbon atom of an acyl group present in another building unit;

the dendrimer further comprising:

iii) a plurality of first terminal groups (T1) each comprising a residue of cabazitaxel, which cabazitaxel has a hydroxyl group, covalently attached to a diacyl linker group of formula:

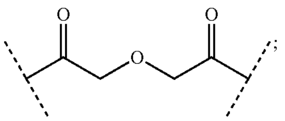

and iv) a plurality of second terminal groups (T2) each comprising a PEG;

or a pharmaceutically acceptable salt thereof.

In some embodiments, the oncology agent is a topoisomerase I inhibitor, for example, a camptothecin active.

Camptothecin active-containing dendrimers are described in, for example, WO2020/102852A1, the contents of which are incorporated herein by reference.

In some embodiments, the topoisomerase I inhibitor is a camptothecin active, for example, SN38.

The camptothecin active (e.g., SN38) may, for example, be covalently attached to a diglycolyl or thiodiglycolyl linker via an ester linkage formed between an oxygen atom present as part of the camptothecin active and a carbon atom of an acyl group present as part of the linker.

In some embodiments, the second dendrimer comprises:

i) a core unit (C); and ii) building units (BU), each building unit being a lysine residue;

wherein the core unit is covalently attached to two building units via amide linkages, each amide linkage being formed between a nitrogen atom present in the core unit and the carbon atom of an acyl group present in a building unit;

the dendrimer being a five generation building unit dendrimer;

wherein building units of different generations are covalently attached to one another via amide linkages formed between a nitrogen atom present in one building unit and the carbon atom of an acyl group present in another building unit;

the dendrimer further comprising:

iii) a plurality of first terminal groups (T1) each comprising a residue of SN38, which SN38 has a hydroxyl group, covalently attached to a diacyl linker group of formula:

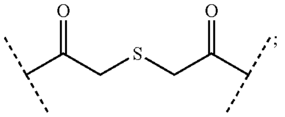

and iv) a plurality of second terminal groups (T2) each comprising a PEG;

or a pharmaceutically acceptable salt thereof.

In some embodiments, the second dendrimer comprises:

i) a core unit (C); and ii) building units (BU), each building unit being a lysine residue;

wherein the core unit is covalently attached to two building units via amide linkages, each amide linkage being formed between a nitrogen atom present in the core unit and the carbon atom of an acyl group present in a building unit;

the dendrimer being a five generation building unit dendrimer;

wherein building units of different generations are covalently attached to one another via amide linkages formed between a nitrogen atom present in one building unit and the carbon atom of an acyl group present in another building unit;

the dendrimer further comprising:

iii) a plurality of first terminal groups (T1) each comprising a residue of a camptothecin active (e.g., SN38), which camptothecin active has a hydroxyl group, covalently attached to a diacyl linker group of formula:

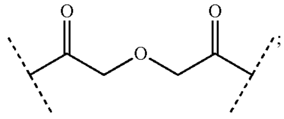

;

and iv) a plurality of second terminal groups (T2) each comprising a PEG;

or a pharmaceutically acceptable salt thereof.

Accordingly, in some embodiments, there is provided the methods, uses, or compositions for use as described herein, wherein the dendrimer is administered in combination with a second dendrimer, as described above.

Dose

It will be appreciated that a therapeutically effective amount refers to a dendrimer being administered in an amount sufficient to alleviate or prevent to some extent one or more of the symptoms of the disorder or condition being treated. A therapeutically effective amount of dendrimer may be referred to based on, for example, the amount of dendrimer administered. Alternatively, it may be determined based on the amount of nucleoside analogue active (e.g. gemcitabine) which the dendrimer is theoretically capable of delivering, e.g. based on the loading of nucleoside analogue active on the dendrimer.

That is, a therapeutically effective amount of dendrimer-drug conjugate may be referred to on the basis of, for example, the amount of dendrimer-drug conjugate administered. Alternatively, it may be determined based on the amount of active agent (drug moiety comprising gemcitabine nucleoside) which the dendrimer-drug conjugate is theoretically capable of delivering, e.g. based on the loading of drug moiety on the dendrimer.

As used herein, the terms "unconjugated" and "released" refer to a drug moiety which has dissociated or been cleaved from a dendrimer. This dissociation or cleaving may occur in vivo following administration of the drug-dendrimer conjugate.

The dendrimer may be administered by any suitable route. The route of administration may for example be targeted to the disease or disorder which the subject has. The subject is typically a human, although it will be understood that the dendrimer can also be used to treat conditions in non-human animals.

In some embodiments, the dendrimer is administered intravenously. Gemcitabine itself is typically administered as an IV infusion over a 30 minute period. In some embodiments, the dendrimer is delivered as an IV bolus. In some embodiments the dendrimer is administered IV over a time a period in the range of from 0.5 to 15 minutes, or in the range of from 0.5 to 5 minutes.

In some embodiments, the dendrimer may be administered intraperitoneally. For example, the disease or disorder may be an intra-abdominal malignancy such as a gynecological or gastrointestinal cancer, and the dendrimer may be administered intraperitoneally. In some embodiments the dendrimer may be for treatment of a cancer of the peritoneal cavity, such as a malignant epithelial tumor (e.g., ovarian cancer) or peritoneal carcinomatosis (eg gastrointestinal especially colorectal, gastric, gynecologic cancers, and primary peritoneal neoplasms), and the dendrimer is administered intraperitoneally.

Gemcitabine itself is typically administered at 7-day intervals, e.g., on days 1 and 8, or days 1, 8, and 15 of a dosing cycle, or once weekly.

In some embodiments, the dendrimers are administered in at least 10-day dosing intervals, at least 14-day dosing intervals, at least 21-day dosing intervals, or at least 28-day dosing intervals.

When a dose of gemcitabine is administered to a patient, a typical dose is 1000 $mg/m^2$ or 1250 $mg/m^2$.

In some embodiments, the amount of dendrimer administered is sufficient to deliver an amount of released active agent in the range of from 1 to 1500 mg of nucleoside analogue (e.g. gemcitabine)/$m^2$, in the range of from 1 to 1250 mg of nucleoside analogue (e.g. gemcitabine)/$m^2$, in the range of from 1 to 500 mg, in the range of from 1 to 400 mg, in the range of from 1 to 300 mg, in the range of from 5 to 200 mg, in the range of from 500 to 1250 mg of nucleoside analogue (e.g. gemcitabine)/$m^2$, in the range of from 2 to 1000 mg of nucleoside analogue (e.g. gemcitabine)/$m^2$, in the range of from 5 to 500 mg of nucleoside analogue (e.g. gemcitabine)/$m^2$, in the range of from 5 to 100 mg of nucleoside analogue (e.g. gemcitabine)/$m^2$, in the range of from 20 to 500 mg of nucleoside analogue (e.g. gemcitabine)/$m^2$, in the range of from 20 to 200 mg of nucleoside analogue (e.g. gemcitabine)/$m^2$, in the range of from 50 to 200 mg of nucleoside analogue (e.g. gemcitabine)/$m^2$, in the range of from 50 to 100 mg of nucleoside analogue (e.g. gemcitabine)/$m^2$, in the range of from 75 to 125 mg of nucleoside analogue (e.g. gemcitabine)/$m^2$, or in the range of from 50 to 75 mg of nucleoside analogue (e.g. gemcitabine)/$m^2$.

In some embodiments, a therapeutically effective amount of the dendrimer is administered to a subject in need thereof at a predetermined frequency. In some embodiments, the dendrimer is administered to a subject in need thereof according to a dosage regimen in which the dendrimer is administered once per one to four weeks. In some embodiments, the dendrimer is administered to a subject in need thereof according to a dosage regimen in which the dendrimer is administered once per three to four weeks.

In some embodiments, the dendrimer or pharmaceutical composition is administered as a fast infusion or as a bolus. In some embodiments, the infusion time is less than 1 hour, less than 30 minutes or less than 20 minutes, or the infusion time is 20 minutes, 15 minutes or 10 minutes. In some embodiments, the administration may be as a bolus, for example, in 5 seconds to 5 minutes.

The use of the dendrimers of the present disclosure may provide for controlled release of drug moiety comprising a residue of a nucleoside analogue in vivo, and may allow for administration of a large quantity of conjugated drug moiety in a single dose, which is then released gradually over time.

In some embodiments, the dendrimer will provide therapeutic levels of the residue of a nucleoside analogue for prolonged periods, and so can be administered less frequently than the free nucleoside analogues. For example, the dendrimer may be administered once every two days, or once every three days, or once every seven days, or once every ten days, or once every two weeks, or once every three weeks, or one every four weeks, or once per month. In some embodiments, a single dose of dendrimer provides a therapeutically effective amount of the drug moiety comprising a residue of a nucleoside analogue over a period of at least 6 hours, at least 12 hours, at least 24 hours, at least two days, at least three days, at least four days, at least five days, at least six days, at least seven days. In some embodiments, a single dose of dendrimer provides a therapeutically effective amount of a residue of a nucleoside analogue over a period of about one day, about two days, about three days, about four days, about five days, about six days, about seven days, about eight days, about nine days, about ten days, or about 14 days.

In some embodiments, when exposed to PBS at pH 7.4 and 37° C., the dendrimer releases between about 5% and 90%, between about 10% and about 90%, between about 5% and 80%, between about 10% and 80%, between about 20% and 80%, between about 20% and 70%, or between about 30 and 60% of the residue of the nucleoside analogue after 24 hours. In some embodiments, when exposed to PBS at pH 7.4 and 37° C., the dendrimer releases at least about 5%, at least about 10%, at least about 20%, at least about 30%, at least about 40%, at least about 50%, at least about 60%, at least about 70%, at least about 80%, or at least about 90% of the residue of the nucleoside analogue after 24 hours.

In some embodiments, when exposed to 1% citrate buffer at pH 4.5 and 37° C., the dendrimer releases between about 5% and 30%, between about 5% and 25%, between about 5% and 20%, between about 5% and 10%, of the residue of the nucleoside analogue after 24 hours. In some embodiments, when exposed to 1% citrate buffer at pH 4.5 and 37° C., the dendrimer releases less than about 5%, less than about 10%, less than about 20%, less than about 30%, of the residue of the nucleoside analogue after 24 hours.

Pharmacokinetics, Efficacy and Side Effects

It has been surprisingly found that the dendrimers of the present disclosure provide for good therapeutic and pharmacokinetic properties in vivo.

As used herein, the term "free" refers to a drug, e.g., gemcitabine, which has not been previously conjugated to a dendrimer. For example, the direct administration of free gemcitabine refers to the direct administration of gemcitabine molecules that are not administered as being conjugated to a dendrimer. An example of such a therapy is Gemzar®.

As used herein, the terms "unconjugated" and "released" refer to a drug, e.g. gemcitabine, which has dissociated or been cleaved from a dendrimer. This dissociation or cleaving may occur in vivo following administration of the drug-dendrimer conjugate. Comparisons may for example be made following administration of a dendrimer comprising gemcitabine as the nucleoside analogue, and following administration of an equivalent amount of unconjugated drug (e.g., of Gemzar®).

The term "equivalent amount" or "equivalent dose" in this context refers to administration of a dose of dendrimer which, if all nucleoside analogue present as part of the dendrimer were released, would provide the same number of moles of nucleoside analogue active as in a dose of unconjugated drug being administered.

In some embodiments, administration of the dendrimer provides enhanced clinical efficacy in comparison to administration of an equivalent dose of free nucleoside analogue (e.g. gemcitabine). Enhanced clinical efficacy may include any one or more of the following: improved survival rate, reduced mortality rate, improved life expectancy, and slower progression rate of cancer.

In some embodiments, the dendrimers of the present disclosure provide a lower maximal concentration (Cmax), increased duration of therapeutically effective plasma concentration of nucleoside analogue (e.g. gemcitabine), and/or reduced toxicity, in comparison to administration of an equivalent amount of the unconjugated drug.

In some embodiments, administration of the dendrimer provides a lower maximal concentration (Cmax) of nucleoside analogue (e.g., gemcitabine), in comparison to administration of an equivalent amount of the unconjugated drug. In some embodiments, the Cmax of nucleoside analogue (e.g., gemcitabine) achieved following administration of the dendrimer is less than 50%, less than 40%, less than 30%, less than 20%, less than 10%, less than 5%, or less than 2% of the Cmax achieved following administration of an equivalent amount of the unconjugated drug.

In some embodiments, administration of the dendrimer provides therapeutically effective plasma concentration levels of nucleoside analogue (e.g., gemcitabine) for an extended period of time following administration, in comparison to administration of an equivalent dose of free gemcitabine. In some embodiments, administration of the dendrimer provides therapeutically effective plasma concentration levels of nucleoside analogue (e.g., gemcitabine) for at least twice as long, or at least three times as long, or at least four times as long, or at least five times as long as the period of time over which therapeutically effective plasma concentrations of nucleoside analogue are achieved following administration of an equivalent dose of free nucleoside analogue.

Oncology drugs often have significant side effects that are due to off-target toxicity. In the case of nucleoside analogues such as gemcitabine, known side effects include pulmonary toxicity and respiratory failure, haemolytic uremic syndrome, renal impairment, severe hepatic toxicity, capillary leak syndrome, and posterior reversible encephalopathy syndrome.

The toxicity of a drug refers to the degree to which damage is caused to the organism, and is measured by its effect off target. In oncology, one such measurement of toxicity in animal models is weight loss, which determines the maximum tolerated dose (MTD). In humans toxicity is commonly determined by specified adverse events (AE), which typically identify the dose limiting toxicity. It will be appreciated that usually in oncology, there is a narrow therapeutic window and off-target toxicities are considered a normal side effect of killing tumour cells. In some embodiments, administration of the dendrimer provides reduced toxicity and/or side effects in comparison to administration of an equivalent dose of free nucleoside analogue (e.g. gemcitabine).

Dendrimer Synthesis

The dendrimers of the present disclosure may be prepared by any suitable method, for example, by reacting a nucleoside analogue-containing precursor with a dendrimeric intermediate already containing a PEG group to introduce the pharmaceutically active agent; by reacting a PEG-containing precursor with a dendrimeric intermediate already containing a nucleoside analogue residue; or by reacting an intermediate comprising the residue of a lysine group, a nucleoside analogue residue, and a PEG group, with a dendrimeric intermediate. Accordingly, there is provided a process for producing a dendrimer as defined herein, comprising:

a) reacting a nucleoside analogue intermediate which is:

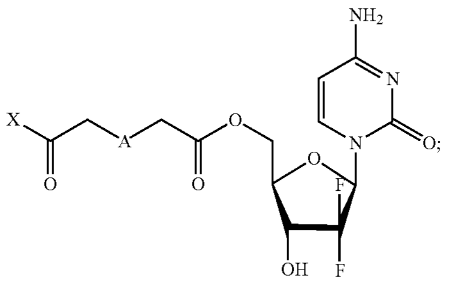

wherein A is O or S, X is —OH or a leaving group (e.g. an active ester), or wherein X together with the C(O) group to which it is attached forms a carboxylate salt;

with a dendrimeric intermediate which comprises:

i) a core unit (C); and ii) building units (BU), each building unit being a lysine residue or an analogue thereof;

wherein the core unit is covalently attached to two building units via amide linkages, each amide linkage being formed between a nitrogen atom present in the core unit and the carbon atom of an acyl group present in a building unit;

the dendrimer being a five generation building unit dendrimer;

wherein building units of different generations are covalently attached to one another via amide linkages formed between a nitrogen atom present in one building unit and the carbon atom of an acyl group present in another building unit;

the dendrimer further comprising:

a plurality of second terminal groups (T2) each comprising a hydrophilic polymeric group (e.g. a PEG, PEOX or polysarcosine group);

or a salt thereof;

under amide coupling conditions;

or b) reacting a PEG intermediate which is:

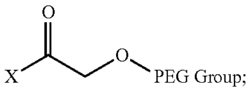

wherein PEG Group is a PEG-containing group, and

X is —OH or a leaving group (e.g. active ester), or wherein X together with the C(O) group to which it is attached forms a carboxylate salt;

with a dendrimeric intermediate which comprises:

i) a core unit (C); and ii) building units (BU), each building unit being a lysine residue or an analogue thereof;

wherein the core unit is covalently attached to two building units via amide linkages, each amide linkage being formed between a nitrogen atom present in the core unit and the carbon atom of an acyl group present in a building unit;

the dendrimer being a five generation building unit dendrimer;

wherein building units of different generations are covalently attached to one another via amide linkages formed between a nitrogen atom present in one building unit and the carbon atom of an acyl group present in another building unit;

the dendrimer further comprising:

a plurality of first terminal groups (T1) each comprising a nucleoside analogue residue covalently attached to a linker group of formula

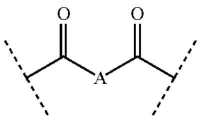

wherein A is $—CH_2OCH_2—$ or $—CH_2SCH_2—$;

or a salt thereof;

under amide coupling conditions;

or c) reacting a surface unit intermediate which is:

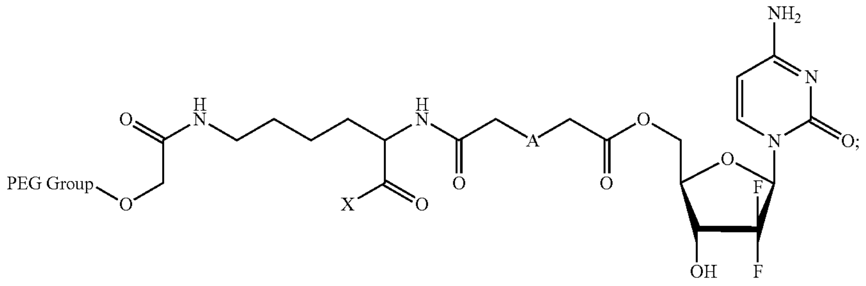

wherein PEG Group is a PEG-containing group, A is O or S, and

X is —OH or a leaving group (e.g. an active ester), or wherein X together with the C(O) group to which it is attached forms a carboxylate salt;

with a dendrimeric intermediate comprising:

i) a core unit (C); and ii) building units (BU), each building unit being a lysine residue or an analogue thereof;

wherein the core unit is covalently attached to two building units via amide linkages, each amide linkage being formed between a nitrogen atom present in the core unit and the carbon atom of an acyl group present in a building unit;

the dendrimeric intermediate being a four generation building unit dendrimeric intermediate;

wherein building units of different generations are covalently attached to one another via amide linkages formed between a nitrogen atom present in one building unit and the carbon atom of an acyl group present in another building unit;

and wherein nitrogen atoms present in the outer building units of the dendrimeric intermediate are unsubstituted;

or a salt thereof;

under amide coupling conditions;

or d) reacting a nucleoside analogue intermediate which is:

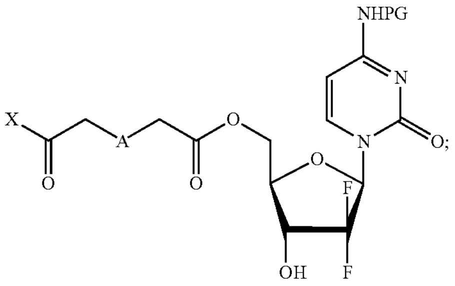

wherein A is O or S, PG is an amine protecting group, X is —OH or a leaving group (e.g. an active ester), or wherein X together with the C(O) group to which it is attached forms a carboxylate salt;

with a dendrimeric intermediate which comprises:

i) a core unit (C); and ii) building units (BU), each building unit being a lysine residue or an analogue thereof;

wherein the core unit is covalently attached to two building units via amide linkages, each amide linkage being formed between a nitrogen atom present in the core unit and the carbon atom of an acyl group present in a building unit;

the dendrimer being a five generation building unit dendrimer;

wherein building units of different generations are covalently attached to one another via amide linkages formed between a nitrogen atom present in one building unit and the carbon atom of an acyl group present in another building unit;

the dendrimer further comprising:

a plurality of second terminal groups (T2) each comprising a hydrophilic polymeric group (e.g. a PEG, PEOX or polysarcosine group);

or a salt thereof;

under amide coupling conditions; and deprotecting PG to form the product as a salt; and optionally converting the product from the salt to another salt or to the free base.

Process variants a), b), c), and d) involve formation of amide bonds by reaction of —C(O)X groups with amine groups present in the dendrimeric intermediates. Any suitable amide formation conditions, also referred to as amide coupling conditions, may be used. Examples of typical conditions include the use of a suitable solvent (for example dimethylformamide) optionally a suitable base, and at a suitable temperature (for example ambient temperature, e.g. in the range of from 15 to 30° C.). Where X is a leaving group, any suitable leaving group may be used, for example an activated ester. Where X is an —OH group or where X together with the C(O) group to which it is attached forms a carboxylate salt, the group will typically be converted to a suitable leaving group prior to reaction with a dendrimeric intermediate, for example by use of a suitable amide coupling reagent such as PyBOP.

Any suitable isolation and/or purification technique may be utilised, for example the dendrimer may be obtained by dissolution in a suitable solvent (e.g. THF) and precipitation by addition into an antisolvent (e.g. MTBE).

The nucleoside analogue intermediate used in variant a) may itself be obtained, for example, by reaction of nucleoside analogue or protected form thereof (e.g., gemcitabine) with diglycolic anhydride or thiodiglycolic anhydride, for example in the presence of a suitable solvent such as dichloromethane and a suitable base such as triethylamine.

The surface unit intermediate used in variant c) may itself be obtained, for example, by:

i) reacting a PEG intermediate which is:

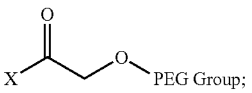

wherein PEG Group is a PEG-containing group, and X is —OH or a leaving group, or wherein X together with the C(O) group to which it is attached forms a carboxylate salt;

with:

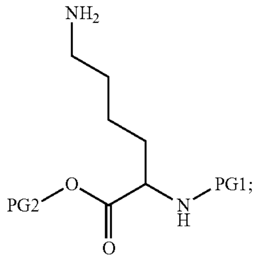

wherein PG1 is an amine protecting group (such as a Boc or Cbz group), and PG2 is either absent, or is an acid protecting group (such as a methyl or benzyl ester);

ii) deprotecting PG1;

iii) reacting the product of step ii) with a nucleoside analogue intermediate which is:

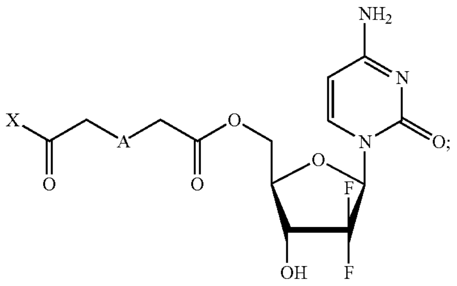

wherein A is O or S, X is —OH or a leaving group (e.g. an active ester), or wherein X together with the C(O) group to which it is attached forms a carboxylate salt; and iv) deprotecting PG2, if present.

The dendrimeric intermediate used in variant a) may itself be obtained by, for example, a sequential process involving:

i) reaction of a core unit (C) containing amino groups, with building units which are protected lysines or analogues thereof, which contain a —C(O)X group, wherein X is —OH or a leaving group (e.g. an active ester) or —CO(X) forms a carboxylate salt, and in which the amino groups present in the lysines or analogues thereof are protected, to form amide linkages between the core unit and building units;

ii) deprotecting protecting groups present on the building units;

iii) reacting free amino groups present on the building units with further building units which are protected lysines or analogues thereof, which contain a —C(O)X group, wherein X is —OH or a leaving group (e.g. an active ester) or —CO(X) forms a carboxylate salt, and in which the amino groups present in the lysines or analogues thereof are protected, to form amide linkages between the different generations of building units;

iv) deprotecting protecting groups present on the building units;

v) repeating steps iii) and iv) until a four generation building unit is produced;

vi) reacting free amino groups present on the building units with:

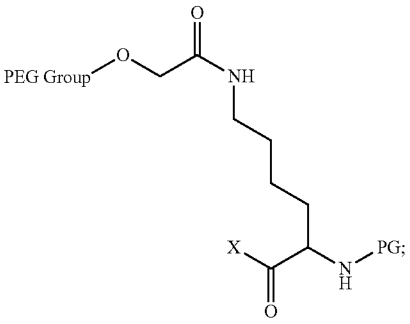

wherein PG is a protecting group, and wherein X is —OH or a leaving group (e.g. an active ester), or wherein X together with the C(O) group to which it is attached forms a carboxylate salt, to form amide linkages therebetween; and vii) deprotecting the protecting groups PG.

Alternatively, the dendrimeric intermediate used in variant a) may be obtained, for example, by carrying out steps i) to v) as described above, and:

vi) reacting free amino groups present on the building units with further building units which are protected lysines or analogues thereof, which contain a —C(O)X group, wherein X is —OH or a leaving group (e.g. an active ester) or —CO(X) forms a carboxylate salt, and in which the amino groups present in the lysines or analogues thereof are orthogonally protected, to form amide linkages between the different generations of building units;

vii) deprotecting a first set of amino protecting groups;

viii) reacting free amino groups present on the building units with:

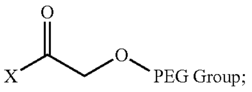

wherein PEG Group is a PEG-containing group, and X is —OH or a leaving group (e.g. an active ester), or wherein X together with the C(O) group to which it is attached forms a carboxylate salt;

ix) deprotecting a second set of amino protecting groups.

The first and second sets of amino protecting groups may, for example, be Fmoc and Boc groups. In some embodiments, step vii) comprises deprotecting a first set of amino protecting groups which are Fmoc groups, e.g. which protect lysine F-amino groups, and step ix) comprises deprotecting a second set of amino protecting groups which are Boc groups, e.g. which protect lysine building unit α-amino groups.

The dendrimeric intermediate used in variant b) may itself be obtained, for example, by carrying out steps i) to v) as described above in relation to variant a), and:

vi) reacting free amino groups present on the building units with:

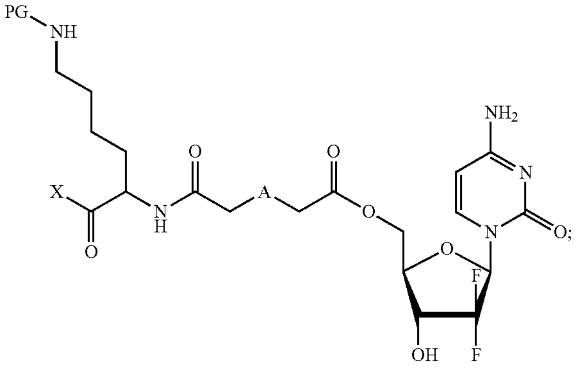

wherein A is O or S, PG is a protecting group, and wherein X is —OH or a leaving group (e.g. an active ester), or wherein X together with the C(O) group to which it is attached forms a carboxylate salt, to form amide linkages therebetween; and vii) deprotecting the protecting groups PG.

Alternatively, the dendrimeric intermediate used in variant b) may be obtained, for example, by carrying out steps i) to v) as described above, and:

vi) reacting free amino groups present on the building units with further building units which are protected lysines or analogues thereof, which contain a —C(O)X group, wherein X is —OH or a leaving group (e.g. an active ester) or —CO(X) forms a carboxylate salt, and in which the amino groups present in the lysines or analogues thereof are orthogonally protected, to form amide linkages between the different generations of building units;

vii) deprotecting a first set of amino protecting groups;

viii) reacting free amino groups present on the building units with:

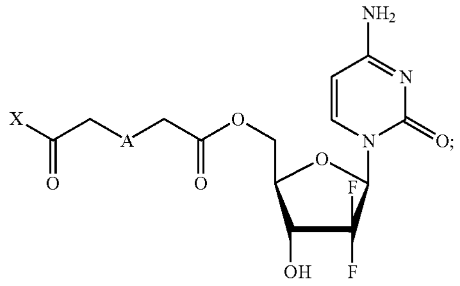

Wherein A is O or S, X is —OH or a leaving group (e.g. an active ester), or wherein X together with the C(O) group to which it is attached forms a carboxylate salt;

vii) deprotecting a second set of amino protecting groups.

The dendrimeric intermediate used in variant c) may itself be obtained, for example, by carrying out steps i) to v) as described above in relation to variant a).

The present disclosure also provides synthetic intermediates useful in producing the dendrimers. Accordingly, there is also provided an intermediate for producing a dendrimer which is:

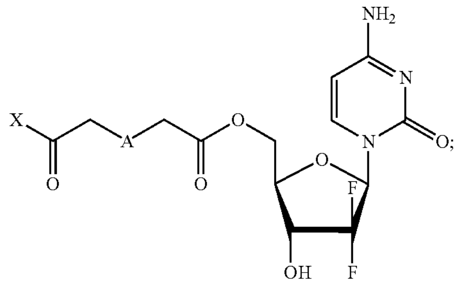

wherein A is O or S, X is —OH or a leaving group (e.g. an active ester), or wherein X together with the C(O) group to which it is attached forms a carboxylate salt. Such an intermediate may be produced, for example, as described above.

There is also provided an intermediate for producing a dendrimer which is:

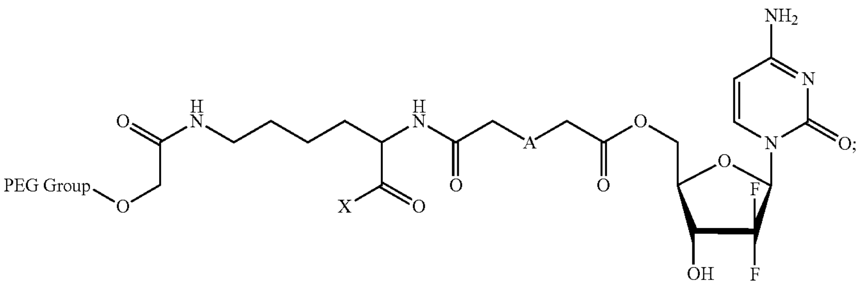

wherein PEG Group is a PEG-containing group, A is O or S, and

X is —OH or a leaving group (e.g. active ester), or wherein X together with the C(O) group to which it is attached forms a carboxylate salt. Such an intermediate may be produced, for example, as described above.

Deprotection of the amino groups (e.g., boc groups) is undertaken utilising suitable reagents and conditions known in the art. In relation to variant d) described above, in some embodiments, deprotection of boc protecting groups is undertaken utilising acidic conditions. In some embodiments, deprotection of boc protecting groups is undertaken utilising trifluoroacetic acid (TFA) conditions. As a consequence of the deprotection conditions, the resulting product of the deprotection reaction may be present in salt form.

For example, the resulting product of the deprotection reaction may be present as the trifluoroacetic acid salt (TFA salt).

In some instances, it is desirable to obtain the dendrimer without the salt (i.e., as the free base), or to exchange salts (e.g., from TFA salt to HCl salt).

Accordingly, in some embodiments, there is provided a process for producing a dendrimer as defined herein, comprising i) obtaining the dendrimer in salt form;

ii) contacting the dendrimer with an ion exchange resin and separating the salt from the conjugate, and iii) separating the dendrimer from the ion exchange resin.

In some embodiments, the product of the deprotection reaction is converted from the salt to the free base. In some embodiments, the product of the deprotection reaction is converted from one particular salt to another particular salt. In some embodiments, the product of the deprotection reaction is converted from the TFA salt to the free base. In some embodiments, the product of the deprotection reaction is converted from the TFA salt to the HCl salt. An ion exchange resin is an insoluble matrix of resin or polymer that acts as a medium for ion exchange. Ion exchange resins may find application in, for example, separation, purification, and decontamination processes. Examples of ion exchange resins include, but are not limited to, AmberLyst® (styrene-divinylbenzene matrix with sulfonic acid functionality), and AmberLite® (styrene-divinylbenzene matrix with sulfonic acid functionality). In some embodiments, the ion exchange resin is AmberLyst®. In some embodiments, the ion exchange resin is AmberLite®. In some embodiments, the ion exchange resin is AmberLyst® A21.

In some embodiments, there is provided a process for converting a dendrimer salt to its free base form, comprising:

i) contacting the dendrimer salt with an ion exchange resin for a period of time; and ii) separating the ion-exchange resin from the dendrimer to obtain the dendrimer in free base form.

In some embodiments, the product of the deprotection reaction is contacted with the ion exchange resin by passing the product through a column comprising the ion exchange resin. In some embodiments, the product of the deprotection reaction is contacted with the ion exchange resin by stirring the product together with the ion exchange resin in solvent for a period of time. The person skilled in the art will appreciate that a variety of suitable solvents may be employed, including, for example, dichloromethane (DCM). The product may be stirred together with the ion exchange resin for an amount of time sufficient so as to form the free base or salt-exchanged product. In some embodiments, the product is stirred together with the ion exchange resin for about 10 minutes, about 30 minutes, about 1 hour, about 12 hours, or about 24 hours. Following stirring, the ion exchange resin may be filtered so as to provide the free base or salt-exchanged product. From here, the dendrimer product may be obtained via any number of methods known in the art.

In some embodiments, the dendrimer is obtained as the salt. In some embodiments, the dendrimer is obtained as the TFA salt. In some embodiments, the dendrimer is obtained as the free base. In some embodiments, the dendrimer is obtained as the hydrochloric acid (HCl) salt.

The present disclosure also relates to the following numbered clauses:

1. A dendrimer comprising:

i) a core unit (C); and ii) building units (BU), each building unit being a lysine residue or an analogue thereof;

wherein the core unit is covalently attached to two building units via amide linkages, each amide linkage being formed between a nitrogen atom present in the core unit and the carbon atom of an acyl group present in a building unit;

the dendrimer being a five generation building unit dendrimer;

wherein building units of different generations are covalently attached to one another via amide linkages formed between a nitrogen atom present in one building unit and the carbon atom of an acyl group present in another building unit;

the dendrimer further comprising:

iii) a plurality of first terminal groups (T1) each comprising a residue of a nucleoside analogue, which nucleoside analogue has a hydroxyl group, covalently attached to a diacyl linker group of formula:

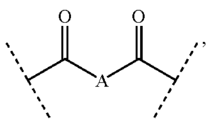

wherein A is a $C_2$-$C_{10}$ alkylene group which is interrupted by at least one O, S, NH, or N(Me), or in which A is a heterocycle selected from the group consisting of tetrahydrofuran, tetrahydrothiophene, pyrrolidine, and N-methylpyrrolidine; and iv) a plurality of second terminal groups (T2) each comprising a PEG or PEOX group;

or a pharmaceutically acceptable salt thereof.

2. A dendrimer according to clause 1, wherein the nucleoside analogue is selected from the group consisting of gemcitabine and cytarabine.

3. A dendrimer according to clause 2, wherein the nucleoside analogue is gemcitabine.

4. A dendrimer according to any one of clauses 1 to 3, wherein the core unit is formed from a core unit precursor comprising two amino groups.

5. A dendrimer according to any one of clauses 1 to 4, wherein the core unit is:

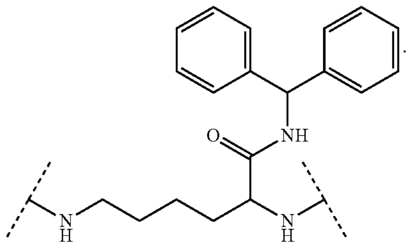

6. A dendrimer according to any one of clauses 1 to 5, wherein the building units are each:

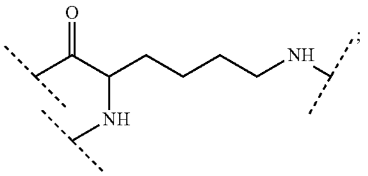

wherein the acyl group of each building unit provides a covalent attachment point for attachment to the core or to a previous generation building unit; and wherein each nitrogen atom provides a covalent attachment point for covalent attachment to a subsequent generation building unit, a first terminal group or a second terminal group.

7. A dendrimer according to clause 6, wherein the building units are each:

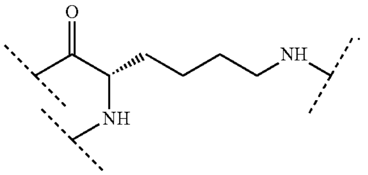

8. A dendrimer according to any one of clauses 1 to 7, wherein the dendrimer has five complete generations of building units.

9. A dendrimer according to any one of clauses 1 to 8, wherein the diacyl linker is selected from the group consisting of:

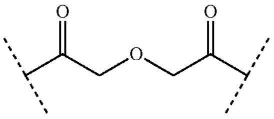

and

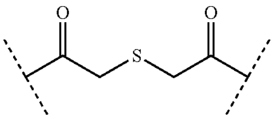

.

10. A dendrimer according to any one of clauses 1 to 9, wherein the diacyl linker is:

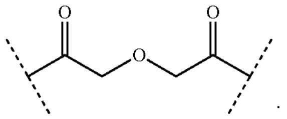

11. A dendrimer according to any one of clauses 1 to 9, wherein the diacyl linker is:

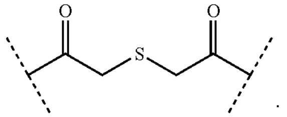

12. A dendrimer according to any one of clause 1 to 10, wherein the nucleoside analogue is gemcitabine and is covalently attached to the diacyl linker group as shown below:

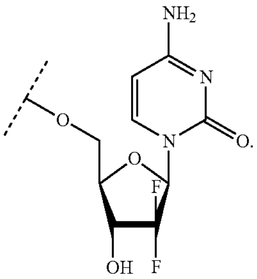

13. A dendrimer according to clause 12, wherein the first terminal group is:

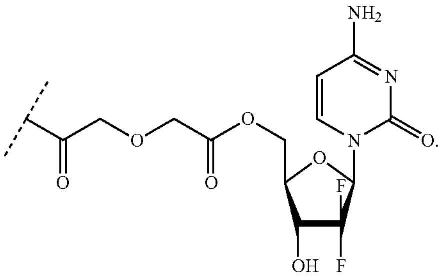

14. A dendrimer according to clause 12, wherein the first terminal group is:

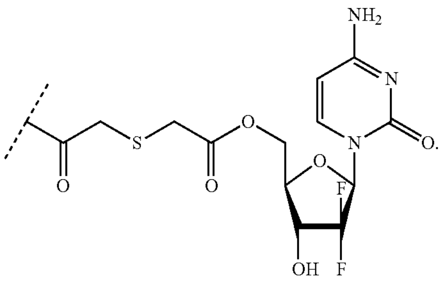

15. A dendrimer according to any one of clauses 1 to 14, wherein the second terminal groups comprise PEG groups having a mean molecular weight of at least 500 Daltons.

16. A dendrimer according to clause 15, wherein the second terminal groups comprise PEG groups having an average molecular weight in the range of from 500 to 2500 Daltons.

17. A dendrimer according to clause 16, wherein the second terminal groups comprise PEG groups having an average molecular weight in the range of from 1900 to 2300 Daltons.

18. A dendrimer according to clause 16, wherein the second terminal groups comprise PEG groups having an average molecular weight in the range of from 1000 to 1200 Daltons.

19. A dendrimer according to clause 16, wherein the second terminal groups comprise PEG groups having an average molecular weight in the range of from 500 to 650 Daltons.

20. A dendrimer according to any one of clauses 1 to 19, wherein the PEG group is a methoxy-terminated PEG.

21. A dendrimer according to any one of clauses 1 to 20, wherein the second terminal groups each comprise a PEG group covalently attached to a PEG linking group (L1) via an ether linkage formed between a carbon atom present in the PEG group and an oxygen atom present in the PEG linking group, and each second terminal group is covalently attached to a building unit via an amide linkage formed between a nitrogen atom present in a building unit and the carbon atom of an acyl group present in the PEG linking group.

22. A dendrimer according to clause 21, wherein the second terminal groups are each:

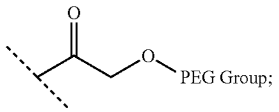

and wherein the PEG group is a methoxy-terminated PEG having an average molecular weight in the range of from 500 to 2500 Daltons.

23. A dendrimer according to clause 22, wherein the dendrimer comprises surface units comprising an outer building unit attached to a first terminal group and a second terminal group, the surface units having the structure:

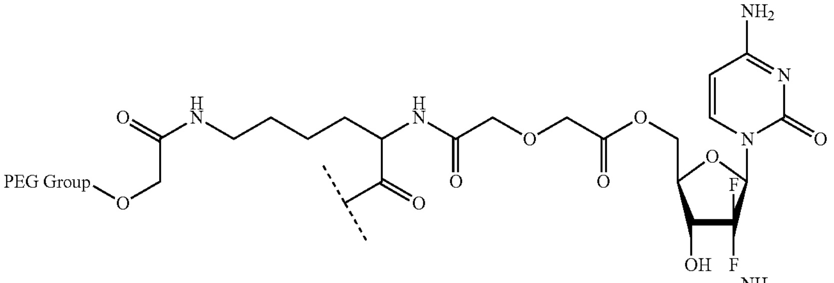

or

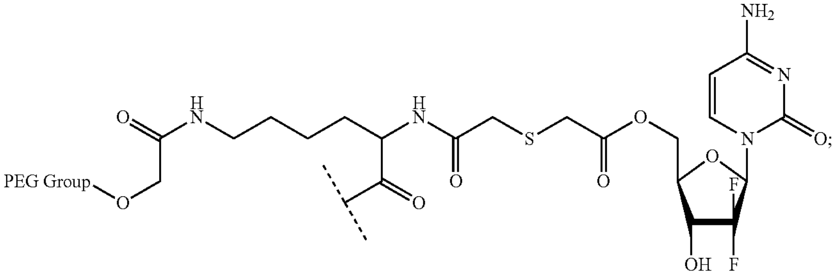

;

and wherein the PEG group is a methoxy-terminated PEG having an average molecular weight in the range of from 500 to 2500 Daltons.

24. A dendrimer according to clause 23, wherein the PEG has an average molecular weight in the range of from 2000 to 2400 Daltons.

25. A dendrimer according to clause 24, wherein the dendrimer has from 28 to 32 surface units.

26. A dendrimer according to any one of clauses 1 to 25, wherein at least 40% of the nitrogen atoms present in the outer building units are each covalently attached to a first terminal group; and at least 40% of the nitrogen atoms present in the outer building units are each covalently attached to a second terminal group.

27. A dendrimer according to any one of clauses 1 to 26, wherein the five generations of building units are complete generations, and wherein the outer generation of building units provides 64 nitrogen atoms for covalent attachment to a first terminal group or a second terminal group, wherein from 24 to 32 first terminal groups are covalently attached to one of said nitrogen atoms, and wherein from 24 to 32 second terminal groups are each covalently attached to one of said nitrogen atoms.

28. A dendrimer according to any one of clauses 1 to 27, wherein no more than one fifth of the nitrogen atoms present in said outer generation of building units are unsubstituted.

29. A dendrimer according to any one of clauses 1 to 28, wherein the dendrimer is a compound having a structure as shown in FIG. 10, in which T1' represents a first terminal group which is:

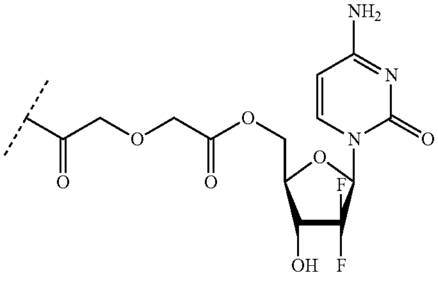

or

-continued

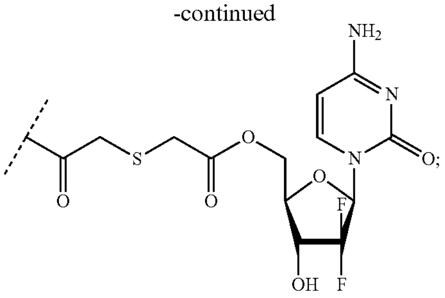

;

T2' represents a second terminal group which is:

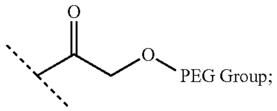

;

wherein the PEG group is a methoxy-terminated PEG having an average molecular weight in the range of from 500 to 2500 Daltons, or T2' represents H, and wherein less than 5 of T2' are H.

30. A composition comprising a plurality of dendrimers or pharmaceutically acceptable salts thereof,

- wherein the dendrimers are as defined according to any one of clauses 1 to 29,
- the mean number of first terminal groups per dendrimer in the composition is in the range of from 24 to 32, and
- the mean number of second terminal groups per dendrimer in the composition is in the range of from 24 to 32.

31. A pharmaceutical composition comprising:

i) a dendrimer are as defined according to any one of clauses 1 to 29, or a pharmaceutically acceptable salt thereof; and ii) a pharmaceutically acceptable excipient.

32. A pharmaceutical composition according to clause 31, wherein the composition is formulated for parenteral delivery.

33. A pharmaceutical composition according to clauses 31 or 32, wherein the composition is formulated for intravenous delivery.

34. A dendrimer according to any one of clauses 1 to 29, or a pharmaceutical composition according to any one of clauses 31 to 33, for use in therapy.

35. A dendrimer according to any one of clauses 1 to 29, or a pharmaceutical according to any one of clauses 31 to 33, for use in the treatment of cancer.

36. A method of treating cancer comprising administering to a subject in need thereof a therapeutically effective amount of a dendrimer according to any one of clauses 1 to 29 or a pharmaceutical composition according to any one of clauses 31 to 33.

37. Use of a dendrimer according to any one of clauses 1 to 29, or of a composition according to any one of clauses 31 to 33, in the manufacture of a medicament for the treatment of cancer.

38. A method, use, or dendrimer or composition for use, according to any one of clauses 35 to 37, wherein the cancer is selected from the group consisting of breast cancer, ovarian cancer, non-small cell lung cancer, an upper gastro-intestinal cancer (e.g. pancreatic cancer) and bladder cancer.

39. A method, use, or dendrimer or composition for use according to any one of clauses 35 to 38, wherein the amount of dendrimer administered is sufficient to deliver an amount of active agent in the range of from 1 to 1250 mg of nucleoside analogue/$m^2$.

40. A method, use, or dendrimer or composition for use according to any one of clauses 35 to 39, wherein the dendrimer is administered in combination with a further anti-cancer drug.

41. A method, use, or dendrimer or composition for use according to clause 40, wherein the dendrimer is administered in combination with a second dendrimer, and wherein the second dendrimer comprises:

i) a core unit (C); and ii) building units (BU), each building unit being a lysine residue or an analogue thereof;

wherein the core unit is covalently attached to two building units via amide linkages, each amide linkage being formed between a nitrogen atom present in the core unit and the carbon atom of an acyl group present in a building unit;

the dendrimer being a five generation building unit dendrimer;

wherein building units of different generations are covalently attached to one another via amide linkages formed between a nitrogen atom present in one building unit and the carbon atom of an acyl group present in another building unit;

the dendrimer further comprising:

iii) a plurality of first terminal groups (T1) each comprising a residue of a taxane, which taxane has a hydroxyl group, covalently attached to a diacyl linker group of formula:

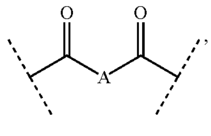

wherein A is a $C_2$-$C_{10}$ alkylene group which is interrupted by at least one O, S, NH, or N(Me), or in which A is a heterocycle selected from the group consisting of tetrahydrofuran, tetrahydrothiophene, pyrrolidine, and N-methylpyrrolidine; and iv) a plurality of second terminal groups (T2) each comprising a PEG or PEOX group;

or a pharmaceutically acceptable salt thereof.

42. A method, use, or dendrimer or composition for use as claimed in clause 41, wherein the taxane is selected from the group consisting of docetaxel, paclitaxel and cabazitaxel.

43. A method, use, or dendrimer or composition for use according to clause 42, wherein the taxane is docetaxel.

44. A method, use, or dendrimer or composition for use according to clause 40, wherein the dendrimer is administered in combination with a further anticancer drug selected from the group consisting of a platinum-containing pharmaceutical agent, a taxane, a PARP inhibitor, a vinca alkaloid, a topoisomerase I inhibitor, and an anthracycline.

45. A method, use, or dendrimer or composition for use according to clause 44, wherein the dendrimer is administered in combination with a further anticancer drug selected from the group consisting of carboplatin, cisplatin, oxaliplatin, paclitaxel, Nab-paclitaxel, vindesine, doxorubicin, irinotecan, SN38 and erlotinib.

46. A method, use, or dendrimer or composition for use according to any one of clauses 35 to 45, wherein administration of the dendrimer provides enhanced clinical efficacy in comparison to administration of an equivalent dose of free nucleoside analogue.

47. A method, use, or dendrimer or composition for use according to any one of clauses 35 to 46, wherein administration of the dendrimer provides reduced side effects and/or toxicity in comparison to administration of an equivalent dose of free nucleoside analogue.

48. A method, use, or dendrimer or composition for use according to any one of clauses 35 to 47, wherein administration of the dendrimer provides therapeutically effective plasma concentration levels of gemcitabine for an extended period of time following administration, in comparison to administration of an equivalent dose of free nucleoside analogue.

The present disclosure will now be described with reference to the following examples which illustrate some particular aspects of the present disclosure. However, it is to be understood that the particularity of the following description of the present disclosure is not to supersede the generality of the preceding description of the present disclosure.

EXAMPLES

The dendrimers represented in the examples below include reference to the core and the building units in the outermost generation of the dendrimer. The subsurface generations are not depicted. For example, the dendrimer BHALys$[Lys]_{32}$ is representative of a 5 generation dendrimer having the formula BHALys$[Lys]_2[Lys]_4[Lys]_8[Lys]_{16}[Lys]_{32}$.

32‡ relates to the number of E surface amino groups on the dendrimer available for substitution, e.g. with $PEG_{\sim2100}$. The actual mean number of $PEG_{\sim2100}$ groups attached to the BHALys$[Lys]_{32}$ was determined experimentally by $^1$H NMR.

Synthesis of BHALys$[Lys]_{32}[\alpha\text{-}NH_2TFA]_{32}[\varepsilon\text{-}PEG_{\sim2100}]_{32‡}$ BHALys$[Lys]_{32}[\alpha\text{-}NH_2TFA]_{32}[\varepsilon\text{-}PEG_{\sim2100}]_{32‡}$ was prepared by analogous methods to those described in, for example, WO2020/014750A1 and WO2020/102852A1, the entire contents of which are incorporated herein by reference.

Synthesis of BHALys[Lys]$_{32}$[α-$NH_2$TFA]$_{32}$[ε-PEG$_{\sim570}$]$_{32}$‡

The title compound was prepared in an analogous fashion to BHALys[Lys]$_{32}$[α-$NH_2$TFA]$_{32}$[ε-PEG$_{\sim2100}$]$_{32}$: as described above, but using NHS-PEG$_{\sim570}$ in place of NHS-PEG$_{\sim2100}$. $^1$H NMR (300 MHz, MeOD) δ 7.35-7.31 (m, 10H), 6.19 (s, 1H), 4.41-4.04 (m, 53H), 3.91-3.55 (m, 1431H), 3.43-3.37 (m, 103H), 3.25-3.14 (m, 117H), 2.50-3.47 (m, 61H), 1.88-1.46 (m, 378H). 30 PEG$_{570}$ per dendrimer. Quantification of the amount of PEG$_{570}$ molecules per dendrimer by $^1$H NMR spectroscopy showed an average of 30 PEG$_{570}$ molecules per dendrimer.

Synthesis of BHALys[Lys]$_{32}$[α-$NH_2$TFA]$_{32}$[ε-PEG$_{\sim100}$]$_{32}$‡

The title compound was prepared in an analogous fashion to BHALys[Lys]$_{32}$[α-$NH_2$TFA]$_{32}$[ε-PEG$_{\sim2100}$]$_{32}$‡ as described above, but using NHS-PEG$_{\sim1100}$ in place of NHS-PEG$_{\sim2100}$. $^1$H NMR (300 MHz, MeOD)™ 8.12-8.01 (m, 21H), 7.38-7.30 (m, 13H), 6.09 (s, 3H), 4.35 (s, 39H), 4.04-3.54 (m, 2858H), 3.38 (s, 93H), 3.23-3.09 (m, 104H), 2.50-2.48 (m, 64H), 1.90-1.32 (m, 378H).

Synthesis of Linker-Gemcitabine

General Synthesis of Drug Linker Intermediates (O-Linked)

Scheme

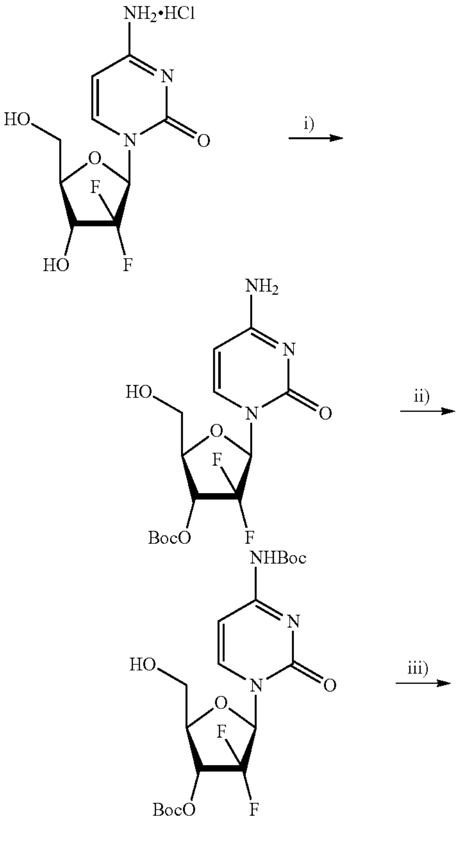

-continued

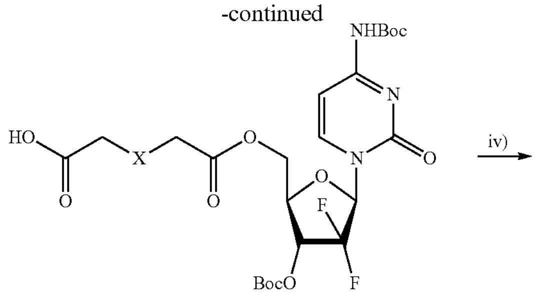

X = S
X = O
X = $CH_2$

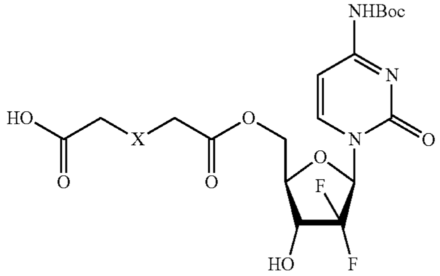

X = S
X = O
X = $CH_2$ i) $Boc_2O$, dioxane, $Na_2CO_3$, RT; ii) $Boc_2O$, dioxane, 37° C., 3d; iii) Anhydride, DIPEA, DCM, RT; iv) TFA, DCM.

Synthesis of (2R,3R,5R)-5-(4-amino-2-oxopyrimidin-1 (2H)-yl)-4,4-difluoro-2-(hydroxymethyl) tetrahydrofuran-3-yl tert-butyl carbonate

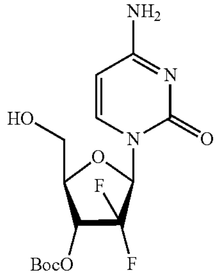

To a vigorously stirred suspension of gemcitabine·HCl (5.0 g, 0.017 mol, 1.0 equiv.) in dioxane (240 mL) and water (60 mL) at RT was added sodium carbonate (8.83 g, 0.083 mol, 5.0 equiv.) followed by dropwise addition of di-tert-butyl dicarbonate (3.99 g, 0.018 mol, 1.1 equiv.) over 1 min. The reaction mixture was left to stir at RT. Analysis of the reaction mixture by TLC (4:4:1 DCM:Acetone:EtOH v/v, UV vis) after stirring for 18 h showed starting material present and so a further portion of di-tert-butyl dicarbonate was added in a single portion (2.00 g, 9.2 mmol) and stirring continued. After stirring for 3 days, the reaction mixture was diluted with water (150 mL) and then filtered. The solids were washed with EtOAc (200 mL) and the combined filtrates were extracted with EtOAc (2×200 mL). The combined organics were then washed with brine (300 mL), dried ($MgSO_4$) and the volatiles concentrated in vacuo to give a white foam. The foam was redissolved in minimum amount of DCM:Acetone (1:1 v/v, ~10 mL). A solid began to crystallize from solution at RT. The resultant suspension was then kept in the cold room (4° C.) overnight, and the filtered to obtain the product as a white solid (3.89 g, 58%). LCMS (Philic Formic): $t_R$ (min)=7.85 ESI (+ve) m/z=364 (M+H$^+$). $^1$H NMR (300 MHz, $(CD_3)_2S{=}O$) δ 7.66 (d, J=7.56 Hz, 1H), 7.54 (s, 1H), 7.43 (s, 1H), 6.22 (t, J=9.16 Hz, 1H), 5.85 (d, J=7.14 Hz, 1H), 5.76 (s, 1H), 5.34 (t, J=5.88 Hz, 1H), 5.22-5.13 (m, 1H), 4.17-4.12 (m, 1H), 3.78-3.61 (m, 2H), 2.52-2.50 (m, 1H), 1.46 (s, 9H).

Synthesis of tert-butyl (1-((2R,4R,5R)-4-((tert-butoxycarbonyl)oxy)-3,3-difluoro-5-(hydroxymethyl)tetrahydrofuran-2-yl)-2-oxo-1,2-dihydropyrimidin-4-yl)carbamate

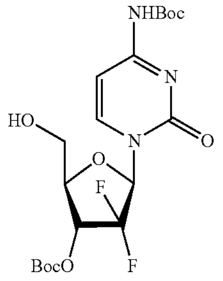

Di-tert-butyl dicarbonate (7.2 g, 33.1 mmol, 10.0 equiv.) was added to a solution of (2R,3R,5R)-5-(4-amino-2-oxopyrimidin-1 (2H)-yl)-4,4-difluoro-2-(hydroxymethyl)tetrahydrofuran-3-yl tert-butyl carbonate (1.2 g, 3.3 mmol, 1.0 equiv.) in 130 mL dioxane and the reaction mixture heated at 37° C. for 3 days. TLC analysis (DCM:Acetone:EtOH=10:10:1 v/v) of the reaction mixture showed formation of a new non-polar spot with no starting material remaining. The crude reaction mixture was concentrated under reduced pressure and purified by column chromatography DCM: Acetone (gradient elution from 1:3 to 1:1 v/v) to give the desired product as a white solid (1.4 g, 92%). $^1$H NMR (300 MHz, $(CD_3)_2CO$) δ 8.22 (d, 1H, J=6.00 Hz), 7.28 (d, 1H, J=6.20 Hz), 6.37 (t, 1H, J=9.00 Hz), 5.40-5.31 (m, 1H), 4.33-4.28 (m, 1H), 4.02 (dd, 1H, J=3.00, 15.0 Hz), 3.85 (dd, 1H, J=3.00, 12.0 Hz), 1.53 (s, 9H), 1.51 (s, 9H).

Synthesis of 5-(((2R,3R,5R)-5-(4-((tert-butoxycarbonyl)amino)-2-oxopyrimidin-1(2H)-yl)-3-((tert-butoxycarbonyl)oxy)-4,4-difluorotetrahydrofuran-2-yl)methoxy)-5-oxopentanoic acid

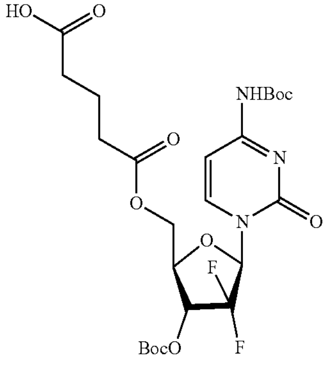

To a stirred solution of tert-butyl (1-((2R,4R,5R)-4-((tert-butoxycarbonyl)oxy)-3,3-difluoro-5-(hydroxymethyl)tetrahydrofuran-2-yl)-2-oxo-1,2-dihydropyrimidin-4-yl)carbamate (200 mg, 0.43 mmol) in anhydrous DMF (2 mL) under an atmosphere of nitrogen at 0° C. was added DIPEA (0.4 mL, 2.15 mmol) followed by glutaric anhydride (100 mg, 0.86 mmol). The reaction mixture was slowly warmed to RT. After stirring for 4 h at RT, the volatiles were removed in vacuo and residue was dissolved in ethyl acetate (20 mL) and the organics then washed with aq. 10% $NaHCO_3$ (2×10 mL), water (2×20 mL), brine (20 mL) and dried ($Na_2SO_4$). The volatiles were removed in vacuo and the residue was purified by column chromatography on silica gel eluting with DCM:MeOH to give 5-(((2R,3R,5R)-5-(4-((tert-butoxycarbonyl)amino)-2-oxopyrimidin-1(2H)-yl)-3-((tert-butoxycarbonyl) oxy)-4,4-difluorotetrahydrofuran-2-yl) methoxy)-5-oxopentanoic acid as a white solid (130 mg, 54%). LCMS (philic TFA) $t_R$=10.8 min, m/z (578). $^1$H NMR (300 MHz, $(CD_3)_2S{=}O$) δ 12.00 (bs, 1H), 10.59 (bs, 1H), 7.98 (d, J=9 Hz, 1H), 7.12 (d, J=9 Hz, 1H), 6.30 (t, J=9 Hz, 1H), 5.38-5.18 (m, 1H), 4.51-4.32 (m, 3H), 2.41 (t, J=6 Hz, 2H), 2.27 (t, J=6 Hz, 2H), 1.83-1.66 (m, 2H), 1.47 (s, 18H).

Synthesis of 5-(((2R,3R,5R)-5-(4-amino-2-oxopyrimidin-1(2H)-yl)-4,4-difluoro-3-hydroxy tetrahydrofuran-2-yl)methoxy)-5-oxopentanoic acid

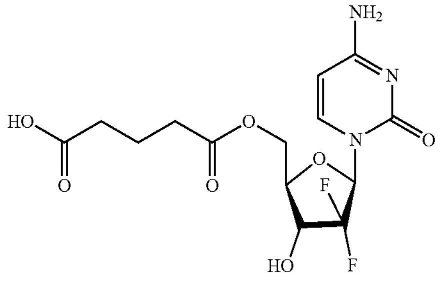

To a stirred solution of 5-(((2R,3R,5R)-5-(4-((tert-butoxycarbonyl)amino)-2-oxopyrimidin-1(2H)-yl)-3-((tert-butoxycarbonyl)oxy)-4,4-difluorotetrahydrofuran-2-yl) methoxy)-5-oxopentanoic acid (30 mg, 0.055 mmol) in anhydrous DCM (2 mL) at 0° C. under nitrogen was added TFA (2 mL) (dropwise). Once addition was complete, the reaction mixture was allowed to warm to RT. After 4 h, the volatiles were removed in vacuo, the residue triturated with diethyl ether/petroleum ether (~20 mL, 1:1 v/v), then dissolved in water and freeze-dried to give the product as a white solid (15 mg, 75%). LCMS (philic TFA) $t_R$=5.43 min; m/z=380. $^1$H NMR (300 MHz, $CD_3OD$) δ 7.90 (d, J=9 Hz, 1H), 6.23-6.17 (m, 1H), 4.45 (bd, J=6 Hz, 1H), 4.30-4.16 (m, 1H), 3.49 (dd, J=6, 9 Hz, 2H), 2.48 (t, J=6 Hz, 1H), 2.40-2.33 (m, 2H), 1.96-1.83 (m, 1H), 1.18 (t, J=6 Hz, 2H).

2-((2-(((2R,3R,5R)-5-(4-((tert-butoxycarbonyl)amino)-2-oxopyrimidin-1(2H)-yl)-3-((tert-butoxycarbonyl)oxy)-4,4-difluorotetrahydrofuran-2-yl)methoxy)-2-oxoethyl)thio)acetic acid

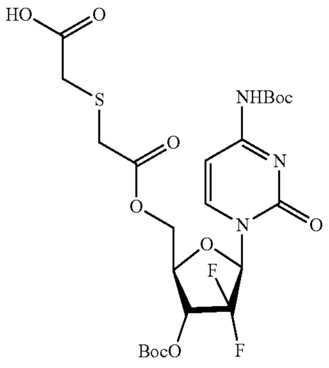

To a stirred solution of tert-butyl (1-((2R,4R,5R)-4-((tert-butoxycarbonyl)oxy)-3,3-difluoro-5-(hydroxymethyl)tetrahydrofuran-2-yl)-2-oxo-1,2-dihydropyrimidin-4-yl)carbamate (0.4 g, 0.86 mmol, 1.0 equiv.) in DCM (15 mL) at 0° C. was added DIPEA (0.19 mL, 1.04 mmol, 1.2 equiv.) followed by thiodiglycolic anhydride (0.11 g, 0.86 mmol, 1.0 equiv.). The reaction mixture was stirred for 10 min, then warmed to RT and stirred for 2 h. DCM was added (100 mL) and the organics washed with pH 3 buffer solution (3×100 mL) or until the aqueous phase remained at pH 3. The organics were washed with brine (100 mL), dried ($MgSO_4$) and concentrated in vacuo. The residue was purified by column chromatography on silica gel eluting with MeOH:DCM (gradient elution from 0:100 to 1:19 v/v) to afford the product as a white solid (0.34 g, 66%). $^1$H NMR (300 MHz, $CD_3OD$) δ 8.04 (d, J=4.0 Hz, 1H), 7.38 (d, J=3.5 Hz, 1H), 6.35 (t, J=9.0 Hz, 1H), 5.33-5.25 (m, 1H), 4.55-4.45 (m, 3H), 3.54 (s, 2H), 3.43 (s, 2H), 1.55, 1.52 (s, 18H). $^1$H NMR (300 MHz, $(CD_3)_2S{=}O$) δ 12.67 (bs, 1H), 10.57 (bs, 1H), 8.00 (d, J=6.0 Hz, 1H), 7.12 (d, J=6.0 Hz, 1H), 6.32 (t, J=9.0 Hz, 1H), 5.30 (bs, 1H), 4.54-4.35 (m, 3H), 3.5 (s, 2H), 3.39 (s, 2H), 1.47 (s, 18H).

Alternate synthesis of 2-((2-(((2R,3R,5R)-5-(4-((tert-butoxycarbonyl)amino)-2-oxopyrimidin-1(2H)-yl)-3-((tert-butoxycarbonyl)oxy)-4,4-difluorotetrahydrofuran-2-yl)methoxy)-2-oxoethyl)thio)acetic acid

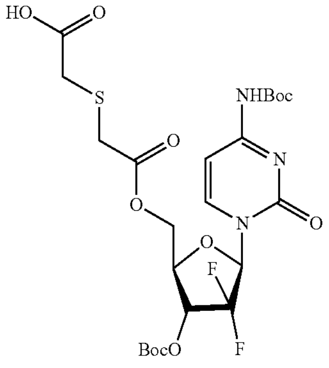

To a stirred solution of tert-butyl (1-((2R,4R,5R)-4-((tert-butoxycarbonyl)oxy)-3,3-difluoro-5-(hydroxymethyl)tetrahydrofuran-2-yl)-2-oxo-1,2-dihydropyrimidin-4-yl)carbamate (4.01 g, 8.65 mmol) in DCM (40 mL) at RT was added NMM (1.40 mL, 1.27 mmol) followed by thiodiglycolic anhydride (1.59 g, 1.20 mmol). The reaction mixture was stirred at RT overnight then diluted with DCM (20 mL). The organic layer was washed with pH 3 buffer solution (2×60 mL, adjusted to pH 3 with 1M HCl) or until the aqueous phase remained at pH 3, then with brine (60 mL), dried over $Na_2SO_4$ and concentrated in vacuo to give the product as white flaky solid (4.85 g, 94%). $^1$H NMR (300 MHz, $(CD_3)_2S{=}O$) δ 12.62 (bs, 1H), 10.59 (bs, 1H), 8.00 (d, J=9.0 Hz, 1H), 7.12 (d, J=6.0 Hz, 1H), 6.31 (t, J=9.0 Hz, 1H), 5.34-5.25 (m, 1H), 4.51-4.38 (m, 3H), 3.52 (s, 2H), 3.39 (s, 2H), 1.46 (s, 18H). HPLC (C8 Xbridge, 3×100 mm) gradient: 5% ACN/H2O (0-1 min), 5-80% ACN (1-7 min), 80% ACN (7-12 min), 80-5% ACN (12-13 min), 5% ACN (13-15 min), 243 nm, 10 mM ammonium formate buffer, 0.4 mL/min, Rt (min)=7.69 min (broad peak), Purity 96.4%.

Synthesis of 2-((2-(((2R,3R,5R)-5-(4-((tert-butoxycarbonyl)amino)-2-oxopyrimidin-1(2H)-yl)-3-((tert-butoxycarbonyl)oxy)-4,4-fluorotetrahydrofuran-2-yl)methoxy)-2-oxoethoxy)acetic acid

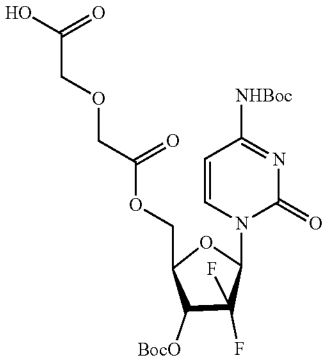

To a stirred solution of tert-butyl (1-((2R,4R,5R)-4-((tert-butoxycarbonyl)oxy)-3,3-difluoro-5-(hydroxymethyl)tetrahydrofuran-2-yl)-2-oxo-1,2-dihydropyrimidin-4-yl)carbamate (0.43 g, 0.93 mmol, 1.0 equiv.) in DCM (15 mL) at 0° C. was added DIPEA (0.25 mL, 1.39 mmol, 1.5 equiv.) followed by diglycolic anhydride (0.13 g, 1.11 mmol, 1.0 equiv.). The reaction mixture was stirred for 10 min then warmed to RT and stirred for 2 h. DCM was added (100 mL) and the organics washed with pH 3 buffer solution (3×100 mL) or until the aqueous phase remained at pH 3. The organics were washed with brine (100 mL), dried ($MgSO_4$) and concentrated in vacuo. to afford the product as a pale yellow solid (0.53 g, 98%). $^1$H NMR (300 MHz, $(CD_3)_2S{=}O$) δ 12.72 (bs, 1H), 10.59 (bs, 1H), 8.00 (d, J=9.0 Hz, 1H), 7.10 (d, J=6.0 Hz, 1H), 6.31 (t, J=9.0 Hz, 1H), 5.31 (bs, 1H), 4.54-4.39 (m, 3H), 4.28 (s, 2H), 4.13 (s, 2H), 1.47 (s, 18H).

Alternate synthesis of 2-((2-(((2R,3R,5R)-5-(4-((tert-butoxycarbonyl)amino)-2-oxopyrimidin-1(2H)-yl)-3-((tert-butoxycarbonyl)oxy)-4,4-difluoro-tetrahydrofuran-2-yl)methoxy)-2-oxoethoxy)acetic acid

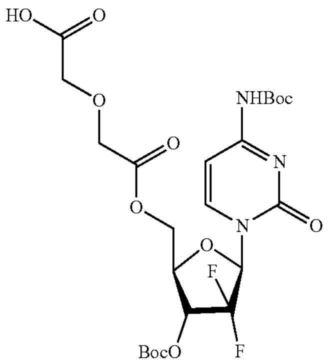

To a stirred solution of tert-butyl (1-((2R,4R,5R)-4-((tert-butoxycarbonyl)oxy)-3,3-difluoro-5-(hydroxymethyl)tetrahydrofuran-2-yl)-2-oxo-1,2-dihydropyrimidin-4-yl)carbamate (4.12 g, 8.89 mmol, 1.0 equiv.) in DCM (40 mL) at RT was added TEA (1.90 mL, 1.36 mmol) followed by diglycolic anhydride (1.35 g, 1.17 mmol). The reaction was stirred overnight at RT then diluted with DCM (40 mL). The organic layer was washed with pH 3 buffer solution (3×80 mL, adjusted to pH 3 with 1M HCl) or until the aqueous phase remained at pH 3, washed with brine (80 mL), dried over $Na_2SO_4$ and concentrated in vacuo to give the product as white flaky solid (5.22 g, 101%). $^1H$ NMR (300 MHz, $(CD_3)_2S{=}O$) δ 12.70 (bs, 1H), 10.58 (bs, 1H), 8.00 (d, J=9.0 Hz, 1H), 7.11 (d, J=6.0 Hz, 1H), 6.30 (t, J=9.0 Hz, 1H), 5.36-5.26 (m, 1H), 4.54-4.41 (m, 3H), 4.27 (s, 2H), 4.12 (s, 2H), 1.46 (s, 18H). HPLC (C8 Xbridge, 3×100 mm) gradient: 5% ACN/H2O (0-1 min), 5-80% ACN (1-7 min), 80% ACN (7-12 min), 80-5% ACN (12-13 min), 5% ACN (13-15 min), 243 nm, 10 mM ammonium formate buffer, 0.4 mL/min, Rt (min)=7.31 min (broad peak), Purity 100%.

Synthesis of Gemcitabine-Dendrimer Conjugates

Example dendrimers of the present disclosure are summarised in the table below:

| Examples | Dendrimer | wt % Gemcitabine Loading | Linker | PEG MW |
|---|---|---|---|---|
| 1 | 1 | 15 | TDA | ~1100 |
| 2 | 2 | 17 | TDA | ~570 |
| 3, 3A, 5B | 3 | 7.8 | TDA | ~2100 |
| 4 | 4 | 17 | DGA | ~570 |
| 5 | 5 | 14 | DGA | ~1100 |
| 4A, 5C, 6 | 6 | 9.9 | DGA | ~2100 |
| Comparative Examples | | | | |
| 7 | 7 | — | Glutaric | ~1100 |
| 8 | 8 | 8.8 | Glutaric | ~2100 |

Example 1: [BHA Lys][Lys]$_{30}$[Lys]$_{32}$ [(α-NH-TDA-Gemcitabine)$_{32}$ (ε-NHPEG$_{\sim1100}$)$_{32}$] (Compound 1)

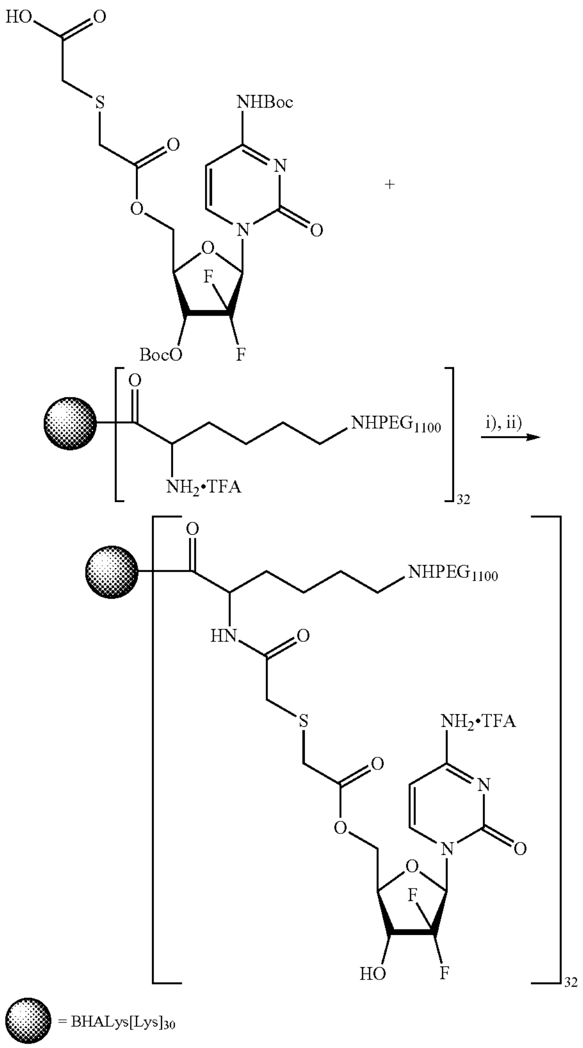

i) PyBOP, NMM, DMF, RT; ii) TFA:DCM (1:1 v/v), RT.

To a solution of 2-((2-(((2R,3R,5R)-5-(4-((tert-butoxycarbonyl)amino)-2-oxopyrimidin-1(2H)-yl)-3-((tert-butoxycarbonyl)oxy)-4,4-difluorotetrahydrofuran-2-yl)methoxy)-2-oxoethyl)thio)acetic acid (0.11 g, 0.18 mmol) in DMF (10 mL) was added PyBOP (0.10 g, 0.18 mmol) followed by a solution of the dendrimer (0.2 g, 0.004 mmol) in DMF (20 mL) and DIPEA (0.06 mL, 0.34 mmol). The reaction mixture was monitored by HPLC analysis and left to stir overnight at RT. The reaction mixture was then concentrated in vacuo and the residue dissolved in TFA:DCM (10 mL, 1:1 v/v) and stirred overnight at RT. The volatiles were removed in vacuo and the residue purified by size exclusion chromatography on Sephadex® LH-20 (height ~35 cm, dia. ~2.5 cm) eluting with acetonitrile (rate ~1 drop per second, fraction size=400 drops). All fractions were analysed by HPLC and those containing the desired product were combined and concentrated in vacuo to afford the product as a pale-yellow waxy solid (216 mg, 86%). $^1H$ NMR (300 MHz, $CD_3OD$) δ 7.92 (s, 33H), 7.29 (s, 12H), 6.28-6.26 (m, 60H), 4.59-4.22 (m, 210H), 3.90-3.54 (m, 2964H), 3.43-3.38 (m, 150H), 3.20 (s, 111H), 2.47-2.45 (m, 64H), 1.83-1.31 (m, 379H). Quantification of the amount of gemcitabine molecules per dendrimer by $^{1}H$ NMR spectroscopy showed an average of 30 gemcitabine molecules per dendrimer or 15% wt. gemcitabine.

Example 2: [BHA Lys][Lys]$_{30}$[Lys]$_{32}$ [(α-NH-TDA-Gemcitabine)$_{32}$ (ε-NHPEG$_{570}$)$_{32}$] (Compound 2)

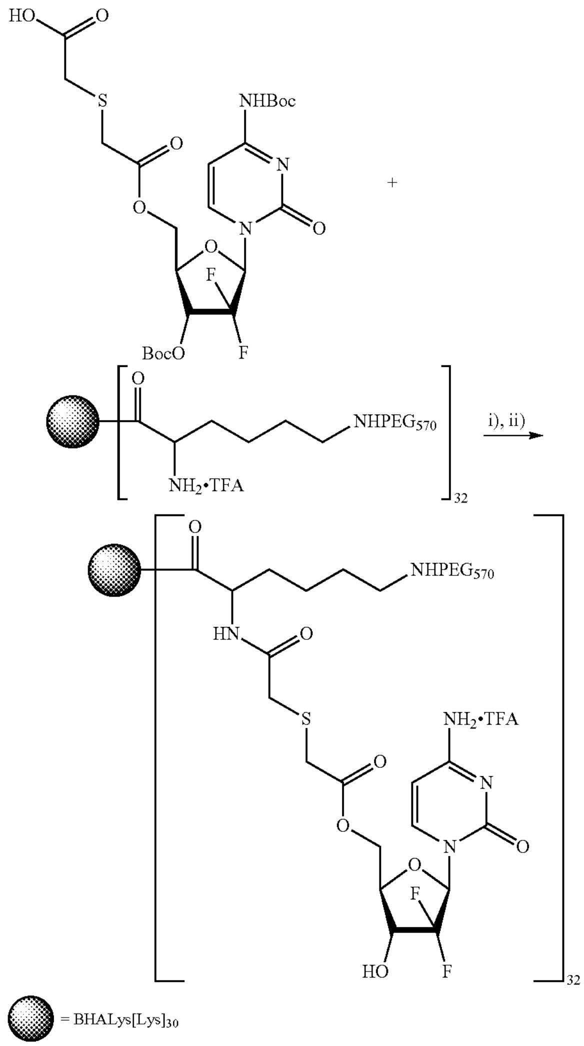

i) PyBOP, NMM, DMF, RT; ii) TFA:DCM (1:1 v/v), RT.

In a similar manner to Example 1 above, 2-((2-(((2R,3R,5R)-5-(4-((tert-butoxycarbonyl)amino)-2-oxopyrimidin-1(2H)-yl)-3-((tert-butoxycarbonyl)oxy)-4,4-difluorotetrahydrofuran-2-yl)methoxy)-2-oxoethyl)thio) acetic acid (0.29 g, 0.49 mmol) and the dendrimer (0.3 g, 0.01 mmol) were used to synthesise the product as a pale-yellow waxy solid (305 mg, 65%). $^{1}H$ NMR (300 MHz, $CD_3OD$) δ 7.95 (s, 39H), 7.29 (s, 10H), 6.29-6.25 (m, 58H), 4.60-4.26 (183H), 3.88-3.44 (m, 1568H), 3.37 (s, 103H), 3.20-3.09 (m, 113H), 2.47 (s, 64H), 1.82-1.17 (m, 388H). Quantification of the amount of gemcitabine molecules per dendrimer by $^{1}H$ NMR spectroscopy showed an average of 29 gemcitabine molecules per dendrimer or 17% wt. gemcitabine.

Example 3: [BHA Lys][Lys]$_{30}$[Lys]$_{32}$ [(α-NH-TDA-Gemcitabine)$_{32}$ (ε-NHPEG$_{\sim 2100}$)$_{32}$] (Compound 3)

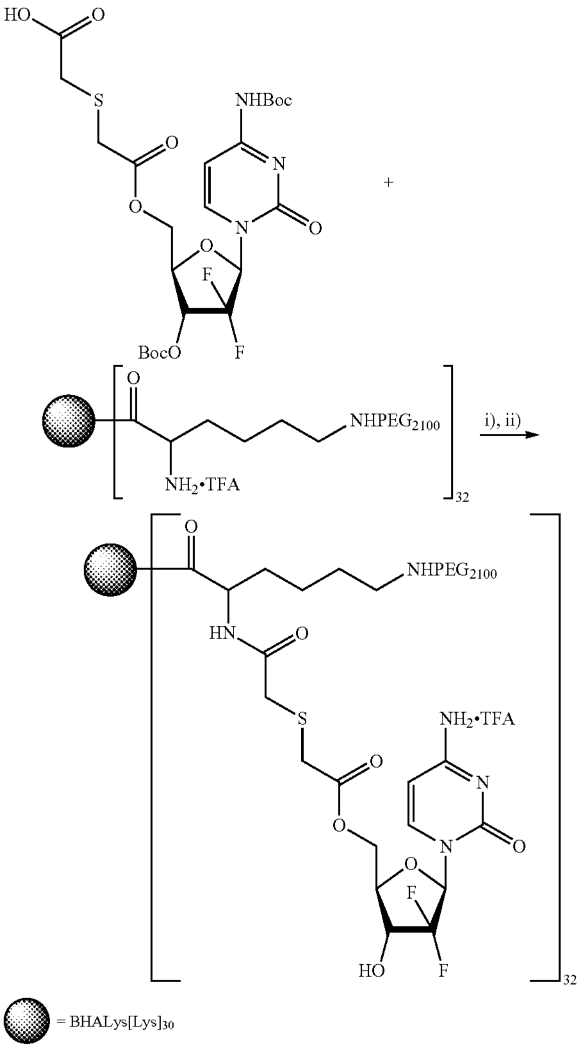

i) PyBOP, NMM, DMF, RT; ii) TFA:DCM (1:1 v/v), RT.

Scheme: i) PyBOP, NMM, DMF, RT; ii) TFA:DCM (1:1 v/v), RT.

In a similar manner to Example 1 above, 2-((2-(((2R,3R,5R)-5-(4-((tert-butoxycarbonyl)amino)-2-oxopyrimidin-1(2H)-yl)-3-((tert-butoxycarbonyl)oxy)-4,4-difluorotetrahydrofuran-2-yl)methoxy)-2-oxoethyl)thio)acetic acid (0.22 g, 0.371 mmol) and the dendrimer (0.73 g, 0.01 mmol) were used to synthesise the product as an off-white solid (520 mg, 80%, over 2 steps). $^{1}H$ NMR (300 MHz, $CD_3OD$) δ 7.77 (bs, 28H), 7.27 (bs, 10H), 6.40-5.99 (m, 50H), 4.72-4.13 (m, 161H), 4.01 (s, 71H), 3.91-3.84 (m, 41H), 3.78-3.54 (m, 5818H), 3.45-3.39 (m, 67H), 3.38 (s, 96H), 3.25 (bs, 86H), 2.14-0.99 (m, 383H). Quantification of the amount of gemcitabine molecules per dendrimer by $^{1}H$ NMR spectroscopy showed an average of 25 gemcitabine molecules per dendrimer or 7.8% wt. gemcitabine, whereas quantification of the amount of gemcitabine molecules per dendrimer by HPLC analysis showed an average of 27 gemcitabine molecules per dendrimer or 8.4% wt. gemcitabine.

Example 3A: [BHA Lys][Lys]$_{30}$[Lys]$_{32}$ [(α-NH-TDA-Gemcitabine)$_{32}$ (ε-NHPEG$_{\sim2100}$)$_{32}$] (Compound 3)

Scheme

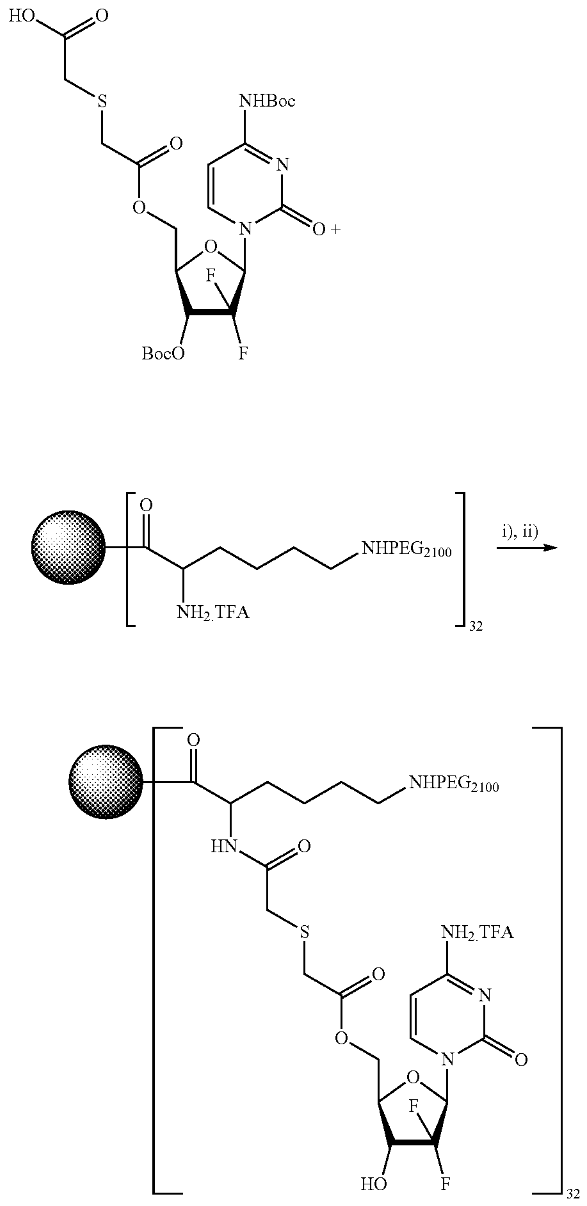

i) PyBOP, NMM, DMF, RT; ii) TFA:DCM (1:1 v/v), RT.

To a solution of 2-((2-(((2R,3R,5R)-5-(4-((tert-butoxycarbonyl)amino)-2-oxopyrimidin-1(2H)-yl)-3-((tert-butoxycarbonyl)oxy)-4,4-difluorotetrahydrofuran-2-yl)methoxy)-2-oxoethyl)thio)acetic acid (4.38 g, 7.36 mmol) in DMF (80 mL) was added solid PyBOP (4.58 g, 8.80 mmol) followed by solid SPL8731 (14.5 g, 0.191 mmol). Finally, NMM (5.40 mL, 49.1 mmol) was added and the reaction was left to stir overnight at RT. The reaction mixture was diluted with ACN (1:1) and purified by ultrafiltration with 30 kDa regenerated cellulose Pellicon 3® 0.11 $m^2$ membrane. After 30 diafiltration volumes of ACN, the retentate was concentrated in vacuo to give the product as light brown residue (17.7 g, 102%). HPLC (C8 Xbridge, 3×100 mm) gradient: 5% ACN/H2O (0-1 min), 5-80% ACN (1-7 min), 80% ACN (7-12 min), 80-5% ACN (12-13 min), 5% ACN (13-15 min), 243 nm, 10 mM ammonium formate buffer, 0.4 mL/min, Rt (min)=9.07 min (broad peak), Purity 100%. The residue was then dissolved in DCM (26 mL) cooled to 0° C. and TFA (26 mL) was added slowly. The reaction was then allowed to stir overnight at RT then slowly added to ice-cold MTBE (340 mL). The resulting solid was obtained by vacuum filtration to give product as free flowing white solid (16.2 g, 98%). $^1H$ NMR (300 MHz, $CD_3OD$) δ 7.91 (brs, 28H), 6.30-6.20 (m, 56H), 4.53-4.26 (m, 156H), 4.00-3.39 (m, 5427H), 3.37 (s, 96H), 3.28-3.07 (m, 113H), 1.98-1.12 (m, 378H). HPLC (C8 Xbridge, 3×100 mm) gradient: 5% ACN/H2O (0-1 min), 5-80% ACN (1-7 min), 80% ACN (7-12 min), 80-5% ACN (12-13 min), 5% ACN (13-15 min), 243 nm, 10 mM ammonium formate buffer, 0.4 mL/min, Rt (min)=8.79 min (broad peak). Purity 100%. TFA analysis by HPLC gave TFA levels at 55505 ppm (5.55%).

Example 4 [BHA Lys][Lys]$_{30}$[Lys]$_{32}$ [(α-NH-DGA-Gemcitabine)$_{32}$ (ε-NHPEG$_{\sim570}$)$_{32}$] (Compound 4)

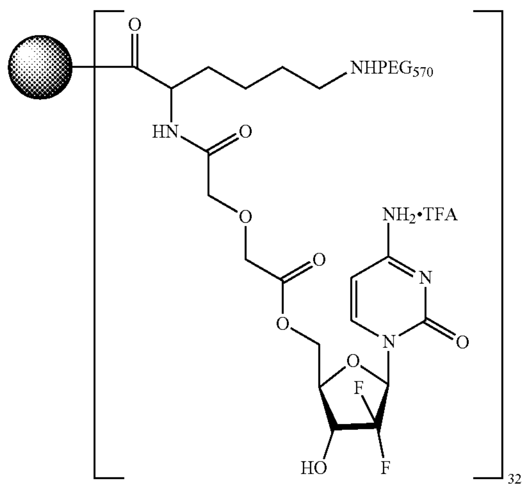

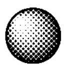 = BHALys[Lys]$_{30}$

In a similar manner to Example 1 above, 2-(2-(((2R,3R,5R)-5-(4-((tert-butoxycarbonyl)amino)-2-oxopyrimidin-1(2H)-yl)-3-((tert-butoxycarbonyl)oxy)-4,4-difluorotetrahydrofuran-2-yl)methoxy)-2-oxoethoxy)acetic acid (0.28 g, 0.49 mmol) and the dendrimer (0.3 g, 0.01 mmol) were used to synthesise the product as a pale-yellow waxy solid (223 mg, 61%). $^1H$ NMR (300 MHz, $CD_3OD$) δ 7.76 (d, J=6 Hz, 28H), 7.28 (s, 9H), 6.25-6.06 (m, 56H), 4.62-4.20 (m, 315H), 3.88-3.54 (m, 1525H), 3.37 (s, 104H), 3.19 (s, 120H), 2.46 (s, 64H), 1.82-1.43 (m, 388H). Quantification of the amount of gemcitabine molecules per dendrimer by $^1H$ NMR spectroscopy showed an average of 28 gemcitabine molecules per dendrimer or 17% wt. gemcitabine.

Example 4A: [BHA Lys][Lys]$_{30}$[Lys]$_{32}$ [(α-NH-DGA-Gemcitabine)$_{32}$ (ε-NHPEG$_{\sim 2100}$)$_{32}$] (Compound 6)

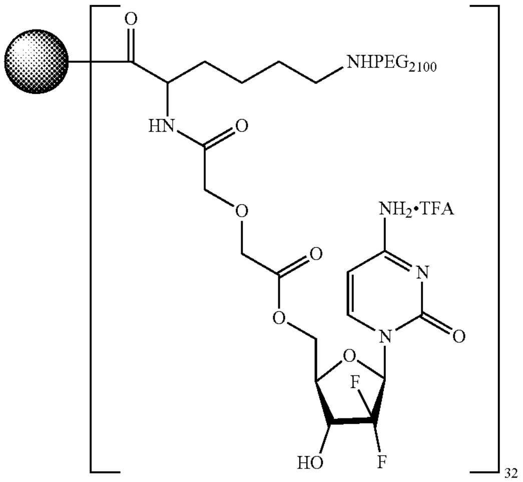

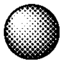
= BHALys[Lys]$_{30}$

In a similar manner to Example 4 above, 2-(2-(((2R,3R,5R)-5-(4-((tert-butoxycarbonyl)amino)-2-oxopyrimidin-1(2H)-yl)-3-((tert-butoxycarbonyl)oxy)-4,4-difluorotetrahydrofuran-2-yl)methoxy)-2-oxoethoxy)acetic acid (4.56 g, 7.87 mmol) and SPL8731 (15.5 g, 0.204 mmol) were used to synthesise the intermediate as pale brown residue. HPLC (C8 Xbridge, 3×100 mm) gradient: 5% ACN/H2O (0-1 min), 5-80% ACN (1-7 min), 80% ACN (7-12 min), 80-5% ACN (12-13 min), 5% ACN (13-15 min), 243 nm, 10 mM ammonium formate buffer, 0.4 mL/min, Rt (min)=8.68 min (broad peak), Purity 100%. The final product was obtained as white solid (16.7 g, 99%, 2 steps) after deprotection in TFA/DCM (1:1, 56 mL) and precipitation in MTBE (380 mL). $^1$H NMR (300 MHz, $CD_3OD$) δ 7.89 (brs, 32H), 6.30-6.17 (m, 64H), 4.69-4.14 (m, 300H), 4.00-3.39 (m, 5576H), 3.37 (s, 93H), 3.28-3.04 (m, 106H), 1.94-1.04 (m, 378H). HPLC (C8 Xbridge, 3×100 mm) gradient: 5% ACN/H2O (0-1 min), 5-80% ACN (1-7 min), 80% ACN (7-12 min), 80-5% ACN (12-13 min), 5% ACN (13-15 min), 243 nm, 10 mM ammonium formate buffer, 0.4 mL/min, Rt (min)=8.52 min (broad peak). Purity 100%. TFA analysis by HPLC gave TFA levels at 71591 ppm (7.16%).

Example 5: [BHA Lys][Lys]$_{30}$[Lys]$_{32}$ [(α-NH-DGA-Gemcitabine)$_{32}$ (ε-NHPEG$_{\sim 1100}$)$_{32}$] (Compound 5)

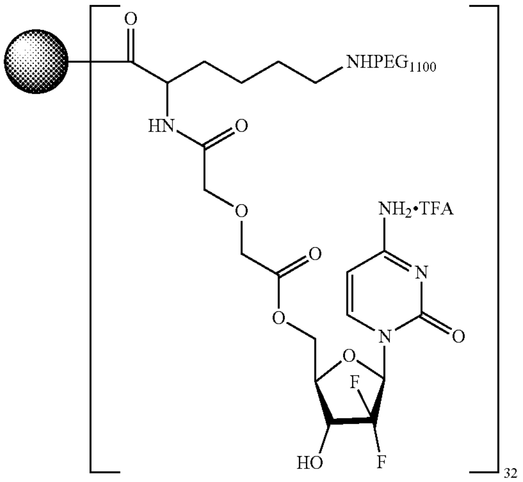

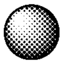
= BHALys[Lys]$_{30}$

In a similar manner to Example 1 above, 2-(2-(((2R,3R,5R)-5-(4-((tert-butoxycarbonyl)amino)-2-oxopyrimidin-1(2H)-yl)-3-((tert-butoxycarbonyl)oxy)-4,4-difluorotetrahydrofuran-2-yl)methoxy)-2-oxoethoxy)acetic acid (0.11 g, 0.18 mmol) and the dendrimer (0.2 g, 0.004 mmol) were used to synthesise product as a pale-yellow waxy solid (220 mg, 83%). $^1$H NMR (300 MHz, $CD_3OD$) δ 7.89 (s, 35H), 7.29 (s, 9H), 6.27-6.21 (m, 56H), 4.64-4.20 (m, 306H), 3.90-3.54 (m, 2978H), 3.43-3.40 (m, 116H), 3.20-3.09 (m, 101H), 2.47-2.45 (m, 64H), 1.86-1.31 (m, 371). Quantification of the amount of gemcitabine molecules per dendrimer by $^1$H NMR spectroscopy showed an average of 29 gemcitabine molecules per dendrimer or 14% wt. gemcitabine.

Example 5B: [BHA Lys][Lys]$_{30}$[Lys]$_{32}$ [(α-NH-TDA-Gemcitabine)$_{32}$ (ε-NHPEG$_{\sim 2100}$)$_{32}$] (Compound 3)

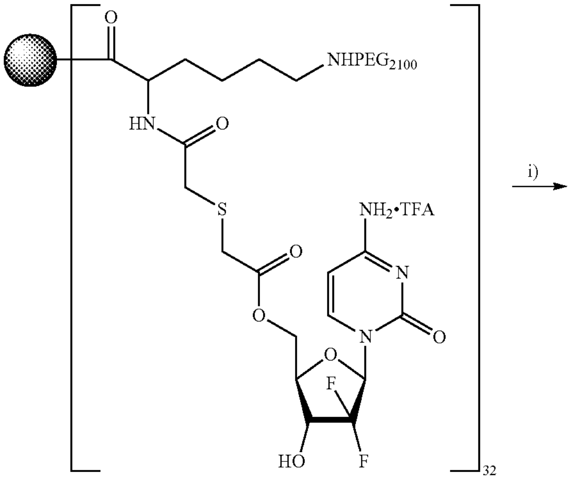

-continued

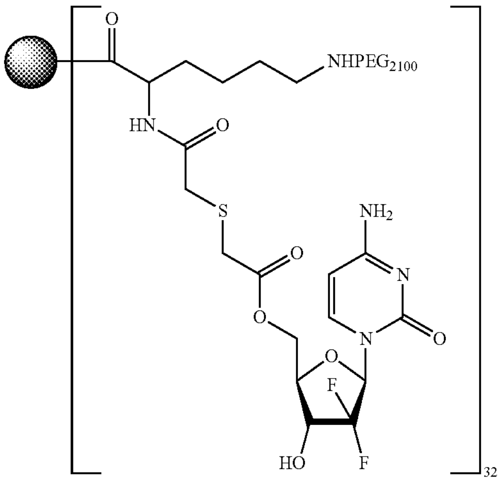

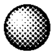 = BHALys[Lys]$_{30}$ i) AmberLyst® A21 ion exchange resin, DCM, RT

To a solution of SPL9133·TFA (16.0 g, 0.182 mmol) in DCM (160 mL) was added AmberLyst® A21 ion exchange resin (32.0 g, 50 g/mmol) and the resulting suspension was allowed to stir overnight at RT. The reaction was filtered off to remove the resin and the organic layer was concentrated in vacuo to give a pale brown residue. The residue was dissolved in THF (60 mL) then slowly added to ice-cold MTBE (320 mL) and the resulting solid was collected by vacuum filtration to give the product as white powder (13.6 g, 89%). HPLC: Column: Agilent ZORBAX 300 Extend-C18 Column, 300A, 5 m, 4.6 mmx250 mm, Gradient: 0% MPB (0-1 min), 0-90% MPB (1-8 min), 90% MPB (8-10 min), 90-0% MPB (10-11 min), 0% ACN (11-18 min), 275 nm, [MPA: 0.01% TFA in $H_2O$; MPB: 0.01% TFA in ACN], 1 mL/min, Rt (min)=7.80 min, Purity 99.98%. $^1H$ NMR (300 MHz, $CD_3OD$) δ 7.73-7.60 (m, 30H), 6.37-6.00 (m, 62H), 4.64-4.3.95 (m, 253H), 3.89-3.38 (m, 5954H), 3.36 (s, 96H), 3.27-3.07 (m, 132H), 2.04-0.97 (m, 378H)·TFA analysis by HPLC gave TFA levels at 257 ppm (0.0257%). Quantification of the amount of gemcitabine molecule per dendrimer by HPLC analysis gave a loading of 9.87% w/w which equated to average of 32 gemcitabine molecules per dendrimer.

Example 5C: [BHA Lys][Lys]$_{30}$[Lys]$_{32}$ [(α-NH-DGA-Gemcitabine)$_{32}$ (ε-NHPEG$_{\sim 2100}$)$_{32}$] (Compound 6)

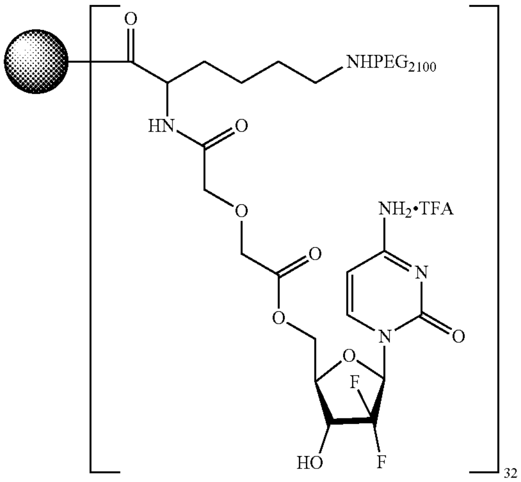

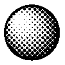 = BHALys[Lys]$_{30}$

In a similar manner to Example 5B above, SPL9134·TFA (16.0 g, 0.183 mmol) in DCM (160 mL) was treated with AmberLyst® A21 ion exchange resin (32.2 g, 50 g/mmol) to give the isolated product after precipitation as white solid (12.2 g, 79%). HPLC: Column: Agilent ZORBAX 300 Extend-C18 Column, 300A, 5 m, 4.6 mmx250 mm, Gradient: 0% MPB (0-1 min), 0-90% MPB (1-8 min), 90% MPB (8-10 min), 90-0% MPB (10-11 min), 0% ACN (11-18 min), 275 nm, [MPA: 0.01% TFA in $H_2O$; MPB: 0.01% TFA in ACN], 1 mL/min, Rt (min)=7.78 min, Purity 99.96%. $^1H$ NMR (300 MHz, $CD_3OD$) S 7.67-7.55 (m, 30H), 6.30-6.00 (m, 60H), 4.64-4.09 (m, 300H), 4.02-3.38 (m, 5552H), 3.36 (s, 93H), 3.27-2.94 (m, 120H), 2.09-0.96 (m, 378H). TFA analysis (HPLC Analysis) gave TFA levels at 395 ppm (0.0395%). Quantification of the amount of gemcitabine molecule per dendrimer by (HPLC analysis) gave a loading of 9.67% w/w which equated to average of 31 gemcitabine molecules per dendrimer.

Example 6: [BHA Lys][Lys]$_{30}$[Lys]$_{32}$ [(α-NH-DGA-Gemcitabine)$_{32}$ (ε-NHPEG$_{\sim 2100}$)$_{32}$] (Compound 6)

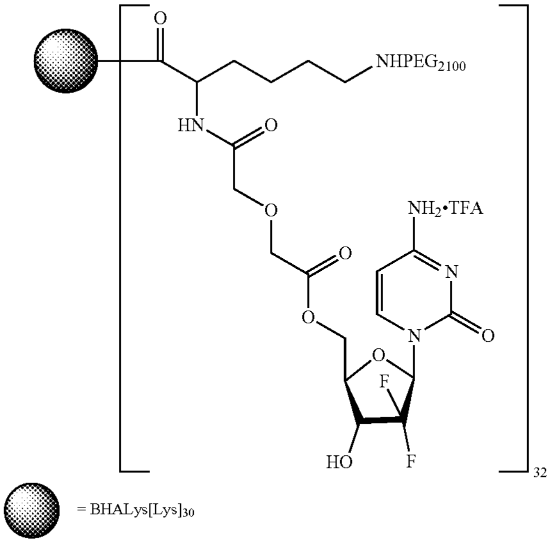

In a similar manner to Example 1 above, 2-(2-(((2R,3R,5R)-5-(4-((tert-butoxycarbonyl)amino)-2-oxopyrimidin-1(2H)-yl)-3-((tert-butoxycarbonyl)oxy)-4,4-difluorotetrahydrofuran-2-yl)methoxy)-2-oxoethoxy)acetic acid (0.10 g, 0.177 mmol) and the dendrimer (0.35 g, 0.005 mmol) were used to synthesise the product as a white solid (204 mg, 75%, 2 steps). $^1$H NMR (300 MHz, $CD_3OD$) δ 7.73 (bs, 26H), 7.26 (bs, 10H), 6.37-5.99 (m, 56H), 4.69-4.11 (m, 277H), 4.01 (s, 76H), 3.89 (s, 51H), 3.84-3.75 (m, 5352H), 3.42 (m, 45H), 3.38 (s, 97H), 3.26 (bs, 78H), 2.17-1.02 (m, 384H). Quantification of the amount of gemcitabine molecules per dendrimer by $^1$H NMR spectroscopy showed an average of 28 gemcitabine molecules per dendrimer or 8.8% wt. gemcitabine, whereas quantification by HPLC analysis showed an average of 32 gemcitabine molecules per dendrimer or 9.9% wt. gemcitabine.

Example 7: [BHA Lys][Lys]$_{30}$[Lys]$_{32}$ [(α-NH-Glu-Gemcitabine)$_{32}$ (ε-NHPEG$_{\sim 1100}$)$_{32}$] (Compound 7)

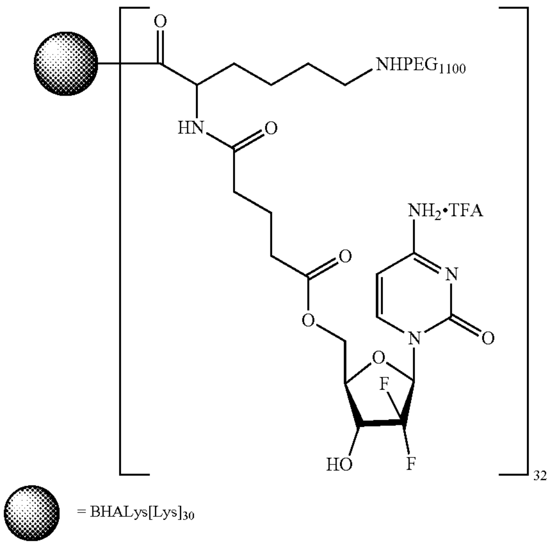

In a similar manner to Example 1 above, 5-(((2R,3R,5R)-5-(4-((tert-butoxycarbonyl)amino)-2-oxopyrimidin-1(2H)-yl)-3-((tert-butoxycarbonyl)oxy)-4,4-difluorotetrahydrofuran-2-yl)methoxy)-5-oxopentanoic acid (28 mg, 0.049 mmol) and the dendrimer 10 (40 mg, 1.03 μmol) (0.025 mL, 0.127 mmol) were used to synthesise [BHA Lys][Lys]$_{30}$[Lys]$_{32}$ [((α-NH-Glu-Gemcitabine)$_{32}$ (ε-NHPEG$_{1100}$)$_{32}$] (20 mg, 50%) as a white semi-solid. $^1$H NMR (300 MHz, $CD_3OD$) δ 7.5-7.7 (m, 20H), 7.2-7.4 (m, 10H), 5.8-6.0 (m, 20H), 6.2-6.4 (m, 20H), 4.14-4.70 (m, 52H), 3.44-4.12 (m, 2806H), 3.2-3.4 (m, 214H), 2.7-3.2 (m, 161H), 2.1-2.7 (m, 88H), 0.89-2.25 (m, 370H).

Example 8: [BHA Lys][Lys]$_{30}$[Lys]$_{32}$ [(α-NH-Glu-Gemcitabine)$_{32}$ (ε-NHPEG$_{\sim 2100}$)$_{32}$] (Compound 8)

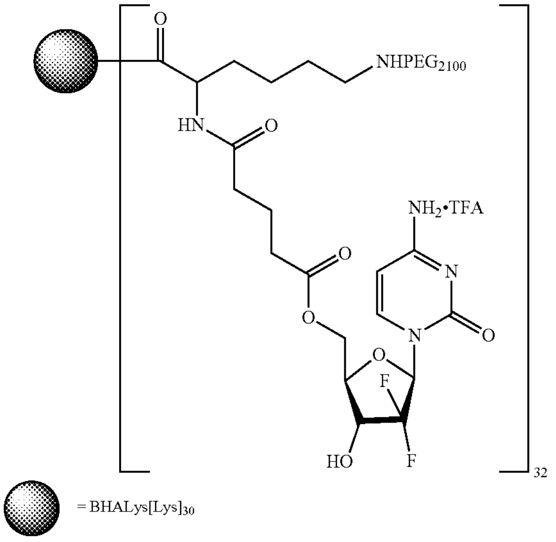

In a similar manner to Example 1 above, 5-(((2R,3R,5R)-5-(4-((tert-butoxycarbonyl)amino)-2-oxopyrimidin-1(2H)-yl)-3-((tert-butoxycarbonyl)oxy)-4,4-difluorotetrahydrofuran-2-yl)methoxy)-5-oxopentanoic acid_(0.20 g, 0.355 mmol) and the dendrimer (0.7 g, 0.01 mmol) were used to synthesise the product as a white solid (286 mg, 63%, over 2 steps). $^1$H NMR (300 MHz, $CD_3OD$) δ 7.77 (bs, 27H), 7.25 (bs, 11H), 6.22 (bs, 56H), 4.64-4.11 (m, 177H), 4.02 (s, 78H), 3.90 (s, 46H), 3.83-3.46 (m, 5365H), 3.43 (bs, 34H), 3.39 (s, 97H), 3.26 (bs, 79H), 2.69-2.13 (m, 122H), 2.10-0.95 (m, 485H). Quantification of the amount of gemcitabine molecules per dendrimer by $^1$H NMR spectroscopy and HPLC analysis showed an average of 28 gemcitabine molecules per dendrimer or 8.8% wt. gemcitabine.

Example 9: Comparative Linker Release Rates in PBS, Citrate Buffer, and Plasma (i) Gemcitabine Release from Dendrimers in PBS and Citrate Buffer A study was carried out to determine the rate of gemcitabine release from dendrimer compounds in PBS and citrate buffer. Gemcitabine-conjugated dendrimers of the present disclosure, and a comparative example dendrimer, were each dissolved in PBS Buffer (2 mL, 10 mM, pH 7.4) or Citrate Buffer (2 mL, 0.1 M, pH 4.5) and held at 37° C. Samples were then analysed by injecting 5 μL of the solution on HPLC. At various time points, samples were analysed by HPLC. HPLC (C8 XBridge, 3×100 mm), gradient: 5% ACN/$H_2O$ (0-1 min), 5-80% ACN (1-7 min), 80% ACN (7-12 min), 80-5% ACN (12-13 min), 5% ACN (13-15 min), 243 nm, 10 mM ammonium formate buffer, 0.4 mL/min.

Figure 2:
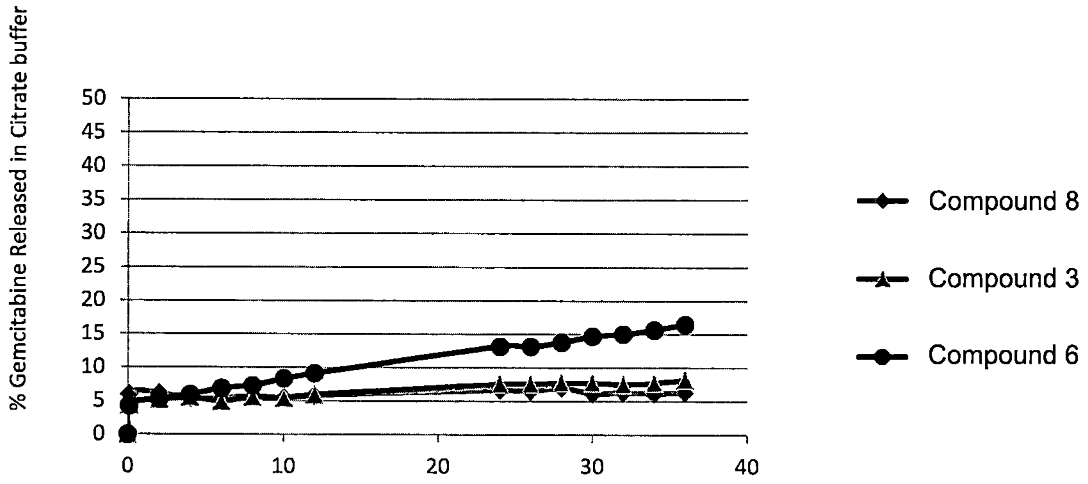
FIG. 2 shows the amount of gemcitabine released (%) from the dendrimer in 1% citrate buffer at pH 4.5 and 37° C.

Results shown in FIG. 1 (PBS) and FIG. 2 (Citrate buffer) and indicate the % gemcitabine released, and are shown in the table below:

(a) % Gemcitabine released in PBS at (pH 7.4; 37° C.):

| Time (h) | % Gemcitabine released in PBS 8 | 3 | 6 |
|---|---|---|---|
| 0 | 0 | 0 | 0 |
| 0.08 | 7.04 | 3.95 | 4.06 |
| 2 | 7.83 | 11.23 | 22.07 |
| 4 | 8.09 | 16.6 | 35.48 |
| 6 | 8.05 | 21.99 | 44.46 |
| 8 | 8.29 | 25.64 | 51.97 |
| 10 | 8.79 | 30.03 | 58.3 |
| 12 | 9.08 | 33.17 | 63.5 |
| 24 | 12.43 | 46.36 | 80.11 |
| 26 | 12.68 | 48.07 | 81.61 |
| 28 | 13.47 | 51.24 | 83.04 |
| 30 | 13.11 | 53.41 | 84.51 |
| 32 | 14.12 | 54.48 | 84.76 |
| 34 | 14.34 | 55.8 | 86.95 |
| 36 | 15.01 | 57.52 | 87.28 |

(b) % Gemcitabine released in Citrate Buffer (pH 4.5; 37° C.):

| Time (h) | % Gemcitabine released in citrate buffer 8 | 3 | 6 |
|---|---|---|---|
| 0 | 0 | 0 | 0 |
| 0.08 | 5.93 | 4.42 | 4.27 |
| 2 | 6.14 | 5.21 | 5.33 |
| 4 | 5.36 | 5.51 | 5.93 |
| 6 | 5.38 | 4.92 | 6.87 |
| 8 | 5.71 | 5.61 | 7.28 |
| 10 | 5.43 | 5.39 | 8.3 |
| 12 | 5.79 | 5.94 | 9.11 |
| 24 | 6.65 | 7.53 | 13.16 |
| 26 | 6.49 | 7.52 | 13.13 |
| 28 | 6.95 | 7.75 | 13.76 |
| 30 | 6.18 | 7.71 | 14.68 |
| 32 | 6.29 | 7.48 | 15.01 |
| 34 | 6.17 | 7.72 | 15.65 |
| 36 | 6.28 | 8.19 | 16.46 |

(ii) Plasma Release Study

Human plasma was thawed in an ice bath then centrifuged for 10 min at 13.2K rpm at 4° C. and the supernatant filtered through a 0.2 μm filter (leaving the protein/enzyme pellet in the micro centrifuge tube). The plasma was placed in a $CO_2$ incubator at 3% $CO_2$ at 42% relative humidity to reach a pH of 7.4.

Gemcitabine HCl (28.5 mg) was dissolved in Milli Q water and the resulting stock solution transferred to a 5 mL volumetric flask and diluted to provide working standard solutions. The working standard solutions were centrifuged for 10 min at 13.2K rpm at 4° C.

Figure 3:
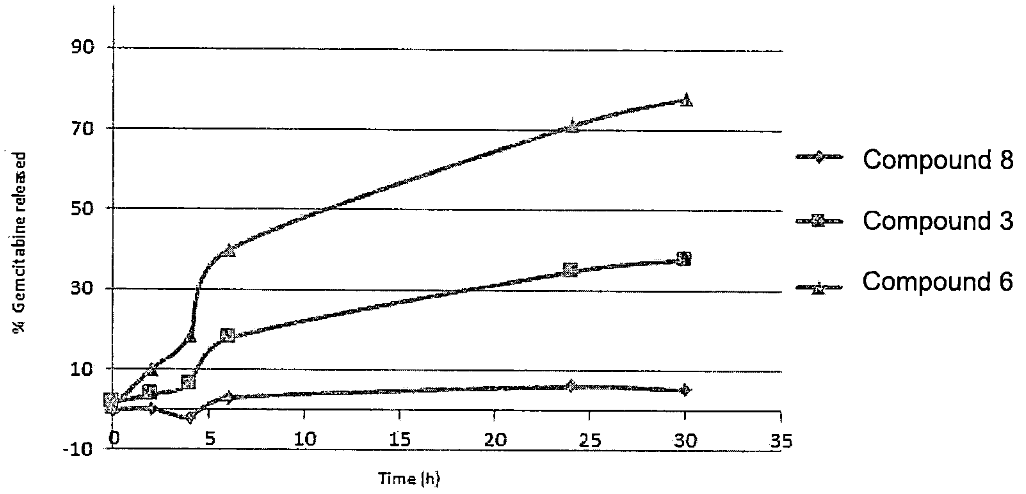
FIG. 3 shows the results of the plasma release study, demonstrating the release rates of gemcitabine (%) from the dendrimers following administration.

The plasma release study was conducted by adding 1 mL of plasma (centrifuged and filtered) to 0.2 mL of dendrimer solution (approximately 2 mg/mL gemcitabine equivalent in miliQ water) for example dendrimers and a comparator. The mixtures were vortexed (30 sec) then incubated at 37° C. 5% $CO_2$. At various timepoints aliquots (0.1 mL) were removed and added to ACN (0.2 mL). The resulting mixtures were vortexed (30 s), centrifuged (10 min, 4° C.), filtered and analysed by HPLC (C8 Xbridge, 3×100 mm, 3.5Å, 0.4 mL/min., gradient: 5% ACN/$H_2O$) (0-1 min), 5-80% ACN (1-7 min), 80% ACN (7-12 min), 80-5% ACN (12-13 min), 5% ACN (13-15 min), 100 mM ammonium formate buffer, column temperature 50° C., sample tray 4° C., 260 nm. The results are shown in FIG. 3.

Human Plasma % release

| Time (h) | 8 | 3 | 6 |
|---|---|---|---|
| 0 | −0.17 | 1.81 | 0.49 |
| 2 | 0.22 | 3.73 | 9.94 |
| 4 | −1.99 | 6.31 | 18.18 |
| 6 | 3.02 | 17.74 | 39.84 |
| 24 | 6.19 | 34.83 | 71.13 |
| 30 | 5.39 | 37.86 | 77.98 |

The above results demonstrate the relative release rates of gemcitabine from the dendrimer following administration.

Example 10: $GI_{50}$ of Gemcitabine-Dendrimer Conjugate

A study was carried out to determine the ability of example dendrimers to inhibit growth of cancer cell lines using an alamarBlue viability assay (Thermo Fisher, DAL1025). $GI_{50}$ is the concentration required to inhibit cell growth by 50%.

The cytotoxicity of compounds toward MDA-MB-231, A549, H460, BxPC3 and CAPAN-1 cells were evaluated for viability. Cells were seeded at a density of 1.2-5×$10^3$ cells, dependent on cell growth rate, in 96 well plates and incubated overnight. Cells were then treated with serial dilutions of test compositions for 72 h (MDA-MB-231, A549 and H460 lines) or 144 h (BxPC3 and CAPAN-1 lines). For cell viability analysis, 10% media volume of alamar Blue was added during the final 6-8 h of incubation. Reduction of alamarBlue in living cells yields a red fluorescent metabolite that can be read on a plate reader (560 nm excitation/610 nm emission.). Cell viability and subsequent GI50 values were was determined from the blank corrected dose-response curves, with 4-parameter nonlinear curve fit, in GraphPad Prism. The results demonstrate that example dendrimers of the present disclosure have potent cytotoxic effects.

Table of $GI_{50}$ for Gemcitabine Compounds:

| Compound | $GI_{50}$ values given in μM Gemcitabine<br>MDA-MB-231 72 h | A549 72 h | H460 72 h | BxPC-3 144 h | CAPAN-1 144 h |
|---|---|---|---|---|---|
| Gemcitabine | 0.004 | 0.011 | 0.042 | 0.009 | 0.009 |
| 8 | 0.103 | 0.5 | | | |
| 3 | 0.007 | 0.05 | 0.077 | 0.008 | 0.008 |
| 6 | 0.005 | 0.045 | 0.056 | 0.001 | 0.006 |
| 9 (Comparative Example) | 0.843 | 4.91 | | | |
| 1 | | 0.051 | 0.215 | 0.007 | 0.033 |
| 4 | 0.003 | 0.031 | 0.061 | 0.013 | 0.011 |
| 2 | 0.004 | 0.034 | 0.412 | 0.007 | 0.021 |
| 5 | 0.003 | 0.044 | 0.046 | 0.007 | 0.003 |

Example 11: In Vivo Efficacy of Gemcitabine-Dendrimer Conjugates

A CAPAN-1 (human pancreatic adenocarcinoma cell line) mouse xenograft pancreatic cancer model study was carried out to assess the anti-tumour efficacy properties of example dendrimers compared to gemcitabine.

Compounds 1, 4, 2 and 5 were prepared by dissolving in sterile saline solution immediately prior to dosing and. Gemcitabine ((DBL™ Gemcitabine injection, Hospira Pty Ltd.) was further diluted in saline solution prior to dosing.

Female NOD-SCID Interleukin-2 receptor gamma chain null mice (aged 9 weeks) were inoculated subcutaneously on the flank with $5\times10^6$ CAPAN-1 cells in PBS:Matrigel (1:1). Mice were weighed and tumours measured twice weekly using electronic callipers. Tumour volume ($mm^3$) was calculated as length (mm)/2×width $(mm)^2$. On day seventeen after implantation, mice with similar sized tumours (mean tumour volume 100 $mm^3$) were randomised into 6 groups of 10 animals.

Compounds were administered via tail vein i.v. injection, twice weekly at 0.1 ml/Og body weight for 3 weeks. Groups were dosed as follows:

1. Saline—vehicle
2. Gemcitabine (120 mg/kg, i.v.)
3. 1 (2 mg/kg, i.v.)
4. 4 (5 mg/kg, i.v.)
5. 2 (5 mg/kg, i.v.)
6. 5 (3 mg/kg, i.v.)

Tumour growth inhibition was analysed at day 29 (where all vehicle animals remained in the study) using one-way ANOVA followed by Dunnett's multiple comparison test. Tumour growth curves of gemcitabine and DEP-gemcitabine were compared over 47 days (when all treatment group animals remained in the study for tumour-related endpoints) using a mixed-effects model followed by Tukey's multiple comparison test. Two mice were lost prior to day 47 due to non-tumour related endpoints (one from gemcitabine and one from SPL-9138 treatment groups). All statistical analysis was performed using GraphPad Prism 8.1.

Figure 4:
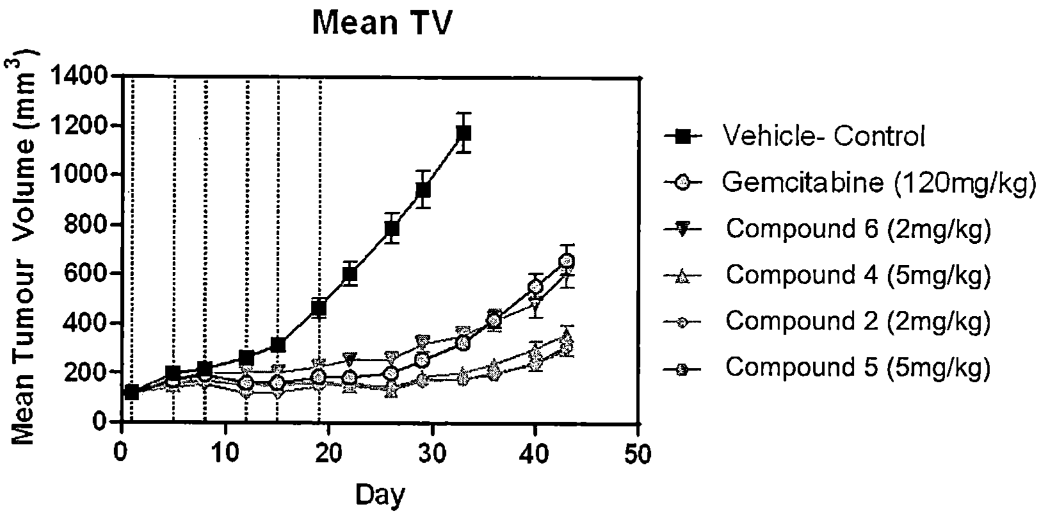
FIG. 4 shows the anti-tumour efficacy (measured in mean tumour volume) of the dendrimers against the CAPAN-1 tumour xenografts.

FIG. 4 shows the anti-tumour efficacy of the treatments against the CAPAN-1 tumour xenografts. Tumour volumes were determined twice weekly and are expressed as mean tumour volume (±SEM). As shown in FIG. 4, 4, 2, 5, induced complete stasis of CAPAN-1 tumours over the dosing study and significantly extended survival beyond that of Gemcitabine. P<0.0001 Mantel Cox regression analysis of Kaplan-Meier survival curves).

| Treatment | Tumour Growth inhibition (%) v vehicle | P (vs Vehicle) |
|---|---|---|
| Gemcitabine | 84 | <0.0001 |
| 1 | 75 | <0.0001 |
| 4 | 91 | <0.0001 |
| 2 | 94 | <0.0001 |
| 5 | 94 | <0.0001 |

Example 12: Dosing Regimen Study of Gemcitabine-Dendrimer Conjugate

A CAPAN-1 (human pancreatic adenocarcinoma cell line) mouse xenograft pancreatic cancer model was established to assess the effects of weekly compared to biweekly administration of an example dendrimer.

Compound 1 was prepared as described above. Mice were inoculated and tumours sized as described above. On day seventeen after implantation, mice with similar sized tumours (mean tumour volume 140 $mm^3$) were randomised into 2 groups of 5 animals:

1. 1 (5 mg/kg, i.v.) weekly for 3 weeks; and
2. 1 (2 mg/kg, i.v.) biweekly for 3 weeks.

Figure 5:
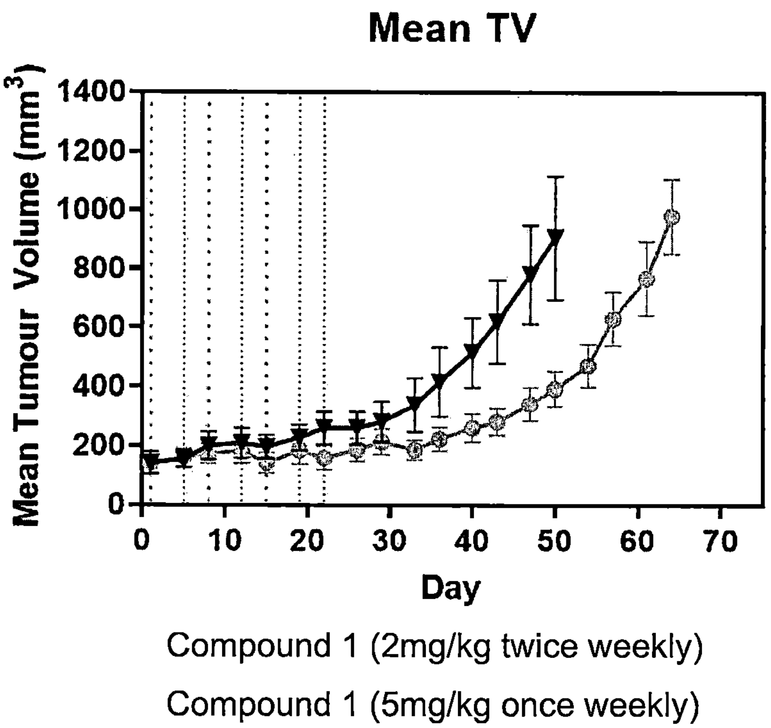
FIG. 5 shows the anti-tumour efficacy (measured in mean tumour volume) of the dendrimers against the CAPAN-1 tumour xenografts, based on once-weekly and twice-weekly dosing intervals.

FIG. 5 shows the anti-tumour efficacy of the treatments against the CAPAN-1 tumour xenografts. Tumour volumes were determined twice weekly and are presented as mean tumour volume (±SEM). Compound 1, given weekly at 5 mg/kg was more effective at suppressing tumour growth than 1, given biweekly at 2 mg/kg.

Example 13a: In Vivo Efficacy Study of Xenograft of Gemcitabine-Dendrimer Conjugate with Abraxane®

A CAPAN-1 (human pancreatic adenocarcinoma cell line) mouse xenograft pancreatic cancer model was used to assess the anti-tumour efficacy properties of 3 and 6 alone or in combination with Abraxane® (albumin-bound paclitaxel), compared to Gemcitabine, alone or in combination with Abraxane®. Mice were inoculated and tumours sized as described above. On day nineteen after implantation, mice with similar sized tumours (mean tumour volume 100 $mm^3$) were randomised into 7 groups of 10 animals. Gemcitabine, 3 and 6 were prepared as described above. Abraxane® was dissolved in saline solution immediately prior to dosing.

Abraxane®, gemcitabine and dendrimers were administered at days 1, 10, and 17 via tail vein i.v. injection, at 0.1 ml/10 g body weight.

| Treatment | Dose |
|---|---|
| Vehicle | |
| Gemcitabine | 120 mg/kg |
| Abraxane ® | 40 mg/kg |
| Gemcitabine + Abraxane ® | Gemcitabine at 120 mg/kg + Abraxane ® at 40 mg/kg |
| 3 | 6.5 mg/kg |
| 6* | 4 mg/kg |
| 6* + Abraxane ® | 6 at 4 mg/kg + Abraxane ® at 40 mg/kg |

*Compound 6 was administered at 5 mg/kg on day 1, and 4 mg/kg on days 10 and 17.

Example 13b: In Vivo Efficacy Study of Xenograft of Gemcitabine-Dendrimer Conjugate with Docetaxel-Dendrimer Conjugate In an extension of Example 13a, two additional groups of mice were prepared and dosed to assess the anti-tumour efficacy properties of a taxane-dendrimer combined with a nucleoside analogue-dendrimer (e.g. 6). Mice were inoculated and tumours sized as described above. DEP-DTX, a docetaxel-dendrimer conjugate, was prepared as described in Example 19 of WO2012167309, and has the structure $BHALys[Lys]_{32}[\alpha\text{-TDA-DTX}]_{32}[\varepsilon\text{-PolyPEG}_{2000}]_{32}$:

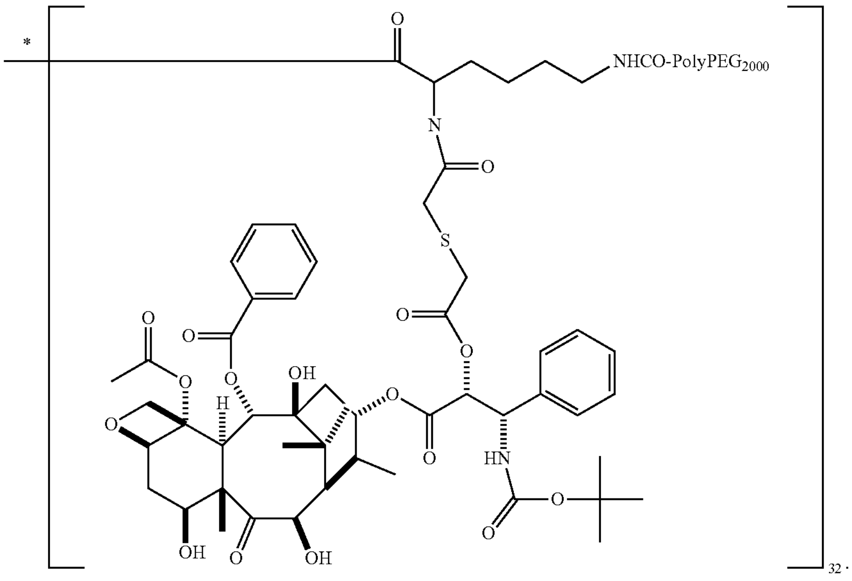

* = BHALys[Lys]$_{16}$

Dendrimers were administered weekly via tail vein i.v. injection, at 0.1 ml/10 g body weight for 3 weeks.

| Treatment | Dose |
|---|---|
| DEP-DTX | 24 mg/kg |
| 6* + DEP-DTX | 6 at 4 mg/kg + DEP-DTX at 10 mg/kg |

*Compound 6 was administered at 5 mg/kg on day 1 and 4 mg/kg on days 10 and 17

Results of Examples 13a and b

Tumour growth inhibition was analysed at day 29 (where no vehicle animals remained in the study) using one-way ANOVA followed by Dunnett's multiple comparison test. All statistical analyses were performed using GraphPad Prism 8.1.

| Treatment | Tumour Growth inhibition (%) v vehicle at day 29 | P (vs Vehicle) |
|---|---|---|
| Gemcitabine | 59 | P < 0.001 |
| Abraxane ® | 92 | P < 0.001 |
| Gemcitabine + Abraxane ® | 95 | P < 0.001 |
| 3 | 103 | P < 0.001 |
| 6 | 83 | P < 0.001 |
| 6 + Abraxane ® | 108 | P < 0.001 |
| DEP-DTX | 108 | P < 0.001 |
| 6 + DEP-DTX | 107 | P < 0.001 |

At day 29, 3 was significantly more effective than Gemcitabine in CAPAN-1 tumours over the dosing study; and the combination of Abraxane® and 6 was significantly more effective than either agent alone (P=0.0001), or gemcitabine with Abraxane® (P=0.005) and induced complete tumour regression (P<0.0001). The combination of DEP-DTX and 6 was more effective than 6 alone and induced complete tumour regression (P<0.0001).

Figure 6:
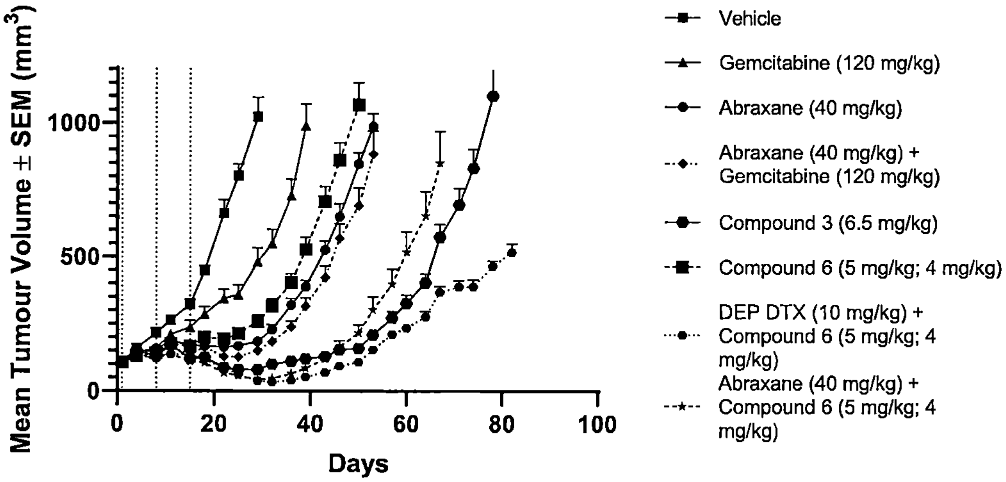
FIG. 6 shows the anti-tumour efficacy of the dendrimers against the CAPAN-1 tumour xenografts, alone or in combination with Abraxane® or DEP-DTX.

FIG. 6 shows the anti-tumour efficacy of the treatments against the CAPAN-1 tumour xenografts out to day 82 when the experiment was ended. Tumour volumes were determined twice weekly and are expressed as mean tumour volume (±SEM). Graphs are shown until the first mouse in each group reached tumour endpoint.

As shown in FIG. 6, 3 was more effective than Gemcitabine and also more effective than the combination of gemcitabine and Abraxane® in CAPAN-1 tumours over the dosing study.

The combination of Abraxane® and 6 was more effective than either agent alone, or gemcitabine with Abraxane® The combination of DEP-DTX and 6 was more effective than 6 alone, and any other group.

In general, compounds were well tolerated and showed minimal weight loss during the first two weeks corresponding to dosing, with recovery and subsequent weight gain. One mouse was removed from the experiment at day 8 due to rapid weight loss starting after the first dosing of Abraxane® plus 6. Maximum body weight loss in all groups was below 10%, except the group receiving 6 at 5 mg/kg and Abraxane®, showed mean weight loss of 10.27%.

Example 14: In Vivo Efficacy Study of Xenograft of Two Gemcitabine-Dendrimer Conjugates in a Pancreatic Adenocarcinoma Mouse Xenograft Model A CAPAN-1 (human pancreatic adenocarcinoma cell line) mouse xenograft pancreatic cancer model was used to assess the anti-tumour efficacy properties of 3 and 6. NSG (NOD-SCID Interleukin-2 receptor gamma chain null) mice were inoculated and tumours sized as described above. On day 24 after implantation, mice with similar sized tumours (mean tumour volume 100 mm$^3$) were randomised into four groups of 10 animals for each tumour type. Gemcitabine, 3 and 6 were prepared as described above.

Gemcitabine was administered twice weekly and dendrimers were administered weekly for 3 weeks via tail vein i.v. injection, at 0.1 ml/10 g body weight.

| Treatment | Dose |
|---|---|
| Vehicle/Saline | |
| Gemcitabine | 120 mg/kg |
| 3 | 6 mg/kg |
| 6 | 5 mg/kg |

Figure 7:
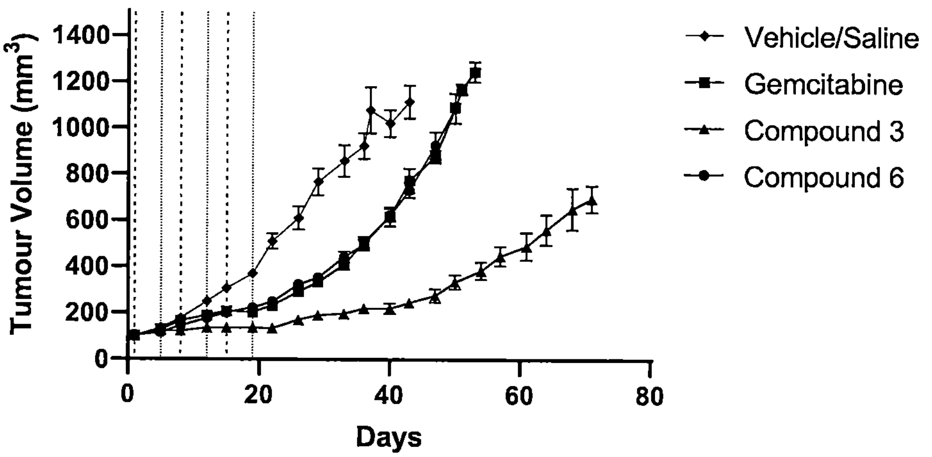
FIG. 7 shows the anti-tumour efficacy (measured in mean tumour volume) of the dendrimers against the CAPAN-1 tumour xenografts.

FIG. 7 shows the anti-tumour efficacy of the treatments against the CAPAN-1 tumour xenografts. Tumour volumes were determined twice weekly and are expressed as mean tumour volume (±SEM). As shown in FIG. 7, 3 was significantly more effective than Gemcitabine or 6 in CAPAN-1 tumours over the study.

Example 15: In Vivo Efficacy Study of Xenograft of Two Gemcitabine-Dendrimer Conjugates in a Lung Adenocarcinoma Mouse Xenograft Model A A549 (human adenocarcinomic human alveolar basal epithelial) cell line was used to assess the anti-tumour efficacy properties of 3. NSG mice were inoculated and tumours sized as described above. On day 30 after implantation, mice with similar sized tumours (mean tumour volume 100 $mm^3$) were randomised into four groups of 10 animals for each tumour type. Gemcitabine and 3 were prepared as described above.

Gemcitabine was administered twice weekly and dendrimer was administered weekly for 3 weeks via tail vein i.v. injection, at 0.1 ml/10 g body weight.

| Treatment | Dose |
|---|---|
| Vehicle/Saline | |
| Gemcitabine | 120 mg/kg |
| 3 | 6 mg/kg |

Figure 8:
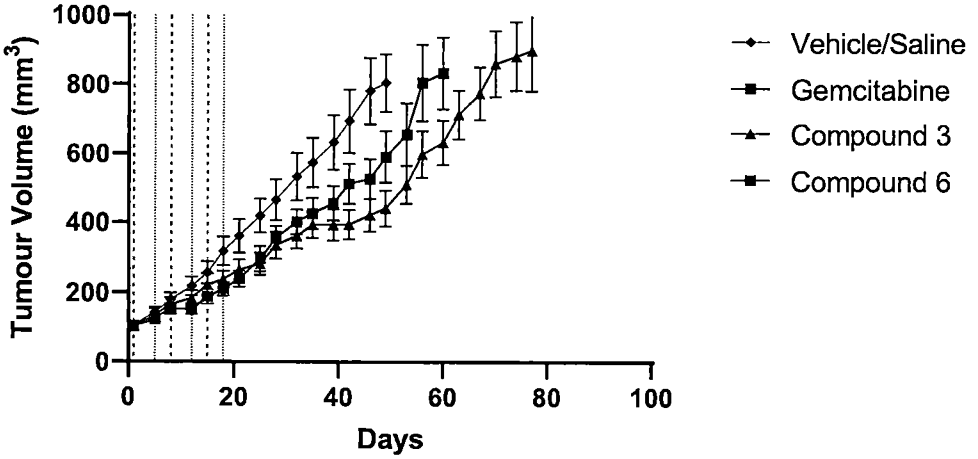
FIG. 8 shows the anti-tumour efficacy (measured in mean tumour volume) of the dendrimer against the A549 tumour xenografts.

FIG. 8 shows the anti-tumour efficacy of the treatments against the A549 tumour xenografts. Tumour volumes were determined twice weekly and are expressed as mean tumour volume (±SEM). As shown in FIG. 8, 3 was more effective than Gemcitabine in A549 tumours over the study.

Example 16: In Vivo Efficacy Study of Xenograft of Gemcitabine-Dendrimer Conjugate with Carboplatin An OVCAR-3 (human Ovarian Carcinoma cell line) mouse xenograft cancer model was used to assess the anti-tumour efficacy properties of 3 alone or in combination with Carboplatin, compared to Gemcitabine, alone or in combination with Carboplatin. NSG Mice were inoculated and tumours sized as described above. On day twenty nine after implantation, mice with similar sized tumours (mean tumour volume 100 $mm^3$) were randomised into 10 groups of 10 animals. Gemcitabine and 3 were prepared as described above. DBLCarboplatin (Hospira) was dissolved in saline solution and further diluted in 5% glucose immediately prior to dosing.

Gemcitabine was administered twice weekly and dendrimers and carboplatin were administered weekly for 3 weeks via tail vein i.v. injection, at 0.1 ml/10 g body weight.

| Treatment | Dose |
|---|---|
| Vehicle/Saline | |
| Gemcitabine + glucose vehicle | 80 mg/kg |
| Gemcitabine | 120 mg/kg |
| Carboplatin + saline vehicle | 40 mg/kg |
| Carboplatin | 60 mg/kg |
| 3 + glucose vehicle | 4 mg/kg |
| 3 | 6 mg/kg |
| Gemcitabine + Carboplatin | Gemcitabine at 80 mg/kg + Carboplatin at 40 mg/kg |
| 3 + Carboplatin | 3 at 4 mg/kg + Carboplatin at 40 mg/kg |
| 3 + Carboplatin | 3 at 6 mg/kg + Carboplatin at 40 mg/kg |

Figure 9:
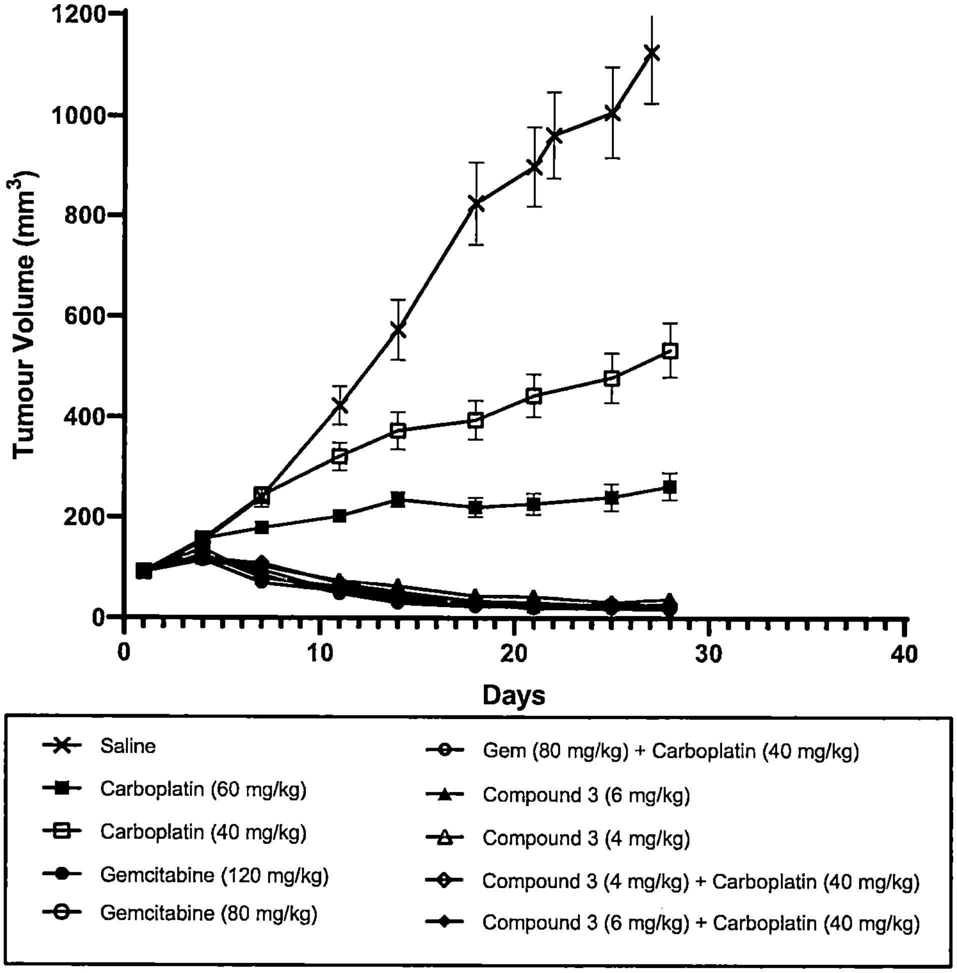
FIG. 9 shows the anti-tumour efficacy (measured in mean tumour volume) of the dendrimers against the OVCAR-3 tumour xenografts, alone or in combination with Carboplatin.

FIG. 9 shows the anti-tumour efficacy of the treatments against the OVCAR-1 tumour xenografts. Tumour volumes were determined twice weekly and are expressed as mean tumour volume (±SEM). As shown in FIG. 9, in OVCAR-1 tumours (i) 3 at 4 mg/kg and 6 mg/kg was more effective than Gemcitabine, (ii) 3 and carboplatin was as or more effective than Gemcitabine or carboplatin alone.

The invention claimed is:

1. A dendrimer comprising:

i) a core unit (C) which is

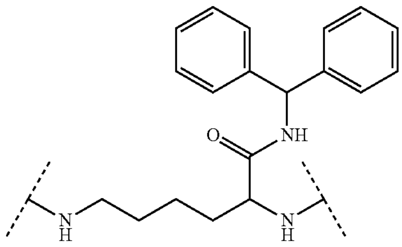

;

and ii) building units (BU), which are

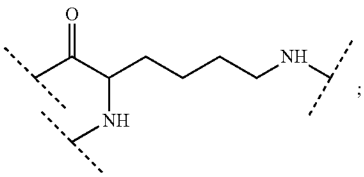

;

wherein the acyl group of each building unit provides a covalent attachment point for attachment to the core or to a previous generation building unit; and wherein each nitrogen atom provides a covalent attachment point for covalent attachment to a subsequent generation building unit, a first terminal group or a second terminal group;

wherein the core unit is covalently attached to two building units via amide linkages, each amide linkage being formed between a nitrogen atom present in the core unit and the carbon atom of an acyl group present in a building unit;

the dendrimer being a five generation building unit dendrimer;

wherein building units of different generations are covalently attached to one another via amide linkages formed between a nitrogen atom present in one building unit and the carbon atom of an acyl group present in another building unit;

the dendrimer further comprising:

iii) a plurality of first terminal groups (T1) each comprising a residue of a nucleoside analogue, which nucleoside analogue has a hydroxyl group, covalently attached to a diacyl linker group of formula:

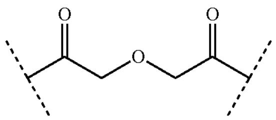

or

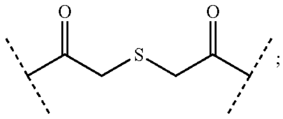

;

and iv) a plurality of second terminal groups (T2) each comprising a hydrophilic polymeric group which is a polyethylene glycol (PEG) group; or a pharmaceutically acceptable salt thereof.

2. The dendrimer as claimed in claim 1, wherein the nucleoside analogue is selected from the group consisting of gemcitabine, cytarabine, and azacitadine.

3. The dendrimer as claimed in claim 2, wherein the nucleoside analogue is gemcitabine.

4. The dendrimer as claimed in claim 1, wherein the nucleoside analogue is gemcitabine and is covalently attached to the diacyl linker group as shown below:

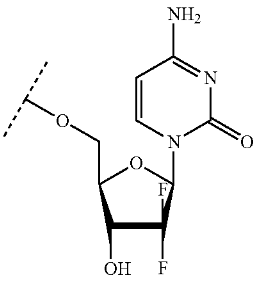

or as shown below

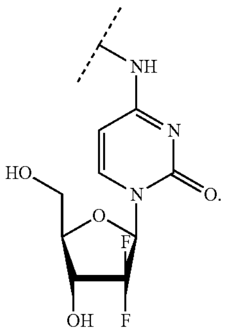

5. The dendrimer as claimed in claim 4, wherein the first terminal group is:

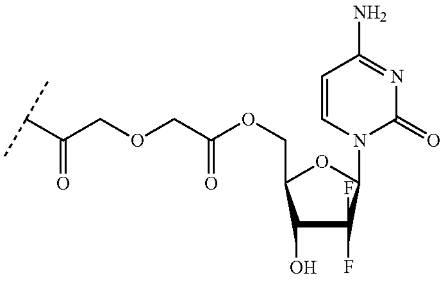

or wherein the first terminal group is:

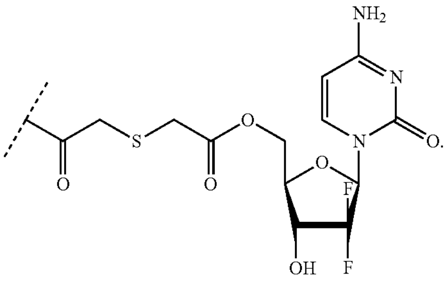

6. The dendrimer as claimed in claim 1, wherein the second terminal groups comprise PEG groups having a mean molecular weight of at least 500 Daltons.

7. The dendrimer as claimed in claim 1, wherein the second terminal groups each comprise a PEG group covalently attached to a PEG linking group (L1) via an ether linkage formed between a carbon atom present in the PEG group and an oxygen atom present in the PEG linking group, and each second terminal group is covalently attached to a building unit via an amide linkage formed between a nitrogen atom present in a building unit and the carbon atom of an acyl group present in the PEG linking group.

8. The dendrimer as claimed in claim 7, wherein the dendrimer comprises surface units comprising an outer building unit attached to a first terminal group and a second terminal group, the surface units having the structure:

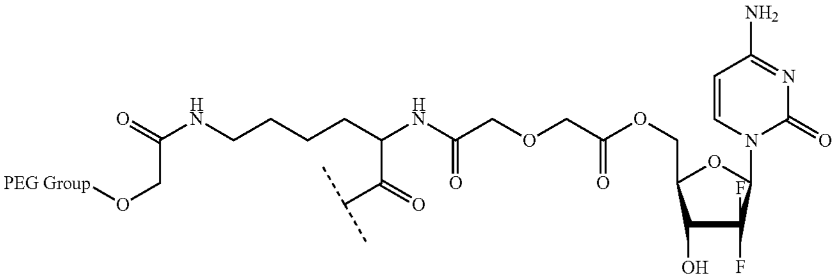

or

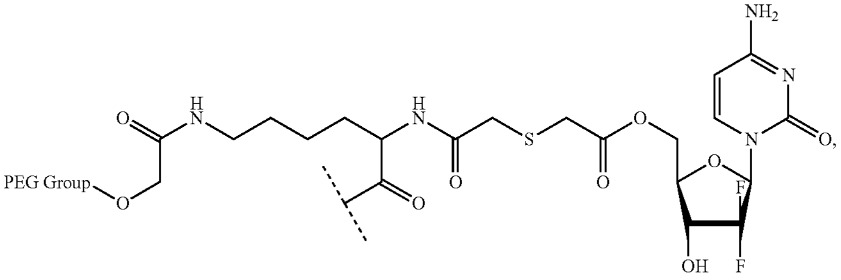

and wherein the PEG group is a methoxy-terminated PEG having an average molecular weight in the range of from 500 to 2500 Daltons.

9. The dendrimer as claimed in claim 1, wherein at least 40% of the nitrogen atoms present in the outer building units are each covalently attached to a first terminal group; and at least 40% of the nitrogen atoms present in the outer building units are each covalently attached to a second terminal group.

10. The dendrimer as claimed in claim 1, wherein the dendrimer is a compound has the structure shown in FIG. 10, in which T1' represents a first terminal group which is

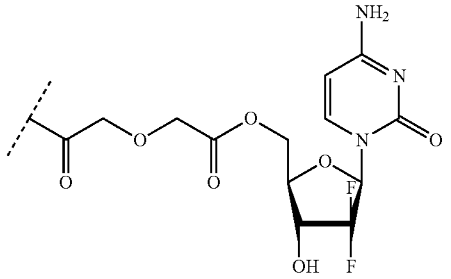

or

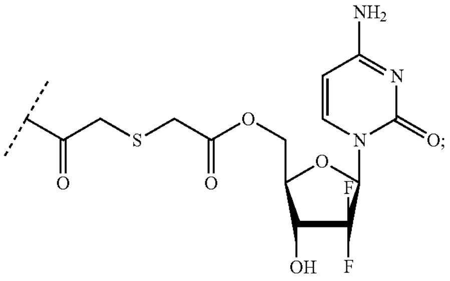

and

T2' represents a second terminal group which is

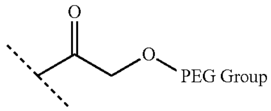

wherein the PEG group is a methoxy-terminated PEG having an average molecular weight in the range of from 500 to 2500 Daltons, or T2' represents H, and wherein less than 5 of T2' are H.

11. The dendrimer as claimed in claim 1, wherein the second terminal groups comprise PEG groups having an average molecular weight in the range of from 1900 to 2300 Daltons.

12. A pharmaceutical composition comprising:

i) the dendrimer as claimed in claim 1, or a pharmaceutically acceptable salt thereof; and ii) a pharmaceutically acceptable excipient.

13. The dendrimer as claimed in claim 1, wherein the diacyl linker is

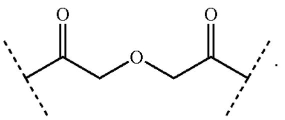

14. The dendrimer as claimed in claim 1, wherein the diacyl linker is

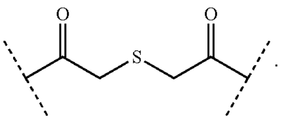

15. A method of treating cancer comprising administering to a subject in need thereof a therapeutically effective amount of the dendrimer according to claim 1.

16. The method as claimed in claim 15, wherein the cancer is selected from the group consisting of breast cancer, ovarian cancer, non-small cell lung cancer, an upper gastrointestinal cancer, pancreatic cancer, and bladder cancer.

17. The method as claimed in claim 15, wherein the amount of dendrimer administered is sufficient to deliver an amount of active agent in the range of from 5 mg to 200 mg of nucleoside analogue/$m^2$.

18. The method as claimed in claim 17, wherein the method comprises administering the dendrimer in combination with a second dendrimer, and wherein the second dendrimer comprises:

i) a core unit (C); and ii) building units (BU), each building unit being a lysine residue or an analogue thereof;

wherein the core unit is covalently attached to two building units via amide linkages, each amide linkage being formed between a nitrogen atom present in the core unit and the carbon atom of an acyl group present in a building unit;

the second dendrimer being a five generation building unit dendrimer;

wherein building units of different generations are covalently attached to one another via amide linkages formed between a nitrogen atom present in one building unit and the carbon atom of an acyl group present in another building unit;

the second dendrimer further comprising:

iii) a plurality of first terminal groups (T1) each comprising a residue of an oncology agent, which oncology agent has a hydroxyl group, covalently attached to a diacyl linker group of formula:

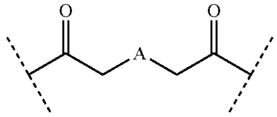

, wherein A is a $C_2$-$C_{10}$ alkylene group which is interrupted by at least one O, S, NH, or N(Me), or in which A is a heterocycle selected from the group consisting of tetrahydrofuran, tetrahydrothiophene, pyrrolidine, and N-methylpyrrolidine; and iv) a plurality of second terminal groups (T2) each comprising a hydrophilic polymeric group;

or a pharmaceutically acceptable salt thereof.

19. The method as claimed in claim 18, wherein the oncology agent is a taxane.

20. The method as claimed in claim 18, wherein the oncology agent is a topoisomerase I inhibitor.

21. The method as claimed in claim 15, wherein the dendrimer is administered in combination with a further anticancer agent.

22. The method as claimed in claim 21, wherein the further anticancer agent is selected from the group consisting of capecitabine, Nab-paclitaxel, docetaxel, cabazitaxel, doxorubicin, vindesine, irinotecan, folinic acid, 5-fluorouracil, methotrexate, pemetrexed, lapatinib, nintedanib, sunitinib, olaparib, niraparib, carboplatin, paclitaxel, SN38, cisplatin, oxaliplatin, paclitaxel, erlotinib, and irinotecan.

* * * * *